United States Patent
Gauthier et al.

(10) Patent No.: US 9,388,246 B2
(45) Date of Patent: *Jul. 12, 2016

(54) TLR3 BINDING AGENTS

(75) Inventors: Laurent Gauthier, Marseilles (FR); Catherine Massacrier, Tassin la demi lune (FR); Yannis Morel, Marseilles (FR); Carine Paturel, Marcy l'E-toile (FR)

(73) Assignee: INNATE PHARMA, Marseilles (FR)

( * ) Notice: Subject to any disclaimer, the term of this patent is extended or adjusted under 35 U.S.C. 154(b) by 859 days.

This patent is subject to a terminal disclaimer.

(21) Appl. No.: 13/102,019

(22) Filed: May 5, 2011

(65) Prior Publication Data

US 2012/0034232 A1 Feb. 9, 2012

Related U.S. Application Data

(63) Continuation of application No. PCT/EP2010/059946, filed on Jul. 9, 2010.

(60) Provisional application No. 61/224,548, filed on Jul. 10, 2009.

(51) Int. Cl.
| | |
|---|---|
| *A61K 39/395* | (2006.01) |
| *C07K 16/28* | (2006.01) |
| *C12N 5/16* | (2006.01) |
| *C12N 5/10* | (2006.01) |
| *A61P 31/00* | (2006.01) |
| *A61P 37/06* | (2006.01) |

(52) U.S. Cl.
CPC ......... *C07K 16/2896* (2013.01); *C07K 2317/34* (2013.01); *C07K 2317/54* (2013.01); *C07K 2317/56* (2013.01); *C07K 2317/565* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | |
| 4,816,567 A | 3/1989 | Cabilly et al. | |
| 5,229,275 A | 7/1993 | Goroff | |
| 5,491,084 A | 2/1996 | Chalfie et al. | |
| 5,567,610 A | 10/1996 | Borrebaeck et al. | |
| 5,660,827 A | 8/1997 | Thorpe et al. | |
| 6,162,963 A | 12/2000 | Kucherlapati et al. | |
| 6,267,958 B1 | 7/2001 | Andya et al. | |
| 6,486,382 B1 | 11/2002 | Gordan-Kamm et al. | |
| 8,076,460 B2 | 12/2011 | Matsumoto et al. | |
| 8,221,755 B2 | 7/2012 | Dunlop et al. | |
| 8,222,375 B2 | 7/2012 | Terrett et al. | |
| 8,354,508 B2 | 1/2013 | Diedrich et al. | |
| 8,409,567 B2 | 4/2013 | Cunningham et al. | |
| 8,460,659 B2 | 6/2013 | Cunningham et al. | |
| 8,540,986 B2 | 9/2013 | Cunningham et al. | |
| 8,586,041 B2 | 11/2013 | van de Winkel et al. | |
| 8,802,103 B2 | 8/2014 | Gurney et al. | |
| 8,828,400 B2 | 9/2014 | Leuchs et al. | |
| 9,238,693 B2 | 1/2016 | Cunningham et al. | |
| 9,255,153 B2 | 2/2016 | Cunningham et al. | |
| 2002/0136719 A1 | 9/2002 | Shenoy et al. | |
| 2005/0123536 A1 | 6/2005 | Law et al. | |
| 2005/0180972 A1 | 8/2005 | Wahl et al. | |
| 2009/0105460 A1 | 4/2009 | Matsumoto et al. | |
| 2010/0166778 A1 | 7/2010 | Cunningham et al. | |
| 2011/0008352 A1 | 1/2011 | Cunningham et al. | |
| 2012/0064095 A1 | 3/2012 | Cunningham et al. | |
| 2013/0090457 A1 | 4/2013 | Cunningham et al. | |
| 2013/0244281 A1 | 9/2013 | Cunningham et al. | |
| 2013/0280263 A1 | 10/2013 | Cunningham et al. | |
| 2014/0017250 A1 | 1/2014 | Cunningham et al. | |
| 2014/0065154 A1 | 3/2014 | Gauthier et al. | |
| 2014/0093508 A1 | 4/2014 | Cunningham et al. | |
| 2014/0212426 A1 | 7/2014 | Cunningham et al. | |
| 2015/0140000 A1 | 5/2015 | Bonnafous et al. | |

FOREIGN PATENT DOCUMENTS

| | | |
|---|---|---|
| WO | WO 98/50547 A2 | 11/1998 |
| WO | WO 98/56418 | 12/1998 |
| WO | WO 03/106499 A1 | 12/2003 |
| WO | WO 2006/060513 A2 | 6/2006 |
| WO | WO 2007/051164 A2 | 5/2007 |
| WO | WO 2008/049897 | 5/2008 |
| WO | WO 2009/130616 | 10/2009 |
| WO | WO 2010/051470 | 5/2010 |
| WO | WO 2010/051470 A2 | 5/2010 |

(Continued)

OTHER PUBLICATIONS

Brummell et al, Biochemistry; 1993; vol. 32, pp. 1180-1187.*

(Continued)

*Primary Examiner* — Bridget E Bunner
*Assistant Examiner* — Fozia Hamud
(74) *Attorney, Agent, or Firm* — Knobbe Martens Olson & Bear, LLC

(57) ABSTRACT

The present invention relates to antibodies (e.g. monoclonal antibodies), antibody fragments, and derivatives thereof that specifically bind TLR3, and that optionally further modulate, e.g. inhibit, signaling. The invention also relates to cells producing such antibodies; methods of making such antibodies; fragments, variants, and derivatives of the antibodies; pharmaceutical compositions comprising the same; methods of using the antibodies to diagnose, treat or prevent diseases, e.g. autoimmune diseases, inflammatory diseases and the like.

55 Claims, 20 Drawing Sheets

(56) References Cited

FOREIGN PATENT DOCUMENTS

| WO | WO 2010/127113 | 11/2010 |
|---|---|---|
| WO | WO 2010/127113 A2 | 11/2010 |
| WO | WO 2011/004028 | 1/2011 |
| WO | WO 2012/095432 A2 | 7/2012 |
| WO | WO 2013/178736 | 12/2013 |
| WO | WO 2014/052188 | 4/2014 |

OTHER PUBLICATIONS

Kobayashi et al. Protein Engineering; 1999; vol. 12, pp. 879-844.*
Brorson et al. J. Immunol; 1999; vol. 163, pp. 6694-6701.*
Coleman Research in Immunol; 1994; vol. 145; pp. 33-36.*
Akira, et al. 2004. Toll-like receptor signalling. *Nature Review Immunol.*, 4:499-511.
Albert, et al. 2004. Death-defying immunity: do apoptotic cells influence antigen processing and presentation? *Nat. Rev. Immunol.*, 4:223-231.
Alexoupoulou, et al. 2001. Recognition of double-stranded RNA and activation of NK-κB by Toll-like receptor 3. *Nature*, 413: 732-738.
Altschul et al. 1990. *J. Mol. Biol.*, 215, 403-410.
Antibody Purification Handbook, Biosciences, publication No. 18-1037-46, Edition AC, 2002.
Bell, et al. 2006. The dsRNA binding site of human Toll-like receptor 3. *Proc. Natl. Acad. Sci. USA*, 103(23):8792-8797.
Bokarewa, et al. 2008. Arthritogenic dsRNA is present in synovial fluid from rheumatoid arthritis patients with an erosive disease course. *European Journal of Immunology*, 38:3237-3244.
Botos, I. et al., "The Toll-like receptor 3:dsRNA signaling complex," BBA—Gene Regulatory Mechanisms (online), 1789(9-10):667-674, 2009.
Carrillo, et al. The multiple sequence alignment problem in biology. *SIAM J Appl Math.* 1988; 48:1073-1082.
Carter, et al. 1992. Humanization of an anti-p185$^{HER2}$ antibody for human cancer therapy. *Proc. Natl. Acad. Sci. USA*, 89:4285-4289.
Carter et al, *Cancer Journal*: May/Jun. 2008—vol. 14—Issue 3—pp. 154-169, Antibody-Drug Conjugates for Cancer Therapy.
Cavassani et al. (2008). TLR3 is an endogenous sensor of tissue necrosis during acute inflammatory events. *J. Exp. Med.* 205: 2609-2621.
Choe, et al. 2005. Crystal structure of human Toll-like receptor 3 (TLR3) ectodomain. *Science*, 309(5734):581-585.
Chothia, et al. (1987). Canonical structures for the hypervariable regions of immunoglobulins. *J. Mol. Biol.* 196, 901-917.
Clackson, et al. (1995) *Science* 267, 383-386. "A Hot Spot of Binding Energy in a Hormone-Receptor Interface."
Coligan, et al., eds., Current Protocols in Immunology, Greene Publishing Assoc., 1999.
deBouteiller, et al. 2005. Recognition of double-stranded RNA by human toll-like receptor 3 and downstream receptor signaling requires multimerization and an acidic pH. *The Journal of Biological Chemistry*, 280(46):38133-38145.
Delgado C, et al. Enhanced tumour specificity of an anti-carcinoembrionic antigen Fab' fragment by poly(ethylene glycol) (PEG) modification. *Br J Cancer.* Jan. 1996;73(2):175-182.
Devereux et al., A comprehensive set of sequence analysis programs for the VAX. *Nucl. Acid. Res.* 12, 387-395 (1984).
Doronina, et al. 2003. *Nat. Biotech.*, 21(7):778-784.
Downward, 2000. *J. Mass Spectrom.*, 35(4):493-503.
Duffy, et al., "Down modulation of human TLR3 function by a monoclonal antibody," Cellular Immunology, Academic Press, San Diego, CA, J.CELLIMM., 248(2):103-114, Dec. 26, 2007.
Ehring, H. 1999. Analytical Biochemistry, 267(2);252-259.
Enger, et al. 2001. *Anal. Chem.*, 73:256A-265A.
Ernst Schering Res Found Workshop. 2004; (44): 149-67.
Fägerstam, et al., Journal of Molecular Recognition 1990;3:208-14.
Francisco, et al., Neoplasia, 102(4):1458-1465, Aug. 15, 2003.
Goding, "Monoclonal Antibodies: Principles and Practice," pp. 59-103 (Academic Press, 1986).

Green, L.L. et al. Antigen-specific human monoclonal antibodies from mice engineered with human Ig heavy and light chain YACs. *Nature Genet.* 7, 13-21 (1994).
Gribskov, M. Sequence Analysis Primer, M. Stockton Press, New York, 1991.
Griffin, Annette M. et al., Computer Analysis of Sequence Data, Part 1, Humana Press, New Jersey, 1994.
Guex, et al. .2007. Electrophoresis, 18:2714-2723.
Hamblett et al., (2004) Effects of Drug Loading on the Antitumor Activity of a Monoclonal Antibody Drug Conjugate, *Clin Canc Res*, 10:7063-7070.
Harlow, E. and D. Lane, Antibodies: A Laboratory Manual., Cold Spring Harbor Laboratory Press, Cold Spring Harbor, NY (1988).
Hacker, H., et al. 1999. *EMBO J.* 18:6973-6982.
Huang, et al. 1998. *Journal of Molecular Biology*, 281(1):61-67.
Jakobovitz, et al. 1993. *Nature*, 362:255.
Jones, et al. 1986. *Nature*, 321:522.
Kabat, et al. (1991) Sequences of Protein of Immunological Interest, 5th ed., United States Public Health Service, National Institute of Health, Bethesda, MD.
Karikó, et al. 2004. mRNA is an endogenous ligand for toll-like receptor 3. *The Journal of Biological Chemistry*, 279(13):12542-12550.
Kim, et al. (2009) Immunol. Lett. report that TLR3 promotes osteoclastogenesis in the RA synovium both directly and indirectly by stimulating human monocytes directly to promote osteoclast differentiation and by inducing RANKL expression indirectly in RA-FLS.
Kiselar, et al. 1999. *Anal Chem.*, 71(9):1792-1801.
Kröger, et al., *Biosensors and Bioelectronics*, 2002; 17:937-944.
Lang, et al. 2006. *J. Clin. Invest.*, 116:2456-2463.
Law et al., *Clin Canc Res*, 10:7842-7851, Dec. 1, 2004.
Leipert, et al. 1998. Angew. Chem. Int. Ed. 1998; 37:3308-3311.
Leong Sr, et al. Adapting pharmacokinetic properties of a humanized anti-interleukin-8 antibody for therapeutic applications using site-specific pegylation. *Cytokine* 2001, 16:106-119.
Lesk, Arthur M., Computational Molecular Biology, Oxford University Press, New York, 1988.
Lonberg, et al. Antigen-specific human antibodies from mice comprising four distinct genetic modifications. *Nature* 368, 856-859 (1994).
Manca, Ann 1st Super Sanita. 1991; 27:15-19.
Matsumoto, et al. 2003. *J. Immunol.*, 171:3154-3162.
McCafferty, et al. 1990. *Nature*, 348:552-553.
Morrison, et al., 1984. Chimeric human antibody molecules: Mouse antigen-binding domains with human constant region domains. *Proc. Natl. Acad. Sci. USA*, 81:6851-6855.
Muller, 1983. *Meth. Enzymol.*, 92:589-601.
Murphy, et al. 1995. *Mol Cell Biol*, 15:5258-5267.
NCBI accession No. NP_003256. Retrieved May 24, 2011, from http://www.ncbi.nlm.nih.gov/protein/NP_003256, Yamashita al.
NCBI accession No. NM_003265. Retrieved May 24, 2011, from http://www.ncbi.nlm.nih.gov/nuccore/NM_003265, Yamashita et al.
Nice, et al., J. Chroma-togr. 1993; 646:159-168.
Pluckthun, 1992. *Immunol.*, 130, p. 151.
Presta, 1992. *Curr. Op. Struct. Biol.*, 2, pp. 593.
Presta, et al., J. Immunol., 51, p. 1993.
Rahman AH, Eisenberg RA: The role of toll-like receptors in systemic lupus erythematosus. Springer Semin Immunopathol 28:131, 2006.
Ranjith-Kumar, et al. 2007. Biochemical and functional analyses of the human Toll-like receptor 3 ectodomain. *Journal of Biological Chemistry*, 282(10):7668-7678.
Ravi, et al, Accounts of Chemical Research 98-107 Jan. 2008 vol. 41, No. 1.
Reichmann, et al. 1988. *Nature*, 332, pp. 323.
Sanderson et al., *Clin Canc Res*, 11:843-852, Jan. 15, 2005.
Sacre, et al. 2008. *J. Immunol.*, 181:8002-8009.
Saito, et al. 1996. *Methods*; 9(3):516-524.
Saunal. 1995. *J. Immunol. Methods*, 183:33-41.
Sims, et al. 1993. *J. Immunol.*, 151, pp. 2296.
Skerra, et al., Curr. Opinion in Immunol., 5, pp. 256 (1993).

(56) References Cited

OTHER PUBLICATIONS

Smith, D.W., Biocomputing: Informatics and Genome Projects, Academic Press, New York, 1993.
Song, et al. Characterization of a novel anti-human TNF-alpha murine monoclonal antibody with high binding affinity and neutralizing activity. *Exp Mol Med.* 2008;40:35-42.
Sun, et al. 2006. Structural and functional analyses of the human toll-like receptor 3: Role of glycosylation. *The Journal of Biological Chemistry*, 281(16):11144-11151.
Takada, E., et al. 2007. C-terminal LRRs of human Toll-like receptor 3 control receptor dimerization and signal transmission. *Molecular Immunology*, 44(15):3633-3640.
Taylor, L. D. et al. Human immunoglobulin transgenes undergo rearrangement, somatic mutation and class switching in mice that lack endogenous IgM. *Int. Immunol.* 6(4):579-591 (1994).
Verhoeyen, et al. Reshaping human antibodies: Grafting an antilysozyme activity. *Science* (1988) 239: 1534-1536.
Von Heinje, G., Sequence Analysis in Molecular Biology, Academic Press, 1987.
Wang et al., Identification of a Fab interaction footprint site on an icosahedral virus by cryoelectron microscopy and X-ray crystallography, *Nature*, 1992; 355:275-278.
Ward et al. Binding activities of a repertoire of single immunoglobulin variable domains secreted from *Escherichia coli*, *Nature*, 341 (1989) p. 544-546.
Wells, J. A. 1996. Binding in the growth hormone receptor complex. *Proc. Natl. Acad. Sci. USA*, 93:1-6.
Wen, et al. (2004) J. Immunol. 172: 3172-3180.
Wietek, et al. 2003. Interferon regulatory factor-3-mediated activation of the interferon-sensitive response element by toll-like receptor (TLR) 4 but not TLR3 requires the p65 subunit of NF-κB. *The Journal of Biological Chemistry*, 278(51):50923-50931.
Zorde-Khvalevsky et al. (2009) Hepatology 49[Article first published online: Mar. 19, 2009][Toll-like receptor 3 signaling attenuates liver regeneration, 50(1):198-206, Jul. 2009.
International Search Report for PCT/EP2010/059946 mailed Mar. 30, 2011.
U.S. Appl. No. 61/109,974, filed Oct. 31, 2008.
U.S. Appl. No. 61/161,860, filed Mar. 20, 2009.
U.S. Appl. No. 61/165,100, filed Mar. 31, 2009.
U.S. Appl. No. 61/173,686, filed Apr. 29, 2009.
NCBI accession No. BAG55033; toll-like receptor 3; Dec. 5, 2008; 2 pages.
International Search Report for PCT/EP2013/061173 mailed Sep. 4, 2013.
International Preliminary Report on Patentability and Written Opinion for PCT/EP2013/061173 mailed Dec. 2, 2014.
U.S. Office Action dated Dec. 1, 2011 in U.S. Appl. No. 12/609,675, filed Oct. 30, 2009.
U.S. Response dated Feb. 1, 2012 in U.S. Appl. No. 12/609,675, filed Oct. 30, 2009.
U.S. Office Action dated Apr. 11, 2012 in U.S. Appl. No. 12/609,675, filed Oct. 30, 2009.
U.S. Response dated Aug. 8, 2012 in U.S. Appl. No. 12/609,675, filed Oct. 30, 2009.
U.S. Notice of Allowance dated Oct. 29, 2012 in U.S. Appl. No. 12/609,675, filed Oct. 30, 2009.
U.S. Office Action dated Mar. 19, 2012 in U.S. Appl. No. 12/770,147, filed Apr. 29, 2010.
U.S. Response dated Apr. 19, 2012 in U.S. Appl. No. 12/770,147, filed Apr. 29, 2010.
U.S. Office Action dated May 31, 2012 in U.S. Appl. No. 12/770,147, filed Apr. 29, 2010.
U.S. Response dated Oct. 26, 2012 in U.S. Appl. No. 12/770,147, filed Apr. 29, 2010.
U.S. Office Action dated Nov. 2, 2012 in U.S. Appl. No. 12/770,147, filed Apr. 29, 2010.
U.S. Response dated Nov. 30, 2012 in U.S. Appl. No. 12/770,147, filed Apr. 29, 2010.
U.S. Notice of Allowance dated Feb. 1, 2013 in U.S. Appl. No. 12/770,147, filed Apr. 29, 2010.
U.S. Response/RCE dated Apr. 30, 2013 in U.S. Appl. No. 12/770,147, filed Apr. 29, 2010.
U.S. Notice of Allowance dated May 21, 2013 in U.S. Appl. No. 12/770,147, filed Apr. 29, 2010.
U.S. Office Action dated Sep. 26, 2012 in U.S. Appl. No. 13/230,060, filed Sep. 12, 2011.
U.S. Response dated Dec. 20, 2012 in U.S. Appl. No. 13/230,060, filed Sep. 12, 2011.
U.S. Notice of Allowance dated Feb. 6, 2013 in U.S. Appl. No. 13/230,060, filed Sep. 12, 2011.
U.S. Response (312) dated May 2, 2013 in U.S. Appl. No. 13/230,060, filed Sep. 12, 2011.
U.S. Office Action dated Jan. 3, 2014 in U.S. Appl. No. 13/628,434, filed Sep. 27, 2012.
U.S. Notice of Abandonment dated Jul. 31, 2014 in U.S. Appl. No. 13/628,434, filed Sep. 27, 2012.
U.S. Office Action dated Mar. 31, 2014 in U.S. Appl. No. 13/751,718, filed Jan. 28, 2013.
U.S. Response dated May 29, 2014 in U.S. Appl. No. 13/751,718, filed Jan. 28, 2013.
U.S. Office Action dated Aug. 6, 2014 in U.S. Appl. No. 13/751,718, filed Jan. 28, 2013.
U.S. Response dated Dec. 5, 2014 in U.S. Appl. No. 13/751,718, filed Jan. 28, 2013.
U.S. Office Action dated Dec. 5, 2013 in U.S. Appl. No. 13/887,797, filed May 06, 2013.
U.S. Notice of Abandonment dated Jul. 3, 2014 in U.S. Appl. No. 13/887,797, filed May 06, 2013.
U.S. Office Action dated Apr. 24, 2014 in U.S. Appl. No. 13/777,513, filed Feb. 26, 2013.
U.S. Response dated Jun. 23, 2014 in U.S. Appl. No. 13/777,513, filed Feb. 26, 2013.
U.S. Office Action dated Aug. 28, 2014 in U.S. Appl. No. 13/777,513, filed Feb. 26, 2013.
U.S. Response dated Nov. 26, 2014 in U.S. Appl. No. 13/777,513, filed Feb. 26, 2013.
U.S. Notice of Allowance dated Jan. 13, 2015 in U.S. Appl. No. 13/777,513, filed Feb. 26, 2013.
U.S. Office Action dated May 22, 2014 in U.S. Appl. No. 13/798,494, filed Mar. 13, 2013.
U.S. Response dated Jul. 22, 2014 in U.S. Appl. No. 13/798,494, filed Mar. 13, 2013.
U.S. Office Action dated Sep. 29, 2014 in U.S. Appl. No. 13/798,494, filed Mar. 13, 2013.
U.S. Response dated Dec. 29, 2014 in U.S. Appl. No. 13/798,494, filed Mar. 13, 2013.
U.S. Appl. No. 61/224,548, filed Jul. 10, 2009.
International Search Report for PCT/US2013/060886 mailed Dec. 13, 2013.
Alamanos et al., (2005) "Epidemiology of adult rheumatoid arthritis", *Autoimmun Rev.* 4(3):130-136.
Amersham Biosciences, (2002) "Antibody Purification Handbook", Publication No. 18-1037-46, Edition AC; 112 pages.
Andersen et al., (2010 online) "Structural characterization of both the non-proteolytic and proteolytic activation pathways of coagulation Factor XIII studied by hydrogen-deuterium exchange mass spectrometry"; *Int J Mass Spectro.* 302(1-3):139-148.
Angal et al., (1993) "A single amino acid substitution abolishes the heterogeneity of chimeric mouse/human (IgG4) antibody" *Molecular Immunology*, 30(1):105-108.
Avis et al., Pharmaceutical Dosage Forms: Parenteral Medications, Dekker, New York, (1993), vol. 1, 2, and 3.
Barnes, et al. (2009) "The Cytokine Network in Chronic Obstructive Pulmonary Disease", *Am J Respir Cell Mol Biol.* 41: 631-638.
Bukhari et al. (2002) "Rheumatoid factor is the major predictor of increasing severity of radiographic erosions in rheumatoid arthritis: Results from the Norfolk Arthritis Register Study, a large inception cohort." *Arthritis Rheum.*, 46(4): 906-912.
Bunting, et al. (2011) "Novel antagonist antibody to TLR3 blocks poly(I:C)-induced inflammation in vivo and in vitro", Cellular Immunol v267 (1).

(56) References Cited

OTHER PUBLICATIONS

Chari, Ravi V.J., (2008) "Targeted Cancer Therapy: Conferring Specificity to Cytotoxic Drugs", Accounts of Chemical Research Jan. 2008 41(1):98-107.
Gabriel, (2001) "The epidemiology of rheumatoid arthritis." *Rheum. Dis. Clin North Am.* 27(2):269-281.
Gennaro, ed., (1990) Remington's Pharmaceutical Sciences, 18th ed., Mack Publishing Co., Easton, PA—Cover and Table of Contents; pp. 5.
Goodman & Gilman's, (1990)The Pharmacological Bases of Therapeutics, 7th ed., Pergamon Press—Cover and Table of Contents; pp. 8.
Heliövaara et al., (1995) "Rheumatoid factor, chronic arthritis and mortality", *Ann. Rheum. Dis.*, 54: 811-814.
Hulsmans et al., (2000) "The Course of Radiologic Damage During the First Six Years of Rheumatoid Arthritis", *Arthritis Rheum.*, 43(9): 1927-1940.
International Preliminary Report on Patentability and Written Opinion for PCT/EP2010/059946 mailed Jan. 10, 2012.
International Preliminary Report on Patentability and Written Opinion for PCT/EP2012/050321 mailed Jul. 16, 2013.
International Search Report for PCT/EP2012/050321 mailed Jul. 25, 2012.
Jinquan Luo et al, (2012) "Lateral Clustering of TLR3:dsRNA Signaling Units Revealed by TLR3ecd:3Fabs Quaternary Structure", Journal of Molecular Biology, 421(1): 112-124.
Jinquan Luo et al, (2012) Supplementary information to Lateral Clustering of TLR3:dsRNA Signaling Units Revealed by TLR3ecd:3Fabs structure.
Keystone, (2005) "B cells in rheumatoid arthritis: from hypothesis to the clinic", *Rheumatology*, 44 (Suppl. 2): ii8-ii12.
Lieberman et al., Pharmaceutical Dosage Forms: Disperse Systems Dekker, New York (1990).
McDonald et al., (2001) "Recommended diagnostic criteria for multiple sclerosis: guidelines from the International Panel on the diagnosis of multiple sclerosis" *Ann. Neurol.* 50(1): 121-7.
Meng et al., (2010) "Toll-like receptor 3 upregulation in macrophages participates in the initiation and maintenance of pristine-induced arthritis in rats", *Arth Res Thera.* 12(3): R103; 12 pages.
Meyer, et al. (2004) "Saturation transfer difference NMR spectroscopy for identifying ligand epitopes and binding specificities" Ernst Schering Res Found Workshop. 44:149-67.
Nakamura et al., (2008) "Increased expression of Toll-like receptor 3 in intrahepatic biliary epithelial cells at sites of ductular reaction in diseased livers", *Hepatology International*, 2(2): 222-230.
NCBI accession No. NP_612564; http://www.ncbi.nlm.nih.gov/protein/NP_612564, Feb. 9, 2014
O'Connor et al., (2011) "Comparison of Arterial and Venous Blood Gases and the Effects of Analysis Delay and Air Contamination on Arterial Samples in Patients with Chronic Obstructive Pulmonary Disease and Healthy Controls", Respiration, 81: 18-25.
O'Dell, (2004) "Drug therapy: therapeutic strategies for rheumatoid arthritis." *New Engl. J. Med.* 350:2591-2602.
Paradowska et al. (2006) "Review Paper: Pro-inflammatory cytokines gene polymorphisms in Rheumatoid Arthritis" *Centr Eur J Immunol.*, 31(3-4): 117-122.
Pariente et al., (2011) "Development of the Crohn's Disease Digestive Damage score, the Lémann score"; *Inflamm Bowel Dis*; 17:6, 1415-1422 [avail. Online Nov. 28, 2010].
Paulus et al. (1996) "Monitoring radiographic changes in early rheumatoid arthritis" *J. Rheumatol.*, 23: 801-805.
Sandborn et al. (2002) "A review of activity indices and efficacy endpoints for clinical trials of medical therapy for adults with Crohn's disease" *Gastroenterology*, 122(2):512-530.
Scott et al., (2000) "The links between joint damage and disability in rheumatoid arthritis", *Rheumatology* 39:122-132.
Takii et al., (2005) "Enhanced expression of type I interferon and toll-like receptor-3 in primary biliary cirrhosis", *Laboratory Investigation*, 85(7):908-920.
U.S. Appl. No. 61/670,289, filed Jul. 11, 2012.
U.S. Appl. No. 61/653,652, filed May 31, 2012.
U.S. Appl. No. 61/679,923, filed Aug. 6, 2012.
Wales, et al., (2006) "Hydrogen exchange mass spectrometry for the analysis of protein dynamics", Mass Spectrom. Rev. 25, 158.
Walters, ed. (2002) Dermatological and transdermal formulations (drugs and the pharmaceutical sciences), vol. 119, Dekker, New York.
Weis, et al., (2006) "Semi-Automated Data Processing of Hydrogen Exchange Mass Spectra Using *HX-Express*", *J Am Soc Mass Spectrom.* 17:1700.
Yin et al. (2010) "Toll-Like Receptor 3 in Liver Diseases" *Gastroenterology Research and Practice Article* ID 750904; 2010:1-6.
"Submission Regarding Experimental Results", May 19, 2015, 5 pages.
Datasheet MCA2267; AbD Serotec, from Table A of Submission Regarding Experimental Results, "Mouse Anti Human CD283", commercially available prior to Sep. 2008, printed Apr. 23, 2015; 3 pages.
Datasheet N-14; Santa Cruz Biotechnology, Inc from Table A of Submission Regarding Experimental Results, "TLR3 (N-14): sc-8691", commerically available prior to Sep. 2008, archived Aug. 2010; 1 page.
Datasheet Q-18; Santa Cruz Biotechnology, Inc. from Table A of Submission Regarding Experimental Results, TLR3 (Q-18): sc-12509, commercially available prior to Sep. 2008, archived Aug. 2010; 1 page.
Datasheet; R&D Systems, from Table A of Submission Regarding Experimental Results, "Polyclonal Goat IgG—Mouse TLR3 Antibody", Rev. Mar. 13, 2015, commercially available prior to Sep. 2008, Catalog #AF3005; 1 page.
Datasheet TLR3-7; Affymetrix eBioscience, from Table A of Submission Regarding Experimental Results, "Anti-Human CD283 (TLR3) Purified", TLR3-7, Catalog #14-9039, commercially available prior to Sep. 2008; 2 pages.
Datasheet 40C1285; Imgenex, from Table A of Submission Regarding Experimental Results, "TLR3 Antibody-NBP2-24875", commercially available prior to Sep. 2008, Updated Mar. 1, 2015; 5 pages.
Datasheet A01; ABNOVA, from Table A of Submission Regarding Experimental Results, TLR3 polyclonal antibody, commercially available prior to Sep. 2008, 1 page.
Datasheet L-13; Santa Cruz Biotechnology, Inc. from Table A of Submission Regarding Experimental Results, TLR3 (L-13): sc-16238, commercially available prior to Sep. 2008, 1 page.
Datasheet C-20; Santa Cruz Biotechnology, Inc. from Table A of Submission Regarding Experimental Results, TLR3 (C-20): se-8692, commercially available prior to Sep. 2008, 1 page.
Datasheet H-125; Santa Cruz Biotechnology, Inc. from Table A of Submission Regarding Experimental Results, TLR3 (H-125): sc-10740, commercially available prior to Sep. 2008, 1 page.
Kimura et al., "Toll-like receptor 3 stimulation causes corticosteroid-refractory airway neutrophilia and hyperresponsiveness in mice", Chest (Jul. 2013) 144(1): 99-105.
Kizawa et al., "Possible involvement of TLR3 pathway on corticosteroid refractory airway inflammation in mice", 83rd Annual Meeting of the Japanese-Pharmacological-Society, Mar. 1, 2010, p. 205P.
Morel, Y., "Blocking Anti-TLR3 mAb for Inflammation—Molecular Pattern Recognition Receptors", Apr. 11-12, 2013; online at URL:http://innate-pharma.com/sites/default/files/iph33_mprr_conference_2013_0,pdf; 30 pages.
Rossios et al., "TLR3 Activation Causes Corticosteroid Insensitivity in Human Bronchial Epithelial Cells", American Thoracic Society Inter'l Conference. May 9, 2013; Meeting Abstract #2394, Online at URL:http://atsjournals.org/doi/abs/10.1164/ajrcem-conference.2013.187.1_MeetingAbstracts.A2394.
Chinese Office Action dated Jul. 2, 2013 for Application No. 201080030919.5.
International Search Report dated Aug. 7, 2014 for PCT/EP2014/059773, filed May 13, 2014.
U.S. Office Action dated Feb. 20, 2015 in U.S. Appl. No. 13/751,718, filed Jan. 28, 2013.
U.S. 2nd Notice of Allowance dated Apr. 27, 2015 in U.S. Appl. No. 13/777,513, filed Feb. 26, 2013.

(56) References Cited

OTHER PUBLICATIONS

U.S. Notice of Allowance dated Mar. 11, 2015 in U.S. Appl. No. 13/798,494, filed Mar. 13, 2013.
U.S. 2nd Notice of Allowance dated Apr. 23, 2015 in U.S. Appl. No. 13/798,494, filed Mar. 13, 2013.
U.S. Office Action dated Jan. 29, 2015 in U.S. Appl. No. 13/973,187, filed Aug. 22, 2013.
U.S. Response dated Mar. 30, 2015 in U.S. Appl. No. 13/973,187, filed Aug. 22, 2013.
"Submission Regarding Experimental Results", Jun. 8, 2015, 5 pages; filed in U.S. Appl. No. 13/979,370 on Jun. 8, 2015.
"Submission Regarding Experimental Results", Jun. 8, 2015, 5 pages; filed in U.S. Appl. No. 14/403,171 on Jun. 8, 2015.
Housset et al., "The three-dimensional structure of a T-cell antigen receptor ValphaVbeta heterodimer reveals a novel arrangement of the Vbeta domain", EMBO J., (1997) 16(14):4205-4216.
Mayo Clinic, "Diseases and Conditions: Ischemic Colitis", Oct. 10, 2012 downlaoded from http://www.mayoclinic.org/diseases-conditions/ischemic-colitis/basics/causes/con-20026677?p=1; 6 pages.
National Institute of Health, "Asthma", downloaded Jan. 20, 2012 from www.nhlbi.nih.gov/health/health-topics/topics/asthma/; 2 pages.
National Institute of Health, "Graft Versus Host Disease (GVHD): A Guide for Patients and Families after Stem Cell Transplant", 2007; 3 pages.
Schuermann et al., "Structure of an anti-DNA Fab Complexed with a Non-DNA Ligand Provides Insights into Cross-Reactivity and Molecular Mimicry", Proteins: Structure, Function, and Bioinformatics (2004) 57:269-278.

U.S. Office Action dated Jun. 9, 2015 in U.S. Appl. No. 13/979,370, filed Nov. 19, 2013.
U.S. Response dated Aug. 10, 2015 in U.S. Appl. No. 13/979,370, filed Nov. 19, 2013.
U.S. Office Action dated Dec. 17, 2015 in U.S. Appl. No. 13/979,370, filed Nov. 19. 2013.
U.S. Response dated May 20, 2015 in U.S. Appl. No. 13/751,718, filed Jan. 28, 2013.
U.S. Office Action Dated Jun. 2, 2015 in U.S. Appl. No. 13/751,718, filed Jan. 28, 2013.
U.S. Response dated Oct. 1, 2015 in U.S. Appl. No. 13/751,718, filed Jan. 28, 2013.
U.S. 3nd Notice of Allowance dated Aug. 27, 2015 in U.S. Appl. No. 13/777,513, filed Feb. 26, 2013.
U.S. 3rd Notice of Allowance dated Sep. 14, 2015 in U.S. Appl. No. 13/798,494, filed Mar. 13, 2013.
U.S. Office Action dated May 27, 2015 in U.S. Appl. No. 13/973,187, filed Aug. 22, 2013.
U S. Response dated Sep. 25, 2015 in U.S. Appl. No. 13/973,187, filed Aug. 22, 2013.
U.S. Notice of Allowance dated Jan. 6, 2016 in U.S. Appl. No. 13/973,187, filed Aug. 22, 2013.
U.S. Response dated Mar. 15, 2016 in U.S. Appl. No. 13/979,370, filed Nov. 19, 2013.
U.S. Office Action dated Jan. 25, 2016 in U.S Appl. No. 13/751,718, filed Jan. 28, 2013.
U.S. Response dated Apr. 5, 2016 in U.S. Appl. No. 13/973,187, filed Aug. 22, 2013.
U.S. Notice of Allowance dated Apr. 18, 2016 in U.S. Appl. No. 13/973,187, filed Aug. 22, 2013.

\* cited by examiner

SEQUENCE LISTING

```
<160> NUMBER OF SEQ ID NOS: 85

<210> SEQ ID NO 1
<211> LENGTH: 904
<212> TYPE: PRT
<213> ORGANISM: homo sapiens

<400> SEQUENCE: 1

Met Arg Gln Thr Leu Pro Cys Ile Tyr Phe Trp Gly Leu Leu Pro
1               5                   10                  15

Phe Gly Met Leu Cys Ala Ser Ser Thr Thr Lys Cys Thr Val Ser His
                20                  25                  30

Glu Val Ala Asp Cys Ser His Leu Lys Leu Thr Gln Val Pro Asp Asp
                35                  40                  45

Leu Pro Thr Asn Ile Thr Val Leu Asn Leu Thr His Asn Gln Leu Arg
        50                  55                  60

Arg Leu Pro Ala Ala Asn Phe Thr Arg Tyr Ser Gln Leu Thr Ser Leu
65                  70                  75                  80

Asp Val Gly Phe Asn Thr Ile Ser Lys Leu Glu Pro Glu Leu Cys Gln
                85                  90                  95

Lys Leu Pro Met Leu Lys Val Leu Asn Leu Gln His Asn Glu Leu Ser
                100                 105                 110

Gln Leu Ser Asp Lys Thr Phe Ala Phe Cys Thr Asn Leu Thr Glu Leu
            115                 120                 125

His Leu Met Ser Asn Ser Ile Gln Lys Ile Lys Asn Asn Pro Phe Val
        130                 135                 140

Lys Gln Lys Asn Leu Ile Thr Leu Asp Leu Ser His Asn Gly Leu Ser
145                 150                 155                 160

Ser Thr Lys Leu Gly Thr Gln Val Gln Leu Glu Asn Leu Gln Glu Leu
                165                 170                 175

Leu Leu Ser Asn Asn Lys Ile Gln Ala Leu Lys Ser Glu Glu Leu Asp
                180                 185                 190

Ile Phe Ala Asn Ser Ser Leu Lys Lys Leu Glu Leu Ser Ser Asn Gln
            195                 200                 205

Ile Lys Glu Phe Ser Pro Gly Cys Phe His Ala Ile Gly Arg Leu Phe
        210                 215                 220

Gly Leu Phe Leu Asn Asn Val Gln Leu Gly Pro Ser Leu Thr Glu Lys
225                 230                 235                 240

Leu Cys Leu Glu Leu Ala Asn Thr Ser Ile Arg Asn Leu Ser Leu Ser
                245                 250                 255

Asn Ser Gln Leu Ser Thr Thr Ser Asn Thr Thr Phe Leu Gly Leu Lys
                260                 265                 270

Trp Thr Asn Leu Thr Met Leu Asp Leu Ser Tyr Asn Asn Leu Asn Val
            275                 280                 285

Val Gly Asn Asp Ser Phe Ala Trp Leu Pro Gln Leu Glu Tyr Phe Phe
        290                 295                 300
```

```
Leu Glu Tyr Asn Asn Ile Gln His Leu Phe Ser His Ser Leu His Gly
305                 310                 315                 320

Leu Phe Asn Val Arg Tyr Leu Asn Leu Lys Arg Ser Phe Thr Lys Gln
            325                 330                 335

Ser Ile Ser Leu Ala Ser Leu Pro Lys Ile Asp Asp Phe Ser Phe Gln
        340                 345                 350

Trp Leu Lys Cys Leu Glu His Leu Asn Met Glu Asp Asn Asp Ile Pro
            355                 360                 365

Gly Ile Lys Ser Asn Met Phe Thr Gly Leu Ile Asn Leu Lys Tyr Leu
        370                 375                 380

Ser Leu Ser Asn Ser Phe Thr Ser Leu Arg Thr Leu Thr Asn Glu Thr
385                 390                 395                 400

Phe Val Ser Leu Ala His Ser Pro Leu His Ile Leu Asn Leu Thr Lys
                405                 410                 415

Asn Lys Ile Ser Lys Ile Glu Ser Asp Ala Phe Ser Trp Leu Gly His
            420                 425                 430

Leu Glu Val Leu Asp Leu Gly Leu Asn Glu Ile Gly Gln Glu Leu Thr
            435                 440                 445

Gly Gln Glu Trp Arg Gly Leu Glu Asn Ile Phe Glu Ile Tyr Leu Ser
450                 455                 460

Tyr Asn Lys Tyr Leu Gln Leu Thr Arg Asn Ser Phe Ala Leu Val Pro
465                 470                 475                 480

Ser Leu Gln Arg Leu Met Leu Arg Arg Val Ala Leu Lys Asn Val Asp
            485                 490                 495

Ser Ser Pro Ser Pro Phe Gln Pro Leu Arg Asn Leu Thr Ile Leu Asp
        500                 505                 510

Leu Ser Asn Asn Asn Ile Ala Asn Ile Asn Asp Asp Met Leu Glu Gly
            515                 520                 525

Leu Glu Lys Leu Glu Ile Leu Asp Leu Gln His Asn Asn Leu Ala Arg
530                 535                 540

Leu Trp Lys His Ala Asn Pro Gly Gly Pro Ile Tyr Phe Leu Lys Gly
545                 550                 555                 560

Leu Ser His Leu His Ile Leu Asn Leu Glu Ser Asn Gly Phe Asp Glu
            565                 570                 575

Ile Pro Val Glu Val Phe Lys Asp Leu Phe Glu Leu Lys Ile Ile Asp
            580                 585                 590

Leu Gly Leu Asn Asn Leu Asn Thr Leu Pro Ala Ser Val Phe Asn Asn
            595                 600                 605

Gln Val Ser Leu Lys Ser Leu Asn Leu Gln Lys Asn Leu Ile Thr Ser
            610                 615                 620

Val Glu Lys Lys Val Phe Gly Pro Ala Phe Arg Asn Leu Thr Glu Leu
625                 630                 635                 640

Asp Met Arg Phe Asn Pro Phe Asp Cys Thr Cys Glu Ser Ile Ala Trp
                645                 650                 655

Phe Val Asn Trp Ile Asn Glu Thr His Thr Asn Ile Pro Glu Leu Ser
            660                 665                 670

Ser His Tyr Leu Cys Asn Thr Pro Pro His Tyr His Gly Phe Pro Val
            675                 680                 685

Arg Leu Phe Asp Thr Ser Ser Cys Lys Asp Ser Ala Pro Phe Glu Leu
            690                 695                 700

Phe Phe Met Ile Asn Thr Ser Ile Leu Leu Ile Phe Ile Phe Ile Val
705                 710                 715                 720
```

Leu Leu Ile His Phe Glu Gly Trp Arg Ile Ser Phe Tyr Trp Asn Val
            725                 730                 735

Ser Val His Arg Val Leu Gly Phe Lys Glu Ile Asp Arg Gln Thr Glu
        740                 745                 750

Gln Phe Glu Tyr Ala Ala Tyr Ile Ile His Ala Tyr Lys Asp Lys Asp
            755                 760                 765

Trp Val Trp Glu His Phe Ser Ser Met Glu Lys Glu Asp Gln Ser Leu
    770                 775                 780

Lys Phe Cys Leu Glu Glu Arg Asp Phe Glu Ala Gly Val Phe Glu Leu
785                 790                 795                 800

Glu Ala Ile Val Asn Ser Ile Lys Arg Ser Arg Lys Ile Ile Phe Val
                805                 810                 815

Ile Thr His His Leu Leu Lys Asp Pro Leu Cys Lys Arg Phe Lys Val
            820                 825                 830

His His Ala Val Gln Gln Ala Ile Glu Gln Asn Leu Asp Ser Ile Ile
            835                 840                 845

Leu Val Phe Leu Glu Glu Ile Pro Asp Tyr Lys Leu Asn His Ala Leu
        850                 855                 860

Cys Leu Arg Arg Gly Met Phe Lys Ser His Cys Ile Leu Asn Trp Pro
865                 870                 875                 880

Val Gln Lys Glu Arg Ile Gly Ala Phe Arg His Lys Leu Gln Val Ala
                885                 890                 895

Leu Gly Ser Lys Asn Ser Val His
            900

<210> SEQ ID NO 2
<211> LENGTH: 136
<212> TYPE: PRT
<213> ORGANISM: Mus musculus
<220> FEATURE:
<221> NAME/KEY: SIGNAL
<222> LOCATION: (1)..(19)

<400> SEQUENCE: 2

Met Gly Trp Ser Trp Ile Phe Leu Phe Leu Leu Ser Gly Thr Ala Gly
1               5                   10                  15

Val Leu Ser Glu Val Gln Leu Gln Gln Ser Gly Pro Glu Leu Val Lys
            20                  25                  30

Pro Gly Ala Ser Val Lys Ile Ser Cys Lys Pro Ser Gly Tyr Ser Phe
        35                  40                  45

Thr Ala Tyr Tyr Met His Trp Val Lys Gln Ser His Val Lys Ser Leu
    50                  55                  60

Glu Trp Ile Gly Arg Ile Asn Pro Tyr Asn Gly Ala Thr Ser Tyr Asn
65                  70                  75                  80

Arg Asn Phe Lys Asp Lys Ala Ser Leu Thr Val Asp Lys Ser Ser Ser
                85                  90                  95

Thr Ala Tyr Met Glu Leu His Ser Leu Thr Ser Glu Asp Ser Ala Val
            100                 105                 110

Tyr Tyr Cys Ala Arg Ser Gly Gly Asn Thr Tyr Phe Asp Tyr Trp Gly
        115                 120                 125

Gln Gly Thr Thr Leu Thr Val Ser
    130                 135

<210> SEQ ID NO 3
<211> LENGTH: 127
<212> TYPE: PRT

-continued

```
<213> ORGANISM: Mus musculus
<220> FEATURE:
<221> NAME/KEY: SIGNAL
<222> LOCATION: (1)..(20)
<220> FEATURE:
<221> NAME/KEY: VARIANT
<222> LOCATION: (91)..(91)
<223> OTHER INFORMATION: Xaa = Phe or Ser

<400> SEQUENCE: 3

Met Ser Val Pro Thr Gln Val Leu Gly Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Ala Ser Glu Asn
        35                  40                  45

Ile Tyr Ser Ser Leu Ala Trp Tyr Gln Gln Lys Gln Gly Lys Ser Pro
    50                  55                  60

Gln Leu Leu Val Tyr Asn Ala Lys Thr Leu Ala Glu Gly Val Pro Ser
65                  70                  75                  80

Arg Phe Ser Gly Ser Gly Ser Gly Thr Gln Xaa Ser Leu Lys Ile Asn
                85                  90                  95

Ser Leu Gln Pro Glu Asp Phe Gly Thr Tyr Tyr Cys Gln His His Tyr
            100                 105                 110

Gly Thr Pro Pro Thr Phe Gly Gly Thr Lys Leu Glu Ile Lys
        115                 120                 125

<210> SEQ ID NO 4
<211> LENGTH: 9
<212> TYPE: PRT
<213> ORGANISM: Mus musculus

<400> SEQUENCE: 4

Gly Tyr Ser Phe Thr Ala Tyr Tyr Met
1               5

<210> SEQ ID NO 5
<211> LENGTH: 10
<212> TYPE: PRT
<213> ORGANISM: Mus musculus

<400> SEQUENCE: 5

Arg Ile Asn Pro Tyr Asn Gly Ala Thr Ser
1               5                   10

<210> SEQ ID NO 6
<211> LENGTH: 9
<212> TYPE: PRT
<213> ORGANISM: Mus musculus

<400> SEQUENCE: 6

Ser Gly Gly Asn Thr Tyr Phe Asp Tyr
1               5

<210> SEQ ID NO 7
<211> LENGTH: 10
<212> TYPE: PRT
<213> ORGANISM: Mus musculus

<400> SEQUENCE: 7

Arg Ala Ser Glu Asn Ile Tyr Ser Ser Leu
1               5                   10
```

```
<210> SEQ ID NO 8
<211> LENGTH: 7
<212> TYPE: PRT
<213> ORGANISM: Mus musculus

<400> SEQUENCE: 8

Asn Ala Lys Thr Leu Ala Glu
1               5

<210> SEQ ID NO 9
<211> LENGTH: 9
<212> TYPE: PRT
<213> ORGANISM: Mus musculus

<400> SEQUENCE: 9

Gln His His Tyr Gly Thr Pro Pro Thr
1               5

<210> SEQ ID NO 10
<211> LENGTH: 134
<212> TYPE: PRT
<213> ORGANISM: Mus musculus
<220> FEATURE:
<221> NAME/KEY: SIGNAL
<222> LOCATION: (1)..(18)

<400> SEQUENCE: 10

Met Arg Val Leu Ile Leu Leu Cys Leu Phe Thr Ala Phe Pro Gly Ile
1               5                   10                  15

Leu Ser Asp Val Gln Leu Gln Glu Ser Gly Pro Asp Leu Val Lys Pro
            20                  25                  30

Ser Gln Ser Leu Ser Leu Thr Cys Thr Val Thr Gly Tyr Ser Ile Thr
        35                  40                  45

Ser Gly Tyr Ser Trp His Trp Ile Arg Gln Phe Leu Gly Asn Lys Leu
    50                  55                  60

Glu Trp Met Gly Tyr Ile His Tyr Ser Gly Ile Thr Asn Tyr Asn Pro
65                  70                  75                  80

Ser Leu Arg Ser Arg Ile Ser Phe Thr Arg Asp Thr Ser Lys Asn Gln
                85                  90                  95

Phe Phe Leu Gln Leu Asn Ser Val Thr Thr Glu Asp Thr Ala Thr Tyr
            100                 105                 110

Tyr Cys Ala Arg Asp Gly Tyr Tyr Gly Met Asp Tyr Trp Gly Gln Gly
        115                 120                 125

Thr Ser Val Thr Val Ser
    130

<210> SEQ ID NO 11
<211> LENGTH: 127
<212> TYPE: PRT
<213> ORGANISM: Mus musculus
<220> FEATURE:
<221> NAME/KEY: SIGNAL
<222> LOCATION: (1)..(20)

<400> SEQUENCE: 11

Met Asp Phe Gln Thr Gln Val Phe Val Phe Leu Leu Trp Leu Ser
1               5                   10                  15

Gly Val Asp Gly Asp Ile Val Met Thr Gln Ser Gln Lys Phe Met Ser
            20                  25                  30

Thr Ser Val Gly Asp Arg Val Ser Ile Thr Cys Lys Ala Ser Gln Asn
        35                  40                  45
```

```
Val Arg Thr Ser Val Ala Trp Tyr Gln Gln Lys Pro Gly Gln Ser Pro
        50                  55                  60

Lys Ala Leu Ile Tyr Leu Ala Ser Asn Arg His Thr Gly Val Pro Asp
 65                  70                  75                  80

Arg Phe Thr Gly Ser Gly Ser Gly Thr Asp Phe Thr Leu Thr Val Ser
                85                  90                  95

Asn Ile Gln Ser Glu Asp Leu Ala Asp Tyr Phe Cys Leu Gln His Trp
            100                 105                 110

Asn Tyr Pro Tyr Thr Phe Gly Gly Gly Thr Lys Leu Glu Ile Lys
        115                 120                 125

<210> SEQ ID NO 12
<211> LENGTH: 11
<212> TYPE: PRT
<213> ORGANISM: Mus musculus

<400> SEQUENCE: 12

Gly Tyr Ser Ile Thr Ser Gly Tyr Ser Trp His
1               5                   10

<210> SEQ ID NO 13
<211> LENGTH: 9
<212> TYPE: PRT
<213> ORGANISM: Mus musculus

<400> SEQUENCE: 13

Tyr Ile His Tyr Ser Gly Ile Thr Asn
1               5

<210> SEQ ID NO 14
<211> LENGTH: 8
<212> TYPE: PRT
<213> ORGANISM: Mus musculus

<400> SEQUENCE: 14

Asp Gly Tyr Tyr Gly Met Asp Tyr
1               5

<210> SEQ ID NO 15
<211> LENGTH: 11
<212> TYPE: PRT
<213> ORGANISM: Mus musculus

<400> SEQUENCE: 15

Lys Ala Ser Gln Asn Val Arg Thr Ser Val Ala
1               5                   10

<210> SEQ ID NO 16
<211> LENGTH: 7
<212> TYPE: PRT
<213> ORGANISM: Mus musculus

<400> SEQUENCE: 16

Leu Ala Ser Asn Arg His Thr
1               5

<210> SEQ ID NO 17
<211> LENGTH: 8
<212> TYPE: PRT
<213> ORGANISM: Mus musculus

<400> SEQUENCE: 17
```

```
Leu Gln His Trp Asn Tyr Pro Tyr
1               5
```

<210> SEQ ID NO 18
<211> LENGTH: 136
<212> TYPE: PRT
<213> ORGANISM: Mus musculus
<220> FEATURE:
<221> NAME/KEY: SIGNAL
<222> LOCATION: (1)..(19)

<400> SEQUENCE: 18

```
Met Gly Trp Ser Trp Ile Phe Leu Phe Leu Leu Ser Gly Thr Ala Gly
1               5                   10                  15

Val Leu Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Ser Phe
        35                  40                  45

Thr Gly Tyr Tyr Ile His Trp Val Lys Gln Ser His Val Lys Ser Leu
    50                  55                  60

Glu Trp Ile Gly Arg Ile Asn Pro Tyr Tyr Gly Ala Thr Ser Tyr Asn
65                  70                  75                  80

Gln Asn Phe Lys Asp Lys Ala Asn Leu Thr Val Asp Lys Ser Ser Ser
                85                  90                  95

Thr Ala Tyr Met Glu Leu His Ser Leu Thr Ser Asp Asp Ser Ala Val
            100                 105                 110

Tyr Tyr Cys Ala Arg Ser Thr Lys Leu Gly Tyr Leu Asp Tyr Trp Gly
        115                 120                 125

Gln Gly Thr Thr Leu Thr Val Ser
    130                 135
```

<210> SEQ ID NO 19
<211> LENGTH: 127
<212> TYPE: PRT
<213> ORGANISM: Mus musculus
<220> FEATURE:
<221> NAME/KEY: SIGNAL
<222> LOCATION: (1)..(20)

<400> SEQUENCE: 19

```
Met Ser Val Pro Thr Gln Val Leu Gly Leu Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Ala Ser Glu Asn
        35                  40                  45

Ile Tyr Ser Asn Leu Ala Trp Tyr Gln Gln Lys Gln Gly Lys Ser Pro
    50                  55                  60

Gln Leu Leu Ile Tyr Asn Ala Lys Thr Leu Ala Glu Gly Val Pro Ser
65                  70                  75                  80

Arg Phe Ser Gly Ser Gly Ser Gly Thr Gln Tyr Phe Leu Lys Ile Asn
                85                  90                  95

Ser Leu Gln Pro Glu Asp Phe Gly Ser Tyr Tyr Cys Gln His His Tyr
            100                 105                 110

Gly Thr Pro Phe Thr Phe Gly Gly Gly Thr Lys Leu Glu Ile Lys
        115                 120                 125
```

<210> SEQ ID NO 20
<211> LENGTH: 10

```
<212> TYPE: PRT
<213> ORGANISM: Mus musculus

<400> SEQUENCE: 20

Gly Tyr Ser Phe Thr Gly Tyr Tyr Ile His
1               5                   10

<210> SEQ ID NO 21
<211> LENGTH: 9
<212> TYPE: PRT
<213> ORGANISM: Mus musculus

<400> SEQUENCE: 21

Arg Ile Asn Pro Tyr Tyr Gly Ala Thr
1               5

<210> SEQ ID NO 22
<211> LENGTH: 9
<212> TYPE: PRT
<213> ORGANISM: Mus musculus

<400> SEQUENCE: 22

Ser Thr Lys Leu Gly Tyr Leu Asp Tyr
1               5

<210> SEQ ID NO 23
<211> LENGTH: 11
<212> TYPE: PRT
<213> ORGANISM: Mus musculus

<400> SEQUENCE: 23

Arg Ala Ser Glu Asn Ile Tyr Ser Asn Leu Ala
1               5                   10

<210> SEQ ID NO 24
<211> LENGTH: 7
<212> TYPE: PRT
<213> ORGANISM: Mus musculus

<400> SEQUENCE: 24

Asn Ala Lys Thr Leu Ala Glu
1               5

<210> SEQ ID NO 25
<211> LENGTH: 9
<212> TYPE: PRT
<213> ORGANISM: Mus musculus

<400> SEQUENCE: 25

Gln His His Tyr Gly Thr Pro Phe Thr
1               5

<210> SEQ ID NO 26
<211> LENGTH: 137
<212> TYPE: PRT
<213> ORGANISM: Mus musculus
<220> FEATURE:
<221> NAME/KEY: SIGNAL
<222> LOCATION: (1)..(19)

<400> SEQUENCE: 26

Met Gly Trp Ser Trp Ile Phe Leu Phe Leu Leu Ser Gly Thr Ala Gly
1               5                   10                  15

Val Leu Ser Glu Val Gln Leu Gln Gln Ser Gly Pro Glu Leu Val Lys
            20                  25                  30
```

Pro Gly Ala Ser Val Lys Ile Ser Cys Lys Ala Ser Gly Tyr Ser Phe
                35                  40                  45

Thr Gly Tyr Phe Met His Trp Val Lys Gln Ser His Val Lys Ser Leu
    50                  55                  60

Glu Trp Ile Gly Arg Ile Asn Pro Tyr Asn Gly Ala Thr Ser Tyr Asn
65                  70                  75                  80

Gln Asn Phe Lys Asp Lys Ala Ser Leu Thr Val Asp Lys Ser Ser Ser
                85                  90                  95

Thr Ser Tyr Met Glu Leu His Ser Leu Thr Ser Glu Asp Ser Ala Val
                100                 105                 110

Tyr Tyr Cys Val Arg Asp Asp Gly Gly Asn Tyr Pro Phe Asp Tyr Trp
                115                 120                 125

Gly Gln Gly Thr Thr Leu Thr Val Ser
                130                 135

<210> SEQ ID NO 27
<211> LENGTH: 127
<212> TYPE: PRT
<213> ORGANISM: Mus musculus
<220> FEATURE:
<221> NAME/KEY: SIGNAL
<222> LOCATION: (1)..(20)

<400> SEQUENCE: 27

Met Ser Val Pro Thr Gln Val Leu Gly Leu Leu Leu Leu Trp Leu Thr
1               5                   10                  15

Gly Ala Arg Cys Asp Ile Gln Met Thr Gln Ser Pro Ala Ser Leu Ser
                20                  25                  30

Ala Ser Val Gly Glu Thr Val Thr Ile Thr Cys Arg Ala Ser Glu Asn
                35                  40                  45

Ile Tyr Ser Tyr Leu Ala Trp Tyr Gln Gln Lys Gln Gly Lys Ser Pro
        50                  55                  60

Gln Leu Leu Val Tyr Tyr Ala Lys Thr Leu Ala Glu Gly Val Pro Ser
65                  70                  75                  80

Arg Phe Ser Gly Ser Gly Thr Gly Thr Gln Phe Ser Leu Lys Ile Asn
                85                  90                  95

Ser Leu Gln Pro Glu Asp Phe Gly Ser Tyr Tyr Cys Gln His His Tyr
                100                 105                 110

Gly Thr Pro Tyr Thr Phe Gly Gly Gly Thr Lys Leu Glu Ile Lys
                115                 120                 125

<210> SEQ ID NO 28
<211> LENGTH: 10
<212> TYPE: PRT
<213> ORGANISM: Mus musculus

<400> SEQUENCE: 28

Gly Tyr Ser Phe Thr Gly Tyr Phe Met His
1               5                   10

<210> SEQ ID NO 29
<211> LENGTH: 10
<212> TYPE: PRT
<213> ORGANISM: Mus musculus

<400> SEQUENCE: 29

Arg Ile Asn Pro Tyr Asn Gly Ala Thr Ser
1               5                   10

```
<210> SEQ ID NO 30
<211> LENGTH: 10
<212> TYPE: PRT
<213> ORGANISM: Mus musculus

<400> SEQUENCE: 30

Asp Asp Gly Gly Asn Tyr Pro Phe Asp Tyr
1               5                   10

<210> SEQ ID NO 31
<211> LENGTH: 11
<212> TYPE: PRT
<213> ORGANISM: Mus musculus

<400> SEQUENCE: 31

Arg Ala Ser Glu Asn Ile Tyr Ser Tyr Leu Ala
1               5                   10

<210> SEQ ID NO 32
<211> LENGTH: 7
<212> TYPE: PRT
<213> ORGANISM: Mus musculus

<400> SEQUENCE: 32

Tyr Ala Lys Thr Leu Ala Glu
1               5

<210> SEQ ID NO 33
<211> LENGTH: 9
<212> TYPE: PRT
<213> ORGANISM: Mus musculus

<400> SEQUENCE: 33

Gln His His Tyr Gly Thr Pro Tyr Thr
1               5

<210> SEQ ID NO 34
<211> LENGTH: 137
<212> TYPE: PRT
<213> ORGANISM: Mus musculus
<220> FEATURE:
<221> NAME/KEY: SIGNAL
<222> LOCATION: (1)..(19)

<400> SEQUENCE: 34

Met Glu Trp Arg Trp Ile Phe Leu Phe Leu Leu Ser Gly Thr Thr Gly
1               5                   10                  15

Val His Ser Glu Ile Gln Leu Gln Gln Ser Gly Pro Glu Leu Val Lys
                20                  25                  30

Pro Gly Ala Ser Val Lys Val Ser Cys Lys Ala Ser Gly Tyr Val Phe
            35                  40                  45

Thr Thr Tyr Ser Ile Tyr Trp Val Lys Gln Ser His Gly Lys Ser Leu
        50                  55                  60

Glu Trp Ile Gly Tyr Ile Asp Pro Tyr Asn Gly Asp Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met His Leu Asn Ser Leu Thr Ser Glu Asp Ser Thr Val
            100                 105                 110

Tyr Tyr Cys Ala Arg Glu Gly Asn Tyr Tyr Gly Tyr Phe Asp Tyr Trp
        115                 120                 125
```

Gly Gln Gly Thr Thr Leu Thr Val Ser
    130                 135

<210> SEQ ID NO 35
<211> LENGTH: 128
<212> TYPE: PRT
<213> ORGANISM: Mus musculus
<220> FEATURE:
<221> NAME/KEY: SIGNAL
<222> LOCATION: (1)..(22)

<400> SEQUENCE: 35

Met Asp Phe Gln Val Gln Ile Phe Ser Phe Leu Leu Met Ser Ala Ser
1               5                   10                  15

Val Ile Met Ser Arg Gly Gln Ile Val Leu Thr Gln Ser Pro Ala Leu
            20                  25                  30

Met Ser Ala Ser Pro Gly Glu Lys Val Thr Met Thr Cys Ser Ala Ser
        35                  40                  45

Ser Ser Val Ser Tyr Met Phe Trp Tyr Gln Gln Lys Pro Arg Ser Ser
    50                  55                  60

Pro Lys Pro Trp Ile Tyr Leu Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Trp
            100                 105                 110

Thr Gly Asn Pro Pro Thr Phe Gly Gly Thr Lys Leu Glu Ile Lys
        115                 120                 125

<210> SEQ ID NO 36
<211> LENGTH: 10
<212> TYPE: PRT
<213> ORGANISM: Mus musculus

<400> SEQUENCE: 36

Gly Tyr Val Phe Thr Thr Tyr Ser Ile Tyr
1               5                   10

<210> SEQ ID NO 37
<211> LENGTH: 10
<212> TYPE: PRT
<213> ORGANISM: Mus musculus

<400> SEQUENCE: 37

Tyr Ile Asp Pro Tyr Asn Gly Asp Thr Ser
1               5                   10

<210> SEQ ID NO 38
<211> LENGTH: 10
<212> TYPE: PRT
<213> ORGANISM: Mus musculus

<400> SEQUENCE: 38

Glu Gly Asn Tyr Tyr Gly Tyr Phe Asp Tyr
1               5                   10

<210> SEQ ID NO 39
<211> LENGTH: 10
<212> TYPE: PRT
<213> ORGANISM: Mus musculus

<400> SEQUENCE: 39

Ser Ala Ser Ser Ser Val Ser Tyr Met Phe
1               5                   10

<210> SEQ ID NO 40
<211> LENGTH: 7
<212> TYPE: PRT
<213> ORGANISM: Mus musculus

<400> SEQUENCE: 40

Leu Thr Ser Asn Leu Ala Ser
1               5

<210> SEQ ID NO 41
<211> LENGTH: 9
<212> TYPE: PRT
<213> ORGANISM: Mus musculus

<400> SEQUENCE: 41

Gln Gln Trp Thr Gly Asn Pro Pro Thr
1               5

<210> SEQ ID NO 42
<211> LENGTH: 285
<212> TYPE: DNA
<213> ORGANISM: Mus musculus

<400> SEQUENCE: 42

```
gacattgtga tgacccagtc tcaaaaattc atgtccacat cagtaggaga cagggtcagc    60
atcacctgca aggccagtca gaatgttcgt actgctgtag cctggtatca acagaaacca   120
gggcagtctc ctaaagcact gatttacttg gcatccaacc ggcacactgg agtccctgat   180
cgcttcacag gcagtggatc tgggacagat ttcactctca ccattagcaa tgtgcaatct   240
gaagacctgg cagattattt ctgtctgcaa cattggaatt atcct                   285
```

<210> SEQ ID NO 43
<211> LENGTH: 285
<212> TYPE: DNA
<213> ORGANISM: Mus musculus

<400> SEQUENCE: 43

```
caaattgttc tcacccagtc tccagcactc atgtctgcat ctccagggga aaggtcacc     60
atgacctgca gtgccagctc aagtgtaagt tacatgtact ggtaccagca gaagccaaga   120
tcctccccca aaccctggat ttatctcaca tccaacctgg cttctggagt ccctgctcgc   180
ttcagtggca gtgggtctgg gacctcttac tctctcacaa tcagcagcat ggaggctgaa   240
gatgctgcca cttattactg ccagcagtgg agtagtaacc caccc                   285
```

<210> SEQ ID NO 44
<211> LENGTH: 285
<212> TYPE: DNA
<213> ORGANISM: Mus musculus

<400> SEQUENCE: 44

```
gacatccaga tgactcagtc tccagcctcc tatctgcat ctgtgggaga aactgtcacc     60
atcacatgtc gagcaagtga aaatatttac agttatttag catggtatca gcagaaacag   120
ggaaaatctc ctcagctcct ggtctataat gcaaaaacct agcagaagg tgtgccatca    180
aggttcagtg gcagtggatc aggcacacag ttttctctga agatcaacag cctgcagcct   240
gaagattttg ggagttatta ctgtcaacat cattatggta ctcct                   285
```

```
<210> SEQ ID NO 45
<211> LENGTH: 39
<212> TYPE: DNA
<213> ORGANISM: Mus musculus

<400> SEQUENCE: 45
tacacgttcg gagggggggac caagctggaa ataaaacgt                         39

<210> SEQ ID NO 46
<211> LENGTH: 294
<212> TYPE: DNA
<213> ORGANISM: Mus musculus

<400> SEQUENCE: 46
gatgtgcagc ttcaggagtc aggacctgac ctggtgaaaac cttctcagtc actttcactc   60
acctgcactg tcactggcta ctccatcacc agtggttata gctggcactg gatccggcag  120
tttccaggaa acaaactgga atggatgggc tacatacact acagtggtag cactaactac  180
aacccatctc tcaaaagtcg aatctctatc actcgagaca catccaagaa ccagttcttc  240
ctgcagttga attctgtgac tactgaggac acagccacat attactgtgc aaga         294

<210> SEQ ID NO 47
<211> LENGTH: 294
<212> TYPE: DNA
<213> ORGANISM: Mus musculus

<400> SEQUENCE: 47
gaggtccagc tgcagcagtc tggacctgag ctagtgaaga ctggggcttc agtgaagata   60
tcctgcaagg cttctggtta ctcattcact ggttactaca tgcactgggt caagcagagc  120
catggaaaga gccttgagtg gattggatat attagttgtt acaatggtgc tactagctac  180
aaccagaagt tcaagggcaa ggccacattt actgtagaca catcctccag cacagcctac  240
atgcagttca acagcctgac atctgaagac tctgcggtct attactgtgc aaga         294

<210> SEQ ID NO 48
<211> LENGTH: 294
<212> TYPE: DNA
<213> ORGANISM: Mus musculus

<400> SEQUENCE: 48
gaggtccagc tgcaacagtc tggacctgag ctggtgaagc ctggggcttc agtgaagata   60
tcctgcaagg cttctggtta ctcattcact ggctactaca tgcactgggt gaagcaaagc  120
catgtaaaga gccttgagtg gattggacgt attaatcctt acaatggtgc tactagctac  180
aaccagaatt tcaaggacaa ggccagcttg actgtagata gtcctccag cacagcctac  240 atggagctcc acagcctgac atctgaggac tctgcagtct attactgtgc aagg         294

<210> SEQ ID NO 49
<211> LENGTH: 45
<212> TYPE: DNA
<213> ORGANISM: Mus musculus

<400> SEQUENCE: 49
tactttgact actggggcca aggcaccact ctcacagtct cctca                   45

<210> SEQ ID NO 50
<211> LENGTH: 53
<212> TYPE: DNA
<213> ORGANISM: Mus musculus
```

<400> SEQUENCE: 50
attactatgc tatggactac tggggtcaag gaacctcagt caccgtctcc tca    53

<210> SEQ ID NO 51
<211> LENGTH: 408
<212> TYPE: DNA
<213> ORGANISM: Mus musculus

<400> SEQUENCE: 51
atgggatgga gctggatctt tctctttctc ctgtcaggaa ctgcaggtgt cctctctgag    60
gtccagctgc aacagtctgg acctgagctg gtgaagcctg ggcttcagt gaagatatcc    120 tgcaagcctt ctggttactc attcactgcc tactacatgc actgggtgaa gcaaagccat    180
gtaaagagcc ttgagtggat tggacgtatt aatccttaca atggtgctac tagctacaac    240
cggaatttca aggacaaggc cagcttgact gtagataagt cctccagcac agcctacatg    300
gagctccaca gcctgacatc tgaggactct gcagtctatt actgtgcaag aagtggggggt    360 aatacgtact ttgactactg gggccaaggc accactctca cagtctcc    408

<210> SEQ ID NO 52
<211> LENGTH: 381
<212> TYPE: DNA
<213> ORGANISM: Mus musculus

<400> SEQUENCE: 52
atgagtgtgc ccactcaggt cctggggttg ctgctgctgt ggcttacagg tgccagatgt    60
gacatccaga tgactcagtc tccagcctcc ctatctgcat ctgtgggaga aactgtcacc    120
atcacatgtc gagcaagtga gaatatttac agttctttag catggtatca gcagaaacag    180
ggaaaatctc ctcagctcct ggtctataat gcaaaaacct tagcagaagg tgtgccatcg    240
aggttcagtg gcagtggatc aggcacacag ttttctctga agatcaacag cctgcagcct    300
gaagatyttg ggacttatta ctgtcaacat cattatggta ctcctccgac gttcggtgga    360
ggcaccaagc tagaaatcaa a    381

<210> SEQ ID NO 53
<211> LENGTH: 402
<212> TYPE: DNA
<213> ORGANISM: Mus musculus

<400> SEQUENCE: 53
atgagagtgc tgattctttt gtgcctgttc acagcctttc tggtatcct gtctgatgtg    60 cagcttcagg agtcaggacc tgacctggtg aaaccttctc agtcactttc actcacctgc    120
actgtcactg gctactccat caccagtggt tatagctggc actggatccg gcagtttcta    180
ggaaacaaac tggaatggat gggctacatt cactacagtg gtatcactaa ctacaaccca    240
tctctcagaa gtcgaatctc tttcactcga gacacatcca agaaccagtt cttcctgcag    300
ttgaattctg tgactactga ggacacagcc acatattact gtgcaagaga tggttattat    360
ggtatggact actggggtca aggaacctca gtcaccgtct cc    402

<210> SEQ ID NO 54
<211> LENGTH: 381
<212> TYPE: DNA
<213> ORGANISM: Mus musculus

<400> SEQUENCE: 54

```
atggactttc agacccaggt ctttgtattc gtgttgctct ggttgtctgg tgttgatgga      60
gacattgtga tgacccagtc tcaaaaattc atgtccacat cagtaggaga cagggtcagc     120
atcacctgca aggccagtca gaatgttcgt acttctgtag cctggtatca acagaaacca     180
gggcagtctc ctaaagcact gatttacttg catccaacc ggcacactgg agtccctgat      240
cgcttcacag gcagtggatc tgggacagat ttcactctca ccgttagcaa tattcaatct     300
gaggacctgg cagattattt ctgtctgcaa cattggaatt atccgtacac gttcggaggg     360
gggaccaagc tggaaataaa a                                                381
```

<210> SEQ ID NO 55
<211> LENGTH: 408
<212> TYPE: DNA
<213> ORGANISM: Mus musculus

<400> SEQUENCE: 55

```
atgggatgga gctggatctt tctctttctc ctgtcaggaa ctgcaggtgt cctctctgag      60
gtccagctgc aacagtctgg acctgagctg gtgaagcctg ggcttcagt gaagatatcc      120 tgcaaggctt ctggttactc attcactggc tactacatac actgggtgaa acaaagccat     180
gtaaagagcc ttgagtggat tgacgtatt aatccttact atggtgctac tagctacaac      240
cagaatttca aggacaaggc caacttgact gtagataagt cctccagcac agcctacatg     300
gagctccaca gtctgacatc tgacgactct gcagtctatt actgtgcaag atcgaccaaa    360
ctggggtatc ttgactactg gggccaaggc accactctca cagtctcc                   408
```

<210> SEQ ID NO 56
<211> LENGTH: 381
<212> TYPE: DNA
<213> ORGANISM: Mus musculus

<400> SEQUENCE: 56

```
atgagtgtgc ccactcaggt cctggggttg ctgctgctgt ggcttacagg tgccagatgt      60
gacatccaga tgactcagtc tccagcctcc ctatctgcat ctgtgggaga aactgtcacc     120
atcacatgtc gagcaagtga gaatatttac agtaatttag catggtatca gcagaaacag     180
ggaaaatctc ctcagctcct gatctataat gcaaaaacct agcagaagg tgtgccatca     240 aggttcagtg gcagtggatc aggcacacaa tattttctga agatcaacag cctgcagcct     300
gaagattttg ggagttatta ctgtcaacat cattatggta ctccgttcac gttcggaggg     360
gggaccaagc tggaaataaa a                                                381
```

<210> SEQ ID NO 57
<211> LENGTH: 411
<212> TYPE: DNA
<213> ORGANISM: Mus musculus

<400> SEQUENCE: 57

```
atgggatgga gctggatctt tctctttctc ctgtcaggaa ctgcaggtgt cctctctgag      60
gtccagctgc aacagtctgg acctgagctg gtgaagcctg ggcttcagt gaagatatcc      120 tgcaaggctt ctggttactc attcactggc tacttcatgc actgggtgaa gcaaagccat     180
gtaaagagcc ttgagtggat tgacgtatt aatccttaca atggcgctac tagctacaac      240
cagaatttca aggacaaggc cagcttgact gtagataagt cctccagcac atcctacatg     300
gaactccaca gcctgacatc tgaggactct gcagtctatt actgtgtaag agacgacggt    360
ggtaactacc cttttgacta ctggggccag ggcaccactc tcacagtctc c               411
```

<210> SEQ ID NO 58
<211> LENGTH: 381
<212> TYPE: DNA
<213> ORGANISM: Mus musculus

<400> SEQUENCE: 58

```
atgagtgtgc ccactcaggt cctggggttg ctgctgctgt ggcttacagg tgccagatgt      60
gacatccaga tgactcagtc tccagcctcc ctatctgcat ctgtgggaga aactgtcacc     120
atcacatgtc gagcaagtga aaatatttac agttatttag catggtatca gcagaaacag     180
ggaaaatctc ctcagctcct ggtctattat gcaaaaacct tagcagaagg tgtgccatca     240
aggttcagtg gcagtggaac aggcacacag ttttctctga agatcaacag cctgcagcct     300
gaagattttg ggagttacta ctgtcaacat cattatggta ctccgtacac gttcggaggg     360
gggaccaagc tggaaataaa a                                              381
```

<210> SEQ ID NO 59
<211> LENGTH: 411
<212> TYPE: DNA
<213> ORGANISM: Mus musculus

<400> SEQUENCE: 59

```
atggaatgga gatggatctt tctcttcctc ctgtcaggaa ctacaggtgt ccactctgag      60
atccagctgc agcagtctgg acctgagttg gtgaagcctg ggcttcagt gaaggtatcc      120
tgcaaggctt ctggttatgt attcactacc tacagcattt actgggtgaa gcagagccat     180
ggaaagagcc ttgagtggat tggatatatt gatccttaca atggtgatac tagctacaac     240
cagaagttca gggcaaggc cacattgact gttgacaagt cctccagcac agcctacatg     300
catctcaaca gcctgacatc tgaggactct acagtctatt actgcgcaag agagggcaat     360
tactacggct actttgacta ctggggccaa ggcaccactc tcacagtctc c              411
```

<210> SEQ ID NO 60
<211> LENGTH: 384
<212> TYPE: DNA
<213> ORGANISM: Mus musculus

<400> SEQUENCE: 60

```
atggattttc aagtgcagat tttcagcttc ctgctaatga gtgcctcagt cataatgtcc      60
aggggacaaa ttgttctcac ccagtctcca gcactcatgt ctgcatctcc aggggagagg     120
gtcaccatga cctgcagtgc cagctcaagt gtaagttaca tgttctggta ccagcagaag     180
ccaagatcct cacccaaacc ctggatttat ctcacatcca acctggcttc tggagtccct     240
gctcgcttca gtggcagtgg gtctgggacc tcttactctc tcacaatcag cagcatggag     300
gctgaagatg ctgccactta ttactgccag cagtggactg taacccacc cacgttcgga     360
gggggaccaa gctggaaat aaaa                                             384
```

<210> SEQ ID NO 61
<211> LENGTH: 11
<212> TYPE: PRT
<213> ORGANISM: Mus musculus
<220> FEATURE:
<221> NAME/KEY: misc_feature
<222> LOCATION: (9)..(9)
<223> OTHER INFORMATION: Xaa can be any naturally occurring amino acid

<400> SEQUENCE: 61

```
Arg Ala Ser Glu Asn Ile Tyr Ser Xaa Leu Ala
1               5                   10
```

<210> SEQ ID NO 62
<211> LENGTH: 7
<212> TYPE: PRT
<213> ORGANISM: Mus musculus
<220> FEATURE:
<221> NAME/KEY: misc_feature
<222> LOCATION: (1)..(1)
<223> OTHER INFORMATION: Xaa can be any naturally occurring amino acid

<400> SEQUENCE: 62

```
Xaa Ala Lys Thr Leu Ala Glu
1               5
```

<210> SEQ ID NO 63
<211> LENGTH: 9
<212> TYPE: PRT
<213> ORGANISM: Mus musculus
<220> FEATURE:
<221> NAME/KEY: misc_feature
<222> LOCATION: (8)..(8)
<223> OTHER INFORMATION: Xaa can be any naturally occurring amino acid

<400> SEQUENCE: 63

```
Gln His His Tyr Gly Thr Pro Xaa Thr
1               5
```

<210> SEQ ID NO 64
<211> LENGTH: 11
<212> TYPE: PRT
<213> ORGANISM: Mus musculus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(11)
<223> OTHER INFORMATION: Xaa can be any naturally occurring amino acid

<400> SEQUENCE: 64

```
Xaa Ala Ser Xaa Xaa Xaa Xaa Xaa Xaa Xaa Xaa
1               5                   10
```

<210> SEQ ID NO 65
<211> LENGTH: 7
<212> TYPE: PRT
<213> ORGANISM: Mus musculus
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 65

```
Xaa Xaa Xaa Xaa Leu Ala Xaa
1               5
```

<210> SEQ ID NO 66
<211> LENGTH: 7
<212> TYPE: PRT
<213> ORGANISM: Mus musculus
<220> FEATURE:
<221> NAME/KEY: misc_feature
<222> LOCATION: (1)..(1)

```
<223> OTHER INFORMATION: Xaa can be any naturally occurring amino acid
<220> FEATURE:
<221> NAME/KEY: misc_feature
<222> LOCATION: (3)..(7)
<223> OTHER INFORMATION: Xaa can be any naturally occurring amino acid

<400> SEQUENCE: 66

Xaa Ala Xaa Xaa Xaa Xaa Xaa
1               5

<210> SEQ ID NO 67
<211> LENGTH: 7
<212> TYPE: PRT
<213> ORGANISM: Mus musculus
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid

<400> SEQUENCE: 67

Leu Xaa Ser Asn Xaa Xaa Xaa
1               5

<210> SEQ ID NO 68
<211> LENGTH: 9
<212> TYPE: PRT
<213> ORGANISM: Mus musculus
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 68

Gln Xaa Xaa Xaa Gly Xaa Pro Xaa Thr
1               5

<210> SEQ ID NO 69
<211> LENGTH: 9
<212> TYPE: PRT
<213> ORGANISM: Mus musculus
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 69

Xaa Xaa His Xaa Xaa Xaa Pro Xaa Thr
1               5

<210> SEQ ID NO 70
<211> LENGTH: 9
```

<212> TYPE: PRT
<213> ORGANISM: Mus musculus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 70

Xaa Gln Xaa Xaa Xaa Xaa Pro Xaa Thr
1               5

<210> SEQ ID NO 71
<211> LENGTH: 10
<212> TYPE: PRT
<213> ORGANISM: Mus musculus
<220> FEATURE:
<221> NAME/KEY: misc_feature
<222> LOCATION: (8)..(9)
<223> OTHER INFORMATION: Xaa can be any naturally occurring amino acid

<400> SEQUENCE: 71

Gly Tyr Ser Phe Thr Gly Tyr Xaa Xaa His
1               5                   10

<210> SEQ ID NO 72
<211> LENGTH: 10
<212> TYPE: PRT
<213> ORGANISM: Mus musculus
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 72

Gly Tyr Ser Phe Thr Xaa Tyr Xaa Met His
1               5                   10

<210> SEQ ID NO 73
<211> LENGTH: 10
<212> TYPE: PRT
<213> ORGANISM: Mus musculus
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 73

Gly Tyr Ser Phe Thr Xaa Tyr Tyr Xaa His
1               5                   10

<210> SEQ ID NO 74
<211> LENGTH: 10
<212> TYPE: PRT
<213> ORGANISM: Mus musculus
<220> FEATURE:

```
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(10)
<223> OTHER INFORMATION: Xaa can be any naturally occurring amino acid

<400> SEQUENCE: 74

Gly Tyr Xaa Phe Thr Xaa Tyr Xaa Xaa Xaa
1               5                   10

<210> SEQ ID NO 75
<211> LENGTH: 11
<212> TYPE: PRT
<213> ORGANISM: Mus musculus
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 75

Gly Tyr Ser Xaa Thr Xaa Gly Tyr Xaa Xaa His
1               5                   10

<210> SEQ ID NO 76
<211> LENGTH: 11
<212> TYPE: PRT
<213> ORGANISM: Mus musculus
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 76

Gly Tyr Xaa Xaa Thr Xaa Xaa Tyr Ser Xaa Xaa
1               5                   10

<210> SEQ ID NO 77
<211> LENGTH: 17
<212> TYPE: PRT
<213> ORGANISM: Mus musculus
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
```

<223> OTHER INFORMATION: Xaa can be any naturally occurring amino acid

<400> SEQUENCE: 77

Arg Ile Asn Pro Tyr Xaa Gly Ala Thr Ser Xaa Asn Xaa Asn Phe Lys
1               5                   10                  15

Asp

<210> SEQ ID NO 78
<211> LENGTH: 17
<212> TYPE: PRT
<213> ORGANISM: Mus musculus
<220> FEATURE:
<221> NAME/KEY: misc_feature
<222> LOCATION: (6)..(6)
<223> OTHER INFORMATION: Xaa can be any naturally occurring amino acid

<400> SEQUENCE: 78

Arg Ile Asn Pro Tyr Xaa Gly Ala Thr Ser Tyr Asn Gln Asn Phe Lys
1               5                   10                  15

Asp

<210> SEQ ID NO 79
<211> LENGTH: 17
<212> TYPE: PRT
<213> ORGANISM: Mus musculus
<220> FEATURE:
<221> NAME/KEY: misc_feature
<222> LOCATION: (13)..(13)
<223> OTHER INFORMATION: Xaa can be any naturally occurring amino acid

<400> SEQUENCE: 79

Arg Ile Asn Pro Tyr Asn Gly Ala Thr Ser Tyr Asn Xaa Asn Phe Lys
1               5                   10                  15

Asp

<210> SEQ ID NO 80
<211> LENGTH: 17
<212> TYPE: PRT
<213> ORGANISM: Mus musculus
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (13)..(17)
<223> OTHER INFORMATION: Xaa can be any naturally occurring amino acid

<400> SEQUENCE: 80

Tyr Ile Xaa Xaa Tyr Xaa Gly Xaa Thr Xaa Tyr Asn Xaa Xaa Xaa Xaa
1               5                   10                  15

Xaa

<210> SEQ ID NO 81
<211> LENGTH: 17

```
<212> TYPE: PRT
<213> ORGANISM: Mus musculus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(17)
<223> OTHER INFORMATION: Xaa can be any naturally occurring amino acid

<400> SEQUENCE: 81

Xaa Ile Xaa Xaa Tyr Xaa Gly Xaa Thr Xaa Xaa Asn Xaa Xaa Xaa Xaa
1               5                   10                  15

Xaa

<210> SEQ ID NO 82
<211> LENGTH: 10
<212> TYPE: PRT
<213> ORGANISM: Mus musculus
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 82

Xaa Xaa Gly Xaa Xaa Tyr Xaa Phe Asp Tyr
1               5                   10

<210> SEQ ID NO 83
<211> LENGTH: 10
<212> TYPE: PRT
<213> ORGANISM: Mus musculus
<220> FEATURE:
<221> NAME/KEY: misc_feature
<222> LOCATION: (1)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 83

Xaa Xaa Xaa Xaa Xaa Tyr Xaa Xaa Asp Tyr
1               5                   10

<210> SEQ ID NO 84
<211> LENGTH: 10
```

```
<212> TYPE: PRT
<213> ORGANISM: Mus musculus
<220> FEATURE:
<221> NAME/KEY: misc_feature
<222> LOCATION: (1)..(7)
<223> OTHER INFORMATION: Xaa can be any naturally occurring amino acid

<400> SEQUENCE: 84

Xaa Xaa Xaa Xaa Xaa Xaa Xaa Phe Asp Tyr
1               5                   10

<210> SEQ ID NO 85
<211> LENGTH: 10
<212> TYPE: PRT
<213> ORGANISM: Mus musculus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 85

Xaa Gly Xaa Xaa Tyr Xaa Xaa Xaa Asp Tyr
1               5                   10
```

US 9,388,246 B2

TLR3 BINDING AGENTS

CROSS-REFERENCE TO RELATED APPLICATIONS

This application claims priority to and is a continuation of PCT International Application Number PCT/EP2010/059946, filed on Jul. 9, 2010, entitled TLR3 Binding Agents, and published in English on Jan. 13, 2011, which claims priority to U.S. patent application 61/224,548, filed on Jul. 10, 2009. The disclosures of each of the above-described applications are hereby incorporated herein by reference in their entireties.

FIELD OF THE INVENTION

The present invention relates to antibodies (e.g. monoclonal antibodies), antibody fragments, and derivatives thereof that specifically bind TLR3, and that optionally further modulate, e.g. inhibit, signaling. The invention also relates to cells producing such antibodies; methods of making such antibodies; fragments, variants, and derivatives of the antibodies; pharmaceutical compositions comprising the same; methods of using the antibodies to diagnose, treat or prevent diseases, e.g. autoimmune diseases, inflammatory diseases and the like.

BACKGROUND

*Drosophila* toll proteins control dorsal-ventral patterning and are thought to represent an ancient host defense mechanism. In humans, TLRs are believed to be an important component of innate immunity. Human and *Drosophila* Toll protein sequences show homology over the entire length of the protein chains. The family of human Toll-like receptors is comprised of ten highly conserved receptor proteins, TLR1-TLR10. Like *Drosophila* toll, human TLRs are type I transmembrane proteins with an extracellular domain consisting of a leucine-rich repeat (LRR) domain that recognizes pathogen-associated molecular patterns (PAMPs), and a cytoplasmic domain that is homologous to the cytoplasmic domain of the human interleukin-1 (IL-1) receptor. Similar to the signaling pathways for both *Drosophila* toll and the IL-1 receptor, human Toll-like receptors signal through the NF-κB pathway.

Although the different mammalian TLRs share many characteristics and signal transduction mechanisms, their biological functions are very different. This is due in part to the fact that four different adaptor molecules (MyD88, TIRAP, TRIF and TRAF) are associated in various combinations with the TLRs and mediate different signaling pathways. In addition, different ligands for one TLR may preferentially activate different signal transduction pathways. Furthermore, the TLRs are differentially expressed in various hematopoietic and non-hematopoietic cells. Accordingly, the response to a TLR ligand depends not only on the signal pathway activated by the TLR, but also on the nature of the cells in which the individual TLR is expressed.

Toll-like receptor 3 (TLR3) has received considerable attention as a therapeutic target as TLR3 signaling has been implicated in inflammatory and autoimmune conditions. Patent application WO98/50547 provides the nucleic acid and amino acid sequence of the hTLR3 protein. LeBouteiller et al. (2005) J. Biol. Chem. 280(46): 38133-38145) disclose use of an anti-TLR3 antibody to bind cell surface TLR3. Antibody C1130 is stated to be activatory toward TLR3 and has been described in WO 2007/051164. Polyclonal antibodies that inhibited TLR3 were described in Cavassani et al. (2008) J. Exp. Med. 205: 2609-2621. WO 03/106499 and Matsumoto et al. (2003) J. Immunol. 171:3154-3162 describes an antibody corresponding to antibody clone TLR3.7 (eBioScience Inc., San Diego) reported to bind and inhibit cell surface TLR3 but not cell compartment TLR3 or in myeloid-lineage DC. WO 06/060513 describes an antibody C1068 which is reported to inhibit cytokine production in epithelial cells, which are reported to express TLR3 on the cell surface. C1068 is stated to compete with antibody TLR3.7 for binding to TLR3 (see WO2010/051470). PCT patent application WO2010/051470 provides anti-TLR3 antibodies. Such antibodies are stated to block dsRNA and are proposed to prevent binding of dsRNA to TLR3. Other anti-TLR3 antibodies for research use include polyclonal anti-TLR3 antibodies from R&D Systems Corp., antibody 40C1285 from Abcam and antibodies 619F7, 713E4, 716G10, IMG-5631 and -IMG-5348, all from Imgenex. Corp.

However, while several anti-TLR3 antibodies have been generated to date, these antibodies have generally been intended for research only, and not for therapeutic use. As further described herein, the present disclosure shows that among currently available anti-TLR3 antibodies, while they may be useful in some research settings to make experimental observations, they are not optimally suited for use as therapeutic agents, e.g. to modulate TLR3. There is therefore a need to provide improved antibodies directed to TLR3.

SUMMARY OF THE INVENTION

In one aspect, the present invention provides novel compositions comprising, and methods of using monoclonal antibodies, including but not limited to antibody fragments, and derivatives that specifically bind human TLR3. In one aspect, the antibodies inhibit TLR3 signaling without blocking the binding of a TLR3 ligand to a TLR3 polypeptide. In one aspect, the antibodies bind human TLR3 under acidic conditions, and in particular under conditions representative of that encountered in an acidified subcellular compartment of a cell (e.g. compartments of the endocytic pathway endosomic, lysosomal). Such acidic conditions are generally characterized by a pH lower than about pH 6.5, or between about pH 4.5 to 6.5, or about pH 5.6.

In one aspect of any of the embodiments herein, the antibodies modulate, optionally inhibit, TLR3 signaling in an acidified subcellular compartment of a cell (e.g. compartments of the endocytic pathway endosomic, lysosomal).

In one aspect of any of the embodiments herein, the antibodies modulate, optionally inhibit, TLR3 signaling in a dendritic cell (DC) (e.g. a myeloid DC, monocyte derived DC).

In one aspect of any of the embodiments herein, the antibodies can optionally be characterized as not having substantially lower affinity for binding human TLR3 under acidic conditions than under neutral conditions e.g. where the $K_D$ for binding to TLR3 decreases by no more than 0.2-, 0.3-, -0.4, 0.5-, 1.0-, or 1.5-$\log_{10}$. Neutral conditions are generally characterized by a pH between 6.6 and 7.4, for example a slightly alkaline pH of 7.2 found in the cell cytosol. Optionally, the antibodies do not have substantially different (lower or higher) affinity for binding human TLR3 under acidic conditions than under neutral conditions e.g. where the $K_D$ for binding to TLR3 under neutral and acidic conditional differs by no more than 0.2-, 0.3-, 0.4-, 0.5-, 1.0-, or 1.5-$\log_{10}$.

In other aspects of any of the embodiments herein, the antibodies' bivalent binding affinity for TLR3 under acidic conditions can optionally be characterized by a mean $K_D$ of no more than about (i.e. better affinity than) 100, 50, 10, 5, or 1 nanomolar, preferably sub-nanomolar or optionally no more than about 300, 200, 100 or 10 picomolar.

In other aspects of any of the embodiments herein, the antibodies inhibit TLR3 signaling without blocking the binding of a TLR3 ligand to a TLR3 polypeptide. The TLR3 ligand will generally be a ligand other than an anti-TLR3 antibody and may be a naturally occurring or non-naturally occurring TLR3 ligand, optionally a dsRNA-based ligand such as polyAU (polyadenylic acid:polyuridylic acid) or polyIC (polyinosinic:polycytidylic acid). In particular, the inventors have established that the antibodies according to the invention are able to inhibit TLR3 signaling even when a TLR3 ligand such as dsRNA is already bound to the TLR3 polypeptide. The antibodies according to the invention are also able to inhibit TLR3 signaling even in a pre-actived condition, e.g., in the presence of IFNα. The antibodies according to the invention are believed to be effective to treat a patient having an established autoimmune disease, e.g. naturally occurring TLR3 ligand such as dsRNA and/or the presence of, and in particular, high levels of, IFNα in the diseased cells. The antibodies will also have the advantage of binding TLR3 even if the TLR3 ligand binding site is occupied by a dsRNA molecule thus potentially allowing broader overall binding.

The present disclosure shows that the antibodies that bind human TLR3 under acidic conditions have a strong ability to modulate, particularly inhibit, TLR3 signaling in cells (myeloid dendritic cells (MdDC); monocyte derived DC (MoDC)) which express TLR3 solely or primarily in their cytoplasmic compartments, and primarily in compartments of the endocytic pathway (e.g. endosomes). The antibodies bind to a region in TLR3 which is not involved in binding to dsRNA, and the antibodies do not prevent dsRNA from binding to TLR3 under acidic conditions. The compositions and methods are useful for a multitude of applications, and are particularly well suited to modulating TLR3 signaling (e.g. in vivo) where cytosolic (e.g. endocytic pathway compartment-localized) TLR3 is targeted. Modulating cytosolic TLR3 signaling can be useful to treat or prevent a disease for which modulation of TLR3 signaling in DC or other cells that express TLR3 in acidic cytosolic compartments (e.g. in endosomes) is beneficial. For example, inhibiting TLR3 signaling in DC (e.g. as observed by inhibition of cytokine production by the DC) can be used the treatment or prevention of inflammatory or autoimmune disorders since DC have a well documented capacity to take up antigens from apoptotic or necrotic cells (Albert et al (2004) Nat. Rev. Immunol. 4: 223-231), including during tissue necrosis during acute inflammation (Cavassani et al. (2008). Optionally, the antibodies inhibit TLR3 signaling, e.g. inhibit cytokine production (e.g. IP10) induced by the stimulation of a TLR3 receptor by a TLR3 ligand.

Endosomes and lysosomes are membrane bound compartments inside cells, form part of the endocytic pathway and are usually acidic due to the action of a proton-pumping ATPase of the endosomal membrane. The earliest measurements of in situ lyosomal pH found a pH of 4.7-4.8 in macrophages; the pH of fibroblast endosomes involved in receptor-mediated endoxytosis was determined to be about 5.5. Early studies of TLR3 identified it as being expressed in the cytosol in monocyte-derived DCs and that it probably bound its ligand in subcellular compartments of the endocytic pathway (Matsumoto et al. (2003) J. Immunol. 171:3154-3162). TLR3 has since been reported to be expressed in cells' endosomal compartment in dendritic cells, astrocytes, macrophages, T cells, epithelial cells, fibroblasts and hepatocytes, although TLR3 has also been found on cell surface, particularly on epithelial cells, and in some cases of inflammation also on macrophages (Cavassani et al. 2008, supra). Endosomal acidification has been shown to have a role in TLR3 signaling since treatment with chloroquine, an inhibitor of endosomal acidification, inhibits TLR3 signaling in DC. The antibodies provided herein that bind TLR3 under acidic conditions corresponding to an acidified endosomic compartment (e.g. pH of about 5.6, or less than about 6.5) have the advantage of allowing efficient high affinity binding to, and optionally further modulation of, TLR3 in endosomic compartments compared to antibodies that lose their affinity under acidic conditions and thus may exert their effects more on cell surface TLR3. The antibodies exemplified have strong inhibitory activity on TLR3 in DC which are known for expressing TLR3 primarily in cytosomal compartments.

In one embodiment, the present invention provides monoclonal antibodies that specifically bind human TLR3 and inhibit TLR3 signaling, e.g. inhibit cytokine production induced by the stimulation of a TLR3 receptor by a TLR3 ligand, without blocking the binding of a ligand of TLR3 (e.g. a natural or synthetic ligand of TLR3, a nucleic acid based ligand, a dsRNA, viral dsRNA, polyIC, polyAU) to a TLR3 polypeptide. When TLR3 polypeptides are bound by such antibodies, dsRNA can still bind the TLR3 polypeptides, reducing dsRNA available to bind to remaining non antibody-bound TLR3 and/or other dsRNA receptors (i.e. RIG-I, MDA-5, TLR7, etc), thereby potentially reducing undesirable side effects such as increased toxicity, inappropriate signaling cascade activation and so on, and resulting conditions, e.g. chronic inflammation, that arise from dsRNA induced signaling. Such antibody compositions and methods are useful for a multitude of applications, particularly to treat or prevent a disease related to TLR3 signaling, and in view of their mechanism of action, the antibodies of the invention can be used for anergizing or inhibiting TLR3 polypeptides. Optionally, the antibody can be characterized as not detectably reducing the binding of a double-stranded RNA ligand of TLR3 to a TLR3 polypeptide. The antibody may or may not also be capable of binding with high affinity to human TLR3 under acidic conditions, e.g. under conditions representative of that encountered in an acidified endosomic compartment. In one embodiment, where an antibody is sought that can inhibit signaling by TLR3, it will be advantageous that an antibody that specifically binds TLR3 and inhibits TLR3 signaling without blocking the binding of a double-stranded RNA ligand of TLR3 to a TLR3 polypeptide can additionally be capable of binding and inhibiting human TLR3 under acidic conditions as described herein, and in particular under conditions representative of that encountered in an acidified endosomic compartment of a cell.

In one aspect of any of the embodiments of the invention, the antibody competes for binding to a TLR3 polypeptide with any one or any combination of monoclonal antibodies 31C3, 29H3, 23C8, 28F11 or 34A3, optionally under acid and/or neutral conditions. In one embodiment, an antibody of the invention competes for binding to a TLR3 polypeptide, optionally under acid and/or neutral conditions, with an antibody selected from the group consisting of:

(a) an antibody having respectively a VH and VL region of SEQ ID NOS 2 and 3 (31C3), (b) an antibody having respectively a VH and VL region of SEQ ID NOS 10 and 11 (29H3), (c) an antibody having respectively a VH and VL region of SEQ ID NOS 18 and 19 (28F11), (d) an antibody having respectively a VH and VL region of SEQ ID NOS 26 and 27 (23C8) and (e) an antibody having respectively a VH and VL region of SEQ ID NOS 34 and 35 (34A3).

In the foregoing aspect, the antibody may compete for binding to a TLR3 polypeptide with an antibody selected from the group consisting of: (a) an antibody having respectively a VH and VL region of SEQ ID NOS 2 and 3 (31C3), (b) an antibody having respectively a VH and VL region of SEQ ID NOS 10 and 11 (29H3), (c) an antibody having respectively a VH and VL region of SEQ ID NOS 18 and 19 (28F11), (d) an antibody having respectively a VH and VL region of SEQ ID NOS 26 and 27 (23C8) and (e) an antibody having respectively a VH and VL region of SEQ ID NOS 34 and 35 (34A3) under acid conditions. The antibody may be a monoclonal antibody. The antibody may be in a composition comprising a pharmaceutically acceptable carrier. Some aspects relate to a method for treating or preventing a disease wherein the inhibition of TLR3 signaling pathway is desirable comprising administering a therapeutically effective amount of an antibody of the foregoing aspects to a patient in need thereof.

The antibody may compete for binding to a TLR3 polypeptide with an antibody selected from the group consisting of: (a) an antibody having respectively a VH and VL region of SEQ ID NOS 2 and 3 (31C3), (b) an antibody having respectively a VH and VL region of SEQ ID NOS 10 and 11 (29H3), (c) an antibody having respectively a VH and VL region of SEQ ID NOS 18 and 19 (28F11), (d) an antibody having respectively a VH and VL region of SEQ ID NOS 26 and 27 (23C8) and (e) an antibody having respectively a VH and VL region of SEQ ID NOS 34 and 35 (34A3) under neutral conditions. The antibody may be a monoclonal antibody. The antibody may be in a composition comprising a pharmaceutically acceptable carrier. Some aspects relate to a method for treating or preventing a disease wherein the inhibition of TLR3 signaling pathway is desirable comprising administering a therapeutically effective amount of an antibody of the foregoing aspects to a patient in need thereof.

Any of the antibodies described herein may be used in a method for treating or preventing a disease wherein the inhibition of TLR3 signaling pathway is desirable comprising administering a therapeutically effective amount of the antibody to a patient in need thereof. In some aspects, the disease is selected from the group consisting of autoimmunity, inflammation, allergy, asthma, infection, cirrhosis, sepsis, diabetes, and viral infections.

In one embodiment the antibody competes for binding to a TLR3 polypeptide with antibodies 31C3 and 29H3; in one embodiment the antibody competes for binding to a TLR3 polypeptide with antibodies 31C3 and 23C8; in one embodiment the antibody competes for binding to a TLR3 polypeptide with antibodies 31C3 and 28F11; in one embodiment the antibody competes for binding to a TLR3 polypeptide with antibodies 31C3 and 34A3. In one embodiment the antibody competes for binding to a TLR3 polypeptide with antibodies 29H3 and 23C8; in one embodiment the antibody competes for binding to a TLR3 polypeptide with antibodies 29H3 and 28F11; in one embodiment the antibody competes for binding to a TLR3 polypeptide with antibodies 29H3 and 34A3. In one embodiment the antibody competes for binding to a TLR3 polypeptide with antibodies 23C8 and 28F11; in one embodiment the antibody competes for binding to a TLR3 polypeptide with antibodies 23C8 and 34A3. In one embodiment the antibody competes for binding to a TLR3 polypeptide with antibodies 28F11 and 34A3.

In one embodiment, the antibody of the invention comprises a light chain comprising:
(a) a light chain CDR1 (LCDR1) amino acid sequence selected from SEQ ID NOS: 61, 64 and 65;
(b) a light chain CDR2 (LCDR2) amino acid sequence selected from SEQ ID NOS: 62, 66 and 67; and/or
(c) a light chain CDR3 (LCDR3) amino acid sequence selected from SEQ ID NOS: 63, 68, 69 and 70.

In one embodiment, the antibody of the invention comprises a heavy chain comprising:
(a) a heavy chain CDR1 (HCDR1) amino acid sequence selected from SEQ ID NOS: 71 to 76;
(b) a heavy chain CDR2 (HCDR2) amino acid sequence selected from SEQ ID NOS: 77 to 81; and/or
(c) a heavy chain CDR3 (HCDR3) amino acid sequence selected from SEQ ID NOS: 82 to 85.

In one embodiment, the antibody of the invention is selected from the group consisting of:
(a) an antibody having (i) the heavy chain CDR 1, 2 and 3 (HCDR1, HCDR2, HCDR3) amino acid sequences as shown in SEQ ID NO: 4, 5 and 6, and (ii) the light chain CDR 1, 2 and 3 (LCDR1, LCDR2, LCDR3) amino acid sequences as shown in SEQ ID NO: 7, 8 and 9, respectively;
(b) an antibody having (i) the heavy chain CDR 1, 2 and 3 (HCDR1, HCDR2, HCDR3) amino acid sequences as shown in SEQ ID NO: 12, 13 and 14, and (ii) the light chain CDR 1, 2 and 3 (LCDR1, LCDR2, LCDR3) amino acid sequences as shown in SEQ ID NO: 15, 16 and 17, respectively;
(c) an antibody having (i) the heavy chain CDR 1, 2 and 3 (HCDR1, HCDR2, HCDR3) amino acid sequences as shown in SEQ ID NO: 20, 21 and 22, and (ii) the light chain CDR 1, 2 and 3 (LCDR1, LCDR2, LCDR3) amino acid sequences as shown in SEQ ID NO: 23, 24 and 25, respectively;
(d) an antibody having (i) the heavy chain CDR 1, 2 and 3 (HCDR1, HCDR2, HCDR3) amino acid sequences as shown in SEQ ID NO: 28, 29 and 30, and (ii) the light chain CDR 1, 2 and 3 (LCDR1, LCDR2, LCDR3) amino acid sequences as shown in SEQ ID NO: 31, 32 and 33, respectively; and
(e) an antibody having (i) the heavy chain CDR 1, 2 and 3 (HCDR1, HCDR2, HCDR3) amino acid sequences as shown in SEQ ID NO: 36, 37 and 38, and (ii) the light chain CDR 1, 2 and 3 (LCDR1, LCDR2, LCDR3) amino acid sequences as shown in SEQ ID NO: 39, 40 and 41, respectively;
optionally wherein one, two, three or more of the amino acids in any of said sequences may be substituted by a different amino acid.

In one embodiment of the invention, the antibody binds to the same TLR3 epitope as any one or any combination of monoclonal antibodies 31C3, 29H3, 23C8, 28F11 or 34A3. In another embodiment, the antibody comprises an antigen binding region of antibody 31C3. In another embodiment, the antibody comprises an antigen binding region of antibody 29H3. In another embodiment, the antibody comprises an antigen binding region of antibody 23C8. In another embodiment, the antibody comprises an antigen binding region of antibody 28F11. In another embodiment, the antibody comprises an antigen binding region of antibody 34A3. In another embodiment, the antibody comprises a light chain comprising one, two or all three CDRs of the 31C3, 29H3, 23C8, 28F11 or 34A3 light chain variable region sequence, and/or a heavy chain comprising one, two or all three CDRs of the 31C3, 29H3, 23C8, 28F11 or 34A3 heavy chain variable region sequence. In another embodiment, the antibody is 31C3, 29H3, 23C8, 28F11 or 34A3 or a fragment or derivative thereof, optionally fused to a human Fc region. Antibodies 29H3.7 and 31C3.1 have been deposited at the Collection Nationale de Culture de Microorganismes (CNCM), Institut Pasteur, 25 rue de Docteur Roux, F-75724 Paris on 3 Jul. 2009, under the number CNCM I-4187 and CNCM I-4186 respectively. Antigen binding regions of antibodies 31C3, 29H3, 23C8, 28F11 or 34A3 are also disclosed in SEQ ID NOS 2 to 41.

In one aspect of the invention, the light chain of one antibody according to the present invention is obtained from or encoded by a nucleic acid sequence derived from a VL gene rearrangement selected from VK 19-14, VK aq4, VK 12-41 and VK 12-44 for the V gene, and JK2 for the J gene.

In one aspect of the invention, the heavy chain of one antibody according to the present invention is obtained from or encoded by a nucleic acid sequence derived from a VH gene rearrangement selected from VH36-60.a1.85, VH L558.1 and VH J558.2 for the V gene, and JH4 or JH2 for the J gene.

In another aspect of the invention, the antibody has one or more CDRs of the sequence selected from the group consisting of SEQ ID NOS: 4 to 9, 12 to 17, 20 to 25, 28 to 33, 36 to 41, wherein one, two, three or more of these amino acids may be substituted by a different amino acid.

In another aspect, the invention provides an antibody that specifically binds TLR3, wherein the antibody has one or more of the following properties:

a. has a subnanomolar affinity for a TLR3 polypeptide at an acidic pH, e.g. a pH less than about 6.5, or between about 4.5 to 6.5 or about pH 5.6; or
b. is able to inhibit TLR3 signaling in the presence of a TLR3 ligand; or
c. is able to inhibit TLR3 signaling in an inflammatory background, e.g. in the presence of inflammatory cytokines such as IFN$\alpha$; or
d. competes for binding to a TLR3 polypeptide with 31C3, 29H3, 28F11, 23C8 or 34A3;
e. does not compete with dsRNA for binding to a TLR3 polypeptide.

In one embodiment, the antibody has above-listed properties (a) and (b); (a), (b) and (c); (a), (b), (c) and (d); or (a), (b), (c), (d) and (e). In one embodiment, the antibody has properties (a) and (c); (a), (c) and (d); or (a), (c), (d) and (e). In one embodiment, the antibody has properties (a) and (d); (a) and (e); or (a), (d) and (e). In one embodiment, the antibody has properties (b) and (c); (b), (c) and (d); or (b), (c), (d) and (e). In one embodiment, the antibody has properties (b) and (d); (b) and (e); or (b), (d) and (e). In one embodiment, the antibody has properties (c) and (d); (c) and (e); or (c), (d) and (e). In one embodiment, the antibody has properties (d) and (e). In another embodiment, the antibody additionally has any of the properties of anti-TLR3 antibodies described herein.

In another embodiment, the antibody of any of the embodiments herein is capable of being internalized by a cell that expresses TLR3 polypeptide on its surface.

In an embodiment of any aspect of the invention, the amino acid sequences listed in the SEQ IDs comprise one, two, three or more amino acid substitution. In another embodiment, in any embodiment of the invention, the embodiment may encompass an amino acid sequence may have at least 95%, 97%, 98%, or 99% identity with an amino acid sequence in a particular SEQ ID NO.

In another embodiment, the invention provides a monoclonal anti-TLR3 antibody that has the same epitopic specificity as an antibody selected from the group consisting of 31C3, 29H3, 28F11, 23C8 and 34A3.

In one embodiment, the antibody is chimeric, e.g. contains a non-murine, optionally a human, constant region. In one embodiment, the antibody is human or humanized. In another embodiment, the antibody is a mouse antibody. In another embodiment, the antibody does not substantially bind to other human TLRs (e.g. TLR4).

In one aspect of any of the embodiments of the invention, the isotype of the antibody is IgG, optionally IgG1 or IgG3. In one embodiment the antibody comprises an Fc domain or is of an isotype that is bound by Fc$\gamma$R.

In one aspect of any of the embodiments of the invention, the antibody is an antibody fragment selected from Fab, Fab', Fab'-SH, F(ab')2, Fv, diabodies, single-chain antibody fragment, or a multispecific antibody comprising multiple different antibody fragments. In one aspect of any of the embodiments of the invention, the antibody does not comprise an Fc domain or is of an isotype that is not substantially bound by Fc$\gamma$R. In one embodiment, the antibody is of an IgG4 or IgG2 isotype. As demonstrated in the Examples, F(ab')2 fragments of the antibodies of the present invention retained their ability to modulate TLR3 signaling in DCs and were thus taken up by DC despite their lack of Fc domain. It has previously generally been thought that antibodies will enter the endosomal pathway in DC at least in part by Fc receptor-mediated uptake (human DC express several types of Fc$\gamma$ receptors (Fc$\gamma$R), including type I (Fc$\gamma$RI, CD64) and type II (Fc$\gamma$RII, CD32)). The finding that isotypes and formats that do not bind Fc$\gamma$R can modulate TLR3 in DC enables antibodies to be developed that retain desired characteristics without a risk of inducing unwanted depletion (e.g. via Fc$\gamma$R-mediated antibody dependent cellular cytotoxicity) of TLR3-expressing cells. For example IgG4 isotypes or other IgG isotypes modified to reduce their Fc$\gamma$R binding can be used for their advantageous pharmacological properties such as serum half-life, while modulating TLR3 signaling, in e.g. a DC, without induce the death of the cell. In one aspect of any of the embodiments of the invention, the anti-TLR3 antibody inhibits TLR3 signaling and comprises a constant region of IgG4 or IgG2 isotype. In one aspect, of any of the embodiments of the invention, the anti-TLR3 antibody inhibits TLR3 signaling and comprises a constant region that does not substantially bind Fc$\gamma$R.

In another embodiment, the antibody is conjugated or covalently bound to a detectable or toxic moiety.

In another aspect, the present invention provides a cell, e.g. a hybridoma or recombinant host cell, producing an anti-TLR3 antibody of the invention. In one embodiment, the cell is clone 31C3, 29H3, 23C8, 28F11 or 34A3. In a related aspect, the present invention provides a hybridoma comprising: a) a B cell from a non-human mammalian host that has been immunized with an antigen that comprises the TLR3 epitope specifically recognized by the 31C3, 29H3, 23C8, 28F11 or 34A3 antibody, fused to b) an immortalized cell, wherein the hybridoma produces a monoclonal antibody that specifically binds to the epitope. In one embodiment of these aspects, the monoclonal antibody binds to the same epitope as antibody 31C3, 29H3, 23C8, 28F11 or 34A3. Optionally, the cell produces an antibody having the antigen binding region of antibody 31C3, 29H3, 23C8, 28F11 or 34A3.

In another aspect, the present invention provides a method of testing an antibody, the method comprising the steps of: testing an antibody to determine whether it:

a) inhibits TLR3 signaling, optionally without blocking the binding of a TLR3 ligand (e.g. dsRNA) to a TLR3 polypeptide, and/or
b) competes for binding to a TLR3 polypeptide with antibody 31C3, 29H3, 23C8, 28F11 or 34A3, and/or
c) binds human TLR3 under acidic conditions, and in particular under conditions representative of that encountered in an acidified subcellular compartment of a cell of a cell, e.g. about pH 5.6, between about pH 4.5 and about 6.5; optionally wherein the affinity for TLR3 under acidic conditions is not substantially different, e.g. reduced, compared to binding under neutral conditions.

Optionally, the method comprises testing an antibody according to substeps (a) and (b), substeps (a) and (c), substeps (b) and (c) or substeps (a), (b) and (c).

Optionally the method further comprises a step of selecting the antibody if it is determined to inhibit TLR3 signaling, if it is determined to compete for binding to a TLR3 polypeptide with antibody 31C3, 29H3, 23C8, 28F11 or 34A3, and/or if it is determined to bind human TLR3 under acidic conditions and/or without a reduction in affinity compared to neutral conditions. Optionally the antibody is further tested for its ability to modulate, e.g. inhibit, TLR3 signaling in a dendritic cell, and selected if the antibody is determined to modulate TLR3 signaling in a DC. Optionally, the antibody so selected is selected for use in the treatment or prevention of a disease (e.g. an antibody that inhibits TLR3 signaling will be used in inflammatory and autoimmune disorders). Optionally, a quantity of the antibody so selected is produced (e.g. in a recombinant host cell).

In another aspect, the present invention provides a method of producing an antibody that specifically binds to TLR3 in a mammalian subject, particularly in a human subject, said method comprising the steps of generating a plurality of antibodies (e.g. by immunizing a non-human mammal with an immunogen comprising a TLR3 polypeptide); and selecting an antibody from said plurality that:

a) inhibits TLR3 signaling, optionally without blocking the binding of a TLR3 ligand (e.g. dsRNA) to a TLR3 polypeptide, and/or
b) competes for binding to a TLR3 polypeptide with antibody 31C3, 29H3, 23C8, 28F11 or 34A3, and/or
c) binds human TLR3 under acidic conditions, and in particular under conditions representative of that encountered in an acidified subcellular compartment of a cell of a cell, e.g. about pH 5.6, between about pH 4.5 and about 6.5; optionally wherein the affinity for TLR3 under acidic conditions is not substantially different, e.g. reduced, compared to binding under neutral conditions.

Optionally, the method comprises selecting an antibody according to substeps (a) and (b), substeps (a) and (c), substeps (b) and (c) or substeps (a), (b) and (c). Optionally the method further comprises selecting an antibody that has ability to modulate, e.g. inhibit, TLR3 signaling in a dendritic cell, and selected if the antibody is determined to modulate TLR3 signaling in a DC.

In another aspect, the present invention provides a method of testing an antibody comprising: a) providing a test antibody; and b) assessing whether said test antibody induces a decrease in the expression of TLR3 at the surface of cells, c) if said antibody does not induces a decrease in the expression of TLR3 at the surface of cells, selecting said test antibody as a candidate for the treatment of a disease (e.g. any of the diseases disclosed herein).

In another aspect, the present invention provides a method of testing an antibody comprising: a) providing a test antibody; b) assessing the binding affinity of said test antibody under acidic conditions, e.g., at a pH of 5.6; and c) if said antibody has a binding affinity in acidic conditions (e.g., subnanomoral affinity, no substantial decrease in affinity compared to at neutral conditions, etc.), selecting said test antibody as a candidate for the treatment of a disease.

In another aspect, the present invention provides a method of testing an antibody comprising: a) providing a test antibody; b) assessing whether said test antibody is able to bind TLR3 protein in the presence of a TLR3 ligand, e.g. dsRNA; and c) if said antibody is able to bind TLR3 protein in the presence of a TLR3 ligand, selecting said test antibody as a candidate for the treatment of a disease.

In another aspect, the present invention provides a method of selecting an antibody comprising: a) providing a test antibody; b) assessing whether said test antibody is able to bind TLR3 protein in the presence of inflammatory cytokines, i.e. IFNα; and c) selecting said test antibody as a candidate for the treatment of a disease.

In another aspect, the present invention provides a method of testing an antibody comprising: a) providing a test antibody; b) assessing whether said test antibody is capable of being internalized, e.g. by a TLR3-expressing cell; and c) if said antibody is capable of being internalized, preferably wherein the antibody rapidly internalized, e.g., within 2 hours, selecting said test antibody as a candidate for the treatment of a diseases. In one embodiment, the disease is an inflammatory disorder. In one embodiment, the disease is a cancer.

In one embodiment, the antibodies prepared are monoclonal antibodies. In another embodiment, the method further comprise a step in which the ability of said antibodies to specifically bind to human TLR3 polypeptides is assessed. In one embodiment, the ability of the antibodies to bind to other TLR family members is assessed. In another embodiment, the method further comprises the step of making fragments or derivatives of the selected monoclonal antibodies. In one embodiment, the fragments or derivatives are selected from the group consisting of Fab, Fab', Fab'-SH, F (ab') 2, Fv, diabodies, single-chain antibody fragment, multispecific antibodies comprising multiple different antibody fragments, humanized antibodies, and chimeric antibodies. In another embodiment, the non-human mammal is a mouse.

In another aspect, the present invention provides a method of treating or preventing disease in a patient comprising administering a TLR3 antibody of the invention to the patient. In another embodiment, the method further comprises the step of administering to the patient an appropriate additional therapeutic agent, for example particularly when the TLR3 antibody inhibits TLR3 signaling, an additional agent can be selected from the group consisting of immunomodulatory agents, corticosteroids, immunosuppressants, antibiotics, anti-inflammatory agents, and the like. Particularly when the TLR3 antibody is internalized by a TLR3-expressing cell and/or linked to a toxin or cytotoxic drug in order to eliminate a TLR3-expressing cell (e.g., a cancer cell), an additional agent can be selected from the group consisting of an anti-cancer agent, a cytotoxic agent, and the like. In one aspect the invention provides a method for treating or preventing a disease selected from autoimmunity, inflammation, allergy, asthma, infections, osteoporosis, cirrhosis and sepsis, cancer or other diseases contemplated herein, comprising administering a therapeutically effective amount of an inhibitory TLR3 antibody to a patient in need thereof. The antibody is administered for a time sufficient to treat or prevent said disease.

In one embodiment, the antibodies of the invention can be used in diagnostics assays or more generally any assays to detect TLR3 polypeptides in vitro. In one aspect the present invention provides an in vitro method of detecting a TLR3 polypeptide (e.g. in a biological sample) comprising bringing a TLR3 polypeptide (e.g. a cell expressing a TLR3 polypeptide, a purified TLR3 polypeptide, a biological sample, etc.) into contact with a monoclonal antibody of the invention, and detecting binding of the antibody to the TLR3 polypeptide.

One embodiment is an isolated antibody which competes for binding to a TLR3 polypeptide with any one or any combination of monoclonal antibodies 31C3, 29H3, 23C8, 28F11 or 34A3. In some aspects of this embodiment, the antibody competes for binding to a TLR3 polypeptide with any one or any combination of monoclonal antibodies 31C3, 29H3, 23C8, 28F11 or 34A3 under acid conditions. In other aspects of this embodiment, the antibody competes for binding to a TLR3 polypeptide with any one or any combination of monoclonal antibodies 31C3, 29H3, 23C8, 28F11 or 34A3 under neutral conditions. In further aspects, the antibody is a monoclonal antibody.

One embodiment is a method for treating or preventing a disease wherein the inhibition of TLR3 signaling pathway is desirable comprising administering a therapeutically effective amount of any of the antibodies described herein to a patient in need thereof. In some aspects, the disease is selected from the group consisting of autoimmunity, inflammation, allergy, asthma, infection, cirrhosis, sepsis, diabetes, and viral infections.

One embodiment is an isolated antibody which is specific for an epitope in the TLR-3 polypeptide that does not undergo substantial change in electrostatic potential or undergoes less change than a region of positive electrostatic potential when neutral conditions are acidified such that the binding affinity of said antibody remains substantially unchanged. In some aspects, the antibody may be in a composition comprising a pharmaceutically acceptable carrier. The antibody may be used in a method for treating or preventing a disease wherein the inhibition of TLR3 signaling pathway is desirable comprising administering a therapeutically effective amount of the antibody to a patient in need thereof. In some aspects, the disease is selected from the group consisting of autoimmunity, inflammation, allergy, asthma, infection, cirrhosis, sepsis, diabetes, and viral infections.

One embodiment is an isolated antibody which specifically binds to the same TLR3 epitope as any one or any combination of monoclonal antibodies 31C3, 29H3, 23C8, 28F11 or 34A3. In some aspects, the antibody may be in a composition comprising a pharmaceutically acceptable carrier. The antibody may be used in a for treating or preventing a disease wherein the inhibition of TLR3 signaling pathway is desirable comprising administering a therapeutically effective amount of the antibody to a patient in need thereof. In some aspects, the disease is selected from the group consisting of autoimmunity, inflammation, allergy, asthma, infection, cirrhosis, sepsis, diabetes, and viral infections.

These and additional advantageous aspects and features of the invention may be further described elsewhere herein.

BRIEF DESCRIPTION OF THE DRAWINGS

FIG. 1 shows the inhibition of TLR3 activation markers on myeloid DC.

FIG. 2 shows the inhibition of TLR3 activation markers on MdDC.

FIG. 3 shows the inhibition of TLR3 activation markers on myeloid DC, comparing F(ab)'2 fragments of antibody 31C3 to purified whole 31C3 antibodies (indicated by "Pur").

FIG. 4 shows the inhibition of TLR3 activation markers on MdDC, comparing F(ab)'2 fragments of antibody 29H3 to purified whole 29H3 antibodies (indicated by "Pur").

FIG. 11A represents the inhibition of TLR3 signaling, in the standard conditions (no preactivation). FIG. 11B represents inhibition of TLR3 signaling, with a polyAU prestimulation. FIG. 11C represents inbihition of TLR3 signaling with a IFNα prestimulation.

FIG. 12 shows the results the kinetics assays.

FIG. 14 shows the inhibition of TLR3-induced activation markers and cytokine secretion on myeloid DC.

(black dots), 28F11 (black triangles) and 23C8 (black squares) (here shown at a dose of 50 µg/ml) inhibit TLR3 ligand-induced response.

Figure 15A:
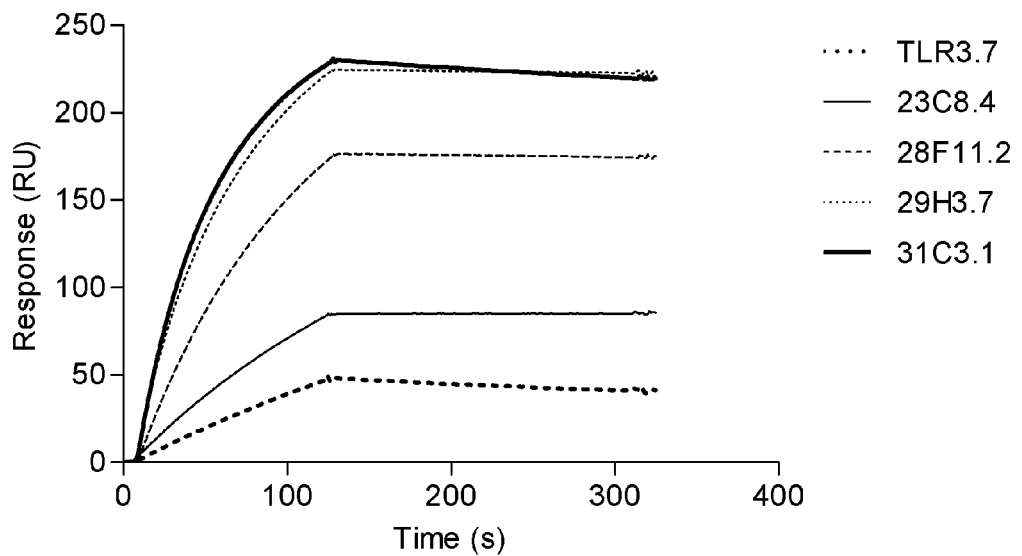
Figure 15B:
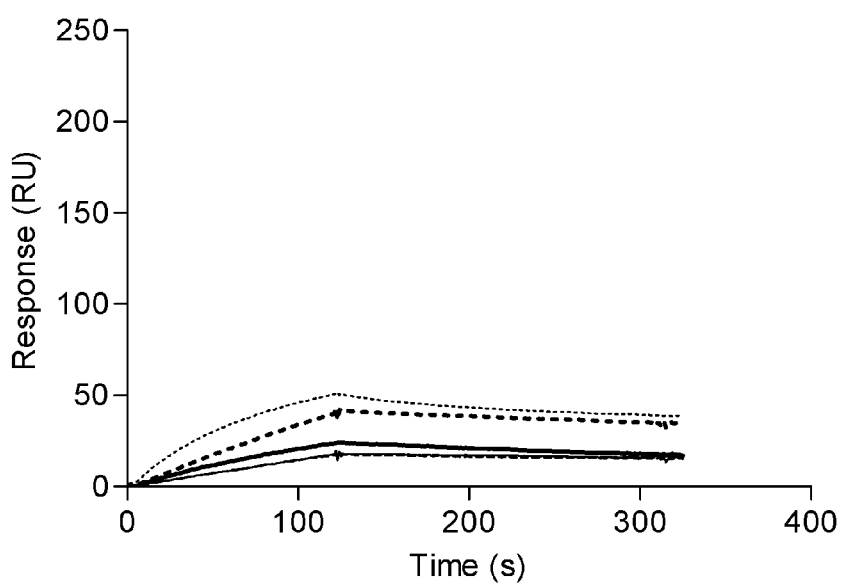

FIGS. 15A and 15B show the binding affinity of the antibodies according to the invention. FIG. 15A shows that the antibodies according to the present invention have a stronger binding for the TLR3 chip than commercially available (i.e. TLR3.7) antibodies. FIG. 15B shows the binding of the antibodies according to the invention on a TLR3 chip when said chip has been previously saturated with the 31C3 antibody. A comparison of binding levels as set forth in FIGS. 15A and 15B underline that the antibodies according to the invention have an impaired binding to hTLR3 when the chip has previously been saturated with the 31C3 antibody, on the contrary, the commercial TLR3.7 antibody retains the same binding level in the presence or in the absence of 31C3 antibody.

Figure 16A:
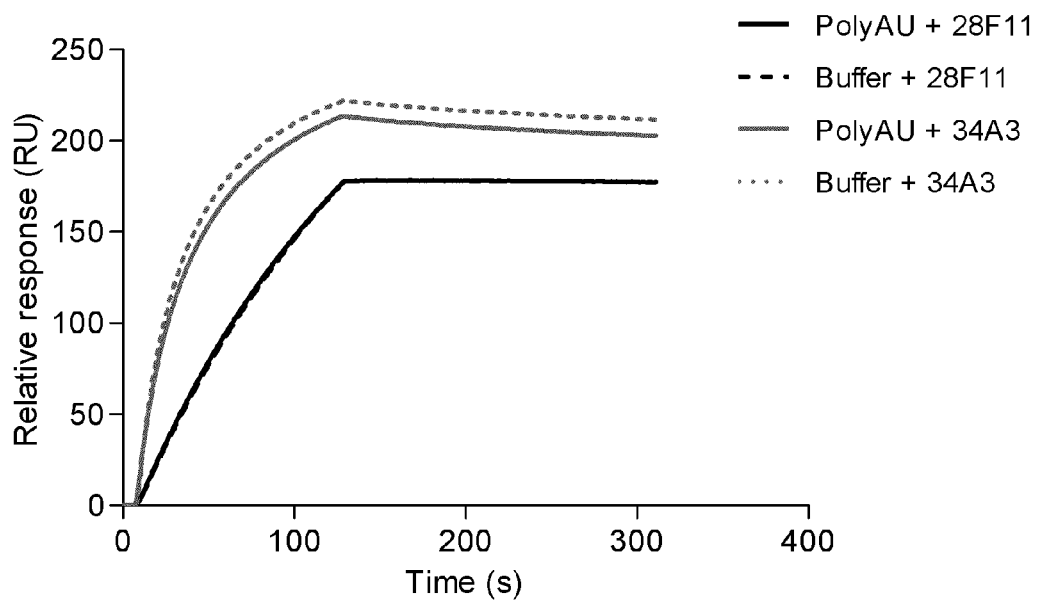
Figure 16B:
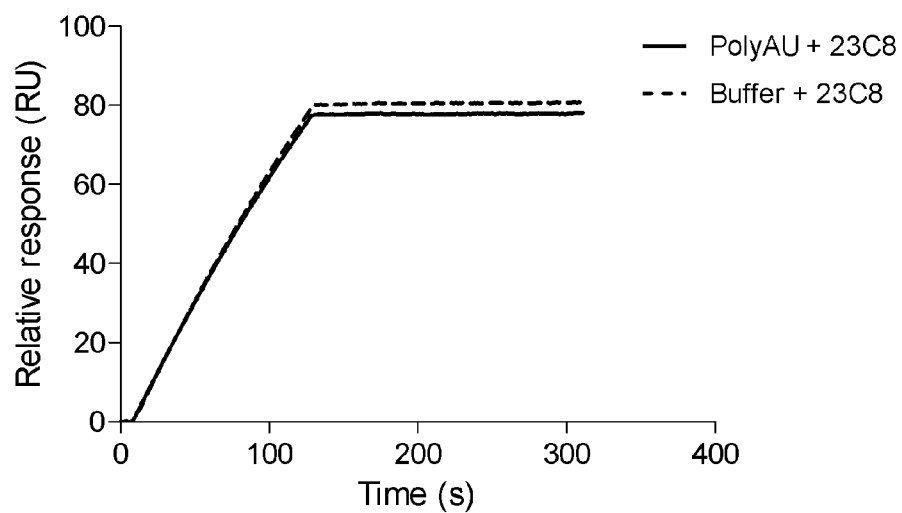

FIGS. 16A and 16B show the binding of the 28F11, 34A3 and 23C8 antibodies according to the invention on a TLR3 chip in the presence or in the absence of polyAU, a ligand for TLR3 receptors. The figures show that the binding of the antibodies of the invention do not block dsRNA binding to the TLR3 dsRNA fixation site.

Figure 17:
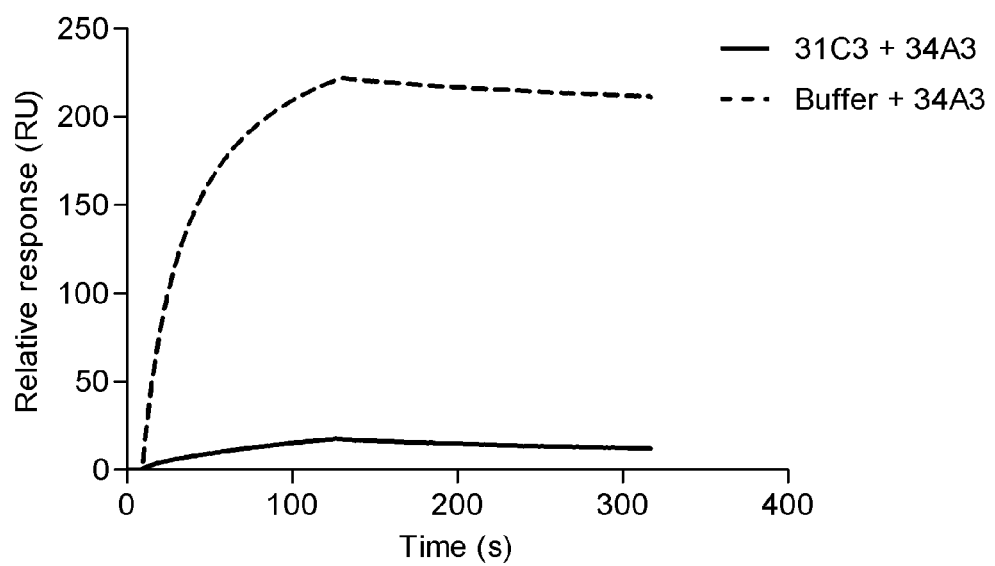

FIG. 17 shows the binding of the 34A3 antibody, either alone on rhTLR3 (bold line or on a chip saturated with 31C3 (dotted line). The figure shows that the two antibodies compete with 31C3 for binding to hTLR3.

Figure 18A:
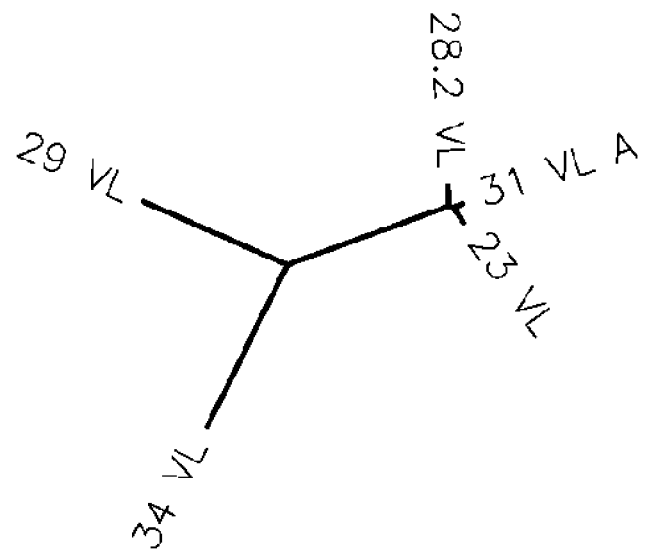
Figure 18B:
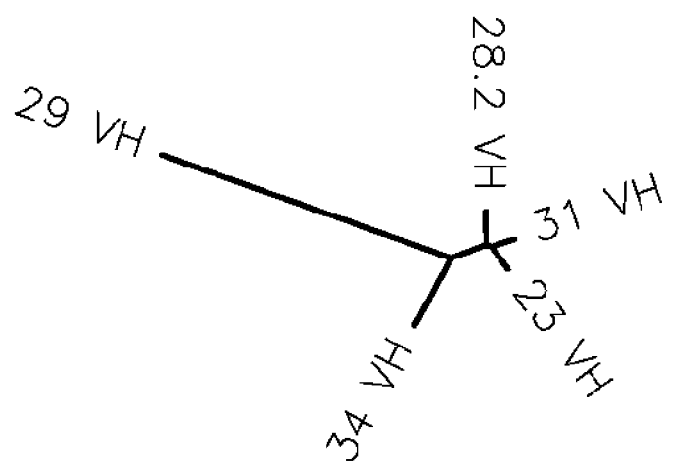

FIG. 18 shows the phylogenetic trees of the CDRs of the antibodies according to the invention. FIG. 18A shows the phylogenetic tree for the light chains CDRs and FIG. 18B shows the phylogenetic tree for the heavy chains CDRs. The figures show that there is a high CDR homology between antibodies 28F11 (28.2), 31C3 (31) and 23C8(23), and that 23H3 (29) and 34A3 (34) have more differences in amino acid sequences.

Figure 19A:
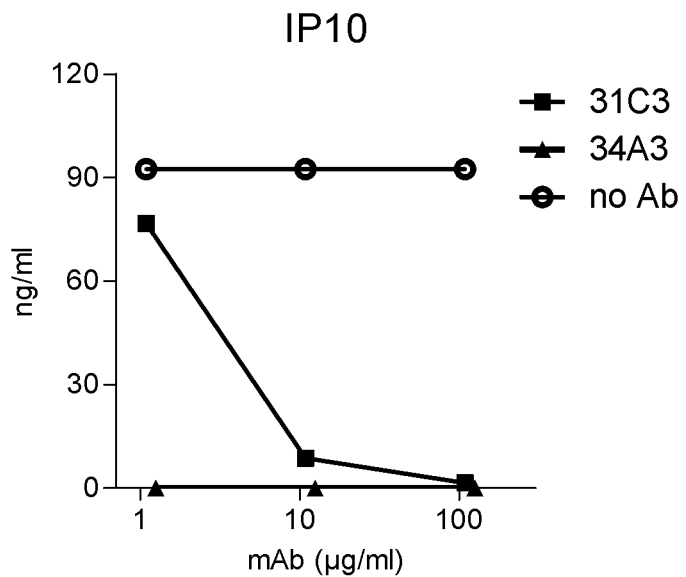

FIGS. 19A and B show the inhibition of TLR3 activation markers on myeloid DC by the 34A3 antibody. FIG. 19A: IP-10 secretion, FIG. 19B: IL-6 secretion. All figures show that compared to control (no Ab—open dots) and 31C3 (black squares, as positive control), the antibody 34A3 (black triangles) inhibits TLR3 ligand-induced response.

FIG. 20 shows the FACS analysis of internalization assays as described in example 8. FIG. 20A represents the negative control, representing standard fluorescence of the 293T-ISRE/TLR3 cells in the absence of an antibody linking TLR3 proteins. FIG. 20B is the positive control, indicating the level of TLR3 expression in 293T-ISRE/TLR3 cell lines. FIGS. 20 C and D represent the proportion of TLR3 proteins coupled with the 31C3 antibody after 24 h or 2 h incubation, respectively. FIGS. 20D and 20E, showing a similar fluorescence than FIG. 20B confirm that the binding of TLR3 by antibody 31C3 does not down-modulate the expression of TLR3 on 293T-ISRE/TLR3 cell lines.

DETAILED DESCRIPTION OF THE INVENTION

Introduction

The present invention provides novel methods for producing and using antibodies and particularly TLR3-modulating antibodies suitable for the prophylaxis and treatment of disorders such as autoimmunity, inflammation, allergy, asthma, cirrhosis, osteoporosis, infection, cancers and sepsis. Antibodies, antibody derivatives, antibody fragments, and cells producing them are encompassed, as are methods of producing the same and methods of treating or diagnosing patients using the antibodies and compounds.

While high affinity is desirable in antibodies, generally all antibodies reported to have affinities in the high picomolar to low nanomolar range have been affinity matured in vitro. The scientific literature has proposed that there is an in vivo affinity ceiling at 100 pM and that this might arise because B cells producing antibodies with affinities for antigen above the estimated ceiling would have no selective advantage during normal immune responses. However, examples of high affinity antibodies exist, including the anti-TNF-alpha antibody "TSK114" which binds to human TNF-alpha with a binding affinity (K(D)) of approximately 5.3 pM, which was stated to be about 1,000- and 100-fold higher than those of clinically relevant infliximab (Remicade) and adalimumab (Humira) mAbs (Song et al. (2008) Exp. Mol. Med. 40(1): 35-42. It is possible that obtaining high affinity antibodies depends on the antigen; yet the TLR3 antibodies available to date have at best shown nanomolar affinity. The present anti-TLR3 antibodies however demonstrated very high affinity (as high as 10 picomolar and better than 100 picomolar, including for two antibodies that maintained such affinity at both neutral and acid conditions).

The present invention is based, at least in part, on the discovery of monoclonal antibodies that specifically and efficiently bind TLR3 under acidic conditions corresponding to that encountered in an acidified endosomic compartment. Among numerous antibodies assessed, certain antibodies emerged that retained binding to TLR3 at high affinities under acidic conditions, while other antibodies such as those available commercially and others selected for TLR3 binding or TLR3 modulation lost affinity despite initially displaying higher (e.g. 2-$\log_{10}$ higher) affinity for TLR3, and/or had low affinity even under neutral conditions. Acidic conditions used were pH 5.6 which is similar to that observed in an acidified endosomic compartment, corresponding to the conditions under which TLR3 signaling in inflammatory conditions is believed to take place.

Acidic conditions are generally known to affect the structure of proteins as well as to affect protein-protein interactions. It is known, for example, that MHC class II peptides that are not bound to other peptides are rapidly degraded in the acidic conditions of the endosome. However, in the present case the antibodies that lost their high binding affinity to immobilized TLR3 under acidic conditions of pH 5.6 had been previously purified under acidic conditions (pH 3). Without wishing to be bound by theory, this suggests that the loss of binding affinity arose not from inherent instability (degradation) of the antibody at acid conditions, but rather from modifications in the interaction between the antibodies and their target antigens.

Figure 8:
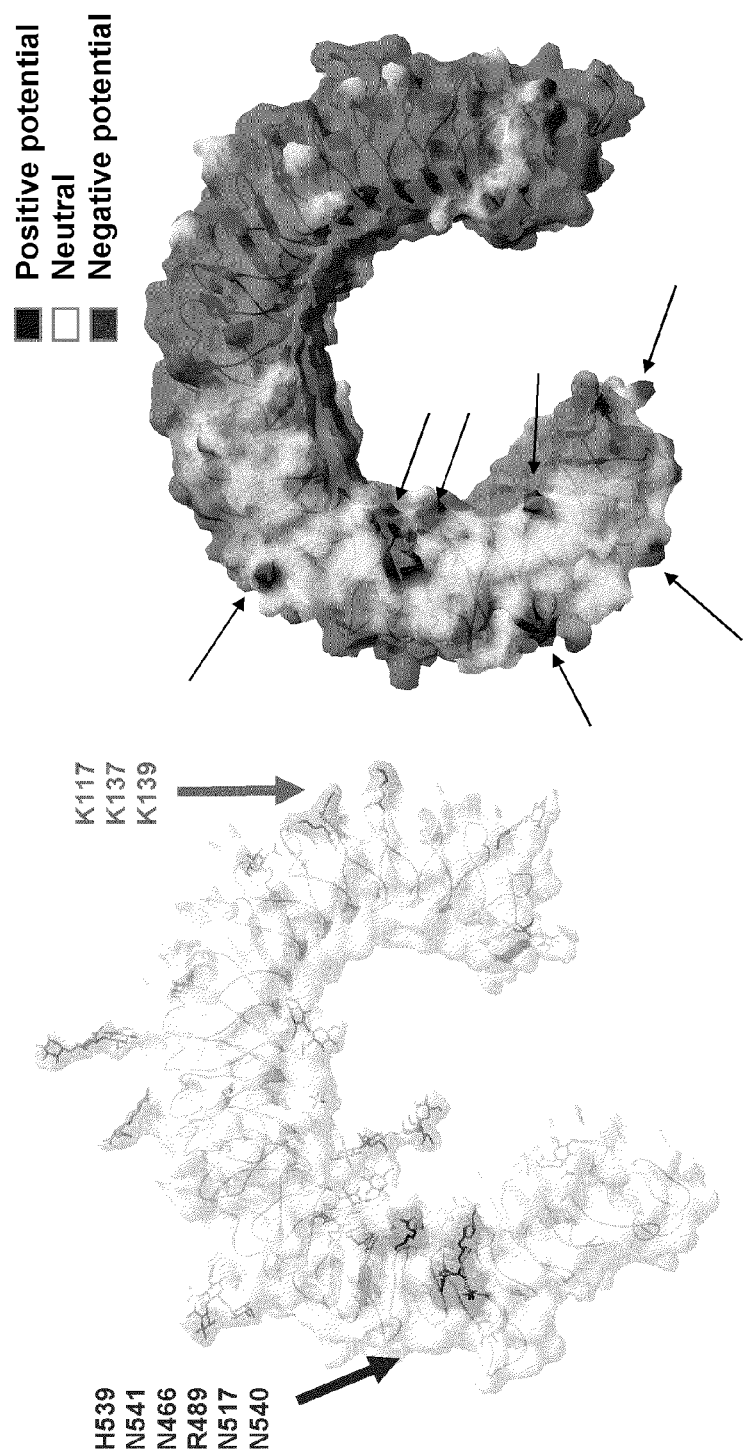
FIG. 8 shows molecular surface maps of the extracellular domains of the human TLR3 protein, generated by computer modeling.

Modifications in antibody-TLR3 interactions arising from changes in pH are believed to affect interactions of dsRNA with TLR3, since the TLR3 ligand poly(I-C) binds and activates TLR3 only at acidic pH. Studies have reported that poly(I-C) (and other dsRNA) bind TLR3 in a region of TLR3 of positive electrostatic potential at neutral pH that can undergo a change in electrostatic potential in acidic conditions (that is, acidic conditions in the range of pH 4.5 to 6.5, or around 5.6). The present antibodies, however, are believed to bind an epitope that does not undergo substantial change in electrostatic potential (or undergoes less change than e.g. a region of positive electrostatic potential) when conditions are acidified such that the binding affinity of the antibodies remains substantially unchanged. This can, in one aspect, manifest itself in terms of affinity of the antibodies for TLR3, since the antibodies do not have substantially different (lower and/or higher) affinity for binding human TLR3 under acidic conditions than under neutral conditions e.g. where the $K_D$ for binding to TLR3 differs by no more than 0.2-, 0.3-, 0.4-, 0.5-, 1.0-, or 1.5-$\log_{10}$. The $K_D$ for binding to TLR3 under acid and neutral conditions differed by less than 0.5-$\log_{10}$ for antibodies 31C3 and 29H7. It is believed that the epitope to which the antibodies of the invention bind may have negative electrostatic potential at neutral pH. Regions of negative, positive or neutral electrostatic potential on the surface of the TLR3 protein are shown in FIG. 8 or in also shown in FIG. 5D of Choe et al. (2005) Science 309:581-585, the disclosure of which is incorporated herein by reference. Whereas antibodies that inhibit TLR3 by interfering with binding of dsRNA ligands to TLR3 will be likely to bind to a region of positive or neutral electrostatic potential near the C-terminal on the glycosylation-free face of TLR3 and therefore bind in a region of TLR3 that can undergo a greater change in electrostatic potential, the present antibodies appear to bind to a region in TLR3 not involved in binding to dsRNA ligands, while nevertheless retaining the ability to inhibit signaling by the TLR3 protein, e.g. by inhibiting TLR3 from adopting a conformation required for ultimately transducing a signal.

The present invention is also based, at least in part, on the discovery of high affinity monoclonal antibodies that specifically and efficiently inhibit the TLR3 signaling pathway. The inventors have identified epitopes present on human TLR3, including the epitope recognized by antibody 31C3, 29H3, 23C8, 28F11 or 34A3, which are particularly efficient in inhibiting TLR3 signaling, and inhibiting cytokine release in response to stimulation with a TLR3 ligand.

The antibodies of the invention that inhibit TLR3 signaling will be particularly useful in treating and/or preventing autoimmune diseases, inflammatory disease and other diseases where inhibiting TLR3 signaling is beneficial. Autoimmune and inflammatory diseases arise from an overactive immune response of the body against substances and tissues normally present in the body. In both autoimmune and inflammatory diseases the condition arises through aberrant reactions of the human adaptive or innate immune systems. In autoimmunity, the patient's immune system is activated against the body's own proteins. In inflammatory diseases (including in infection which can lead to inflammatory conditions), it is the overreaction of the immune system, and its subsequent downstream signaling (TNF, IFN, etc), which causes problems. Autoimmune diseases result from the propagation of T and B cells that recognize self antigens and mediate tissue destruction. Viral infections have long been suspected to instigate or overtly precipitate autoimmunity. In Lang et al. (J. Clin. Invest. 116:2456-2463, 2006) it has been demonstrated that viruses can initiate autoimmune damage through yet another mechanism.

It has been recently established that dsRNA are ligands for TLR3 (Alexoupoulou et al. (2001), Nature 413: 732-738), it has also been more recently shown that RNA released from either damaged tissue or tissues could also act as TLR3 ligands (Kariko et al, (2004) J. Biol. Chem.). Inappropriate activation of the TLRs by their endogenous RNA ligands within immune complexes almost certainly is an important factor contributing to pathogenesis of various inflammatory and autoimmune diseases. Recent papers suggest a role of TLR3 in inflammatory diseases (Cavassani et al. 2008), as TLR3 ligands amplify the hyperinflammatory response observed during sepsis, or autoimmunity diseases, such as rheumatoid arthritis (Bokarewa et al. (2008) Eur J. Immunol.), systemic lupus erythematosus (Rahman et al., (2006) Springer Sem. in Immunopathol.), and diabetes (Nature Med. 2005). It has also been reported that TLR3 may play a detrimental role in viral infections such as Western Reserve vaccinia virus, where TLR3 contributes to viral replication, detrimental lung inflammation and recruitment of leukocytes to the lung, resulting in increased morbidity or in West Nile Virus (WNV) where TLR3 allows the virus to cross the blood-brain barrier (BBB) and cause lethal encephalitis. The antibodies of the present invention that inhibit TLR3 under pH conditions corresponding to that of endosomes (e.g. as in myeloid DC) will be useful in the treatment and prevention of these conditions, including but not limited to the viral infections themselves and the conditions (e.g. autoimmune or inflammatory conditions) caused or enhanced by viral infection.

Zorde-Khvalevsky et al. (2009) Hepatology 49 report that hepatocyte proliferation was accelerated following partial hepatectomy in the absence of TLR3, while the levels of IL-6 and soluble interleukin-6 receptor (sIL-6R) were significantly lower, and further that after partial hepatectomy TLR3 signaling is induced in hepatocytes, resulting in activation of NF-kB, and that the presence of active TLR3 in Kupffer cells inhibits NF-kB activation. TLR3 signaling was therefore found to attenuate the initiation of liver regeneration; the anti-TLR3 antibodies of the invention can therefore be used in a method of inducing liver regeneration, in particular to treat and prevent diseases involving liver damage, e.g. cirrhosis, or diseases that are known to give rise to such liver damage such as alcoholism, hepatitis B or C infection or fatty liver diseases.

Kim et al. (2009) Immunol. Lett. report that TLR3 promotes osteoclastogenesis in the RA synovium both directly and indirectly by stimulating human monocytes directly to promote osteoclast differentiation and by inducing RANKL expression indirectly in RA-FLS. The expression of RANKL promotes the differentiation of osteoclasts in the RA synovium, and anti-RANKL antibodies (denosumab, Amgen Inc.) are efficacious in the treatment of osteoporosis. The anti-TLR3 antibodies of the invention can therefore be use to treat and prevent inflammatory bone destruction, e.g. osteoporosis, particularly in RA patients.

Wen et al. (2004) J. Immunol. 172: 3172-3180 suggest that autoimmune diseases can be induced by a viral-like stimulus, and identify TLR3 as capable of mediating such induction. Results demonstrate that polyIC together with insulin, but not insulin alone or other TLR ligands (CpG, LPS, PGN), can induce autoimmune diabetes and apoptosis of pancreatic islets in a mouse model. Furthermore, TLR3 showed the highest expression level in all individuals, compared to other TLRs. The anti-TLR3 antibodies of the invention can therefore be use to treat and prevent diabetes and islet autoimmunity.

The antibodies of the present invention that bind TLR3 under acidic conditions will generally bind both cell surface TLR3 and endosomic TLR3 at high affinity, such that the antibodies will be useful in any situation (e.g. treatment or prevention of disease) where targeting (e.g. modulating) TLR3 is useful. TLR3 has been found in some cases of inflammation the surface of macrophages and blocking TLR3 upon chloroquine neutralization of endosomal acification nevertheless exhibited some anti-inflammatory activity (Cavassani et al. 2008, supra). However, the antibodies of the invention will have the greatest advantage over other antibodies in the treatment or prevention of diseases where the modulating (e.g. inhibiting) the signaling by TLR3 in the cytosolic (e.g. endosomic) compartments is useful or required, and the relative importance of modulating signaling of such compartments TLR3 may depend on the disease. One example of such as disease is rheumatoid arthritis; endosomic compartment-expressed TLR3 is believed to play an important role in rheumatoid arthritis, since treatment with chloroquine, an inhibitor of endosomal acidification, inhibits TLR3 signaling and inhibits production of inflammatory cytokines from synovial cultures from patients having rheumatoid arthritis (Sacre et al. (2008) J. Immunol. 181:8002-8009). Endosomic compartment-expressed TLR3 is believed to play an important role in a number of other diseases where DC (e.g. myeloid DC) are involved in exacerbating disease, as mDC have a well documented capacity to take up antigens from apoptotic or necrotic cells including during tissue necrosis during acute inflammation.

Since the present antibodies are specific for TLR3, they can also be used for other purposes, including purifying TLR3 or TLR3-expressing cells, modulating (e.g. activating or inhibiting) TLR3 receptors in vitro, ex vivo, or in vivo, targeting TLR3-expressing cells for destruction in vivo, or specifically labeling/binding TLR3 in vivo, ex vivo, or in vitro, including for methods such as immunoblotting, IHC analysis, i.e. on frozen biopsies, FACS analysis, and immunoprecipitation.

DEFINITIONS

As used herein, "TLR3 ligands" refer to any compound that can specifically bind to and alter the activity of TLR3 in vitro, ex vivo, or in vivo. The compound can be a naturally occurring ligand, e.g., generally dsRNA or viral dsRNA, or a synthetic ligand such as polyIC or polyAU. The compound can be any type of molecule, including inorganic or organic compounds or elements, including proteins (such as antibodies), nucleic acids, carbohydrates, lipids, or any other molecular entity. Further, such compounds can modulate TLR3 receptors in any way, including activating or inhibiting, and by any mechanism, including by binding to the receptor and triggering or shutting off activity in a manner similar to a naturally occurring ligand, or by binding to the receptor and blocking access to other ligands. Preferably, the ligand activates the receptor, and as such can be used to induce the production of cytokines by TLR3-expressing cells.

The term "antibody," as used herein, refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms variable light chain ($V_L$) and variable heavy chain ($V_H$) refer to these light and heavy chains respectively. The heavy-chain constant domains that correspond to the different classes of immunoglobulins are termed "alpha," "delta," "epsilon," "gamma" and "mu," respectively. The subunit structures and three-dimensional configurations of different classes of immunoglobulins are well known. IgG and/or IgM are the preferred classes of antibodies employed in this invention, with IgG being particularly preferred, because they are the most common antibodies in the physiological situation and because they are most easily made in a laboratory setting. Preferably the antibody of this invention is a monoclonal antibody. Particularly preferred are humanized, chimeric, human, or otherwise-human-suitable antibodies. "Antibodies" also includes any fragment or derivative of any of the herein described antibodies.

The term "specifically binds to" means that an antibody can bind preferably in a competitive binding assay to the binding partner, e.g. TLR3, as assessed using either recombinant forms of the proteins, epitopes therein, or native proteins present on the surface of isolated target cells. Competitive binding assays and other methods for determining specific binding are further described below and are well known in the art.

When an antibody is said to "compete with" a particular monoclonal antibody (e.g. 31C3, 29H3, 23C8, 28F11 or 34A3), it means that the antibody competes with the monoclonal antibody in a binding assay using either recombinant TLR3 molecules or surface expressed TLR3 molecules. For example, if a test antibody reduces the binding of 31C3, 29H3, 23C8, 28F11 or 34A3 to a TLR3 polypeptide or TLR3-expressing cell in a binding assay, the antibody is said to "compete" respectively with 31C3, 29H3, 23C8, 28F11 or 34A3.

The term "affinity", as used herein, means the strength of the binding of an antibody to an epitope. The affinity of an antibody is given by the dissociation constant Kd, defined as $[Ab] \times [Ag]/[Ab-Ag]$, where $[Ab-Ag]$ is the molar concentration of the antibody-antigen complex, $[Ab]$ is the molar concentration of the unbound antibody and $[Ag]$ is the molar concentration of the unbound antigen. The affinity constant $K_a$ is defined by $1/Kd$. Preferred methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One preferred and standard method well known in the art for determining the affinity of mAbs is the use of Biacore instruments.

Within the context of this invention a "determinant" designates a site of interaction or binding on a polypeptide.

The term "epitope" is defined as an antigenic determinant, and is the area or region on an antigen to which an antibody binds. A protein epitope may comprise amino acid residues directly involved in the binding as well as amino acid residues which are effectively blocked by the specific antigen binding antibody or peptide, i.e., amino acid residues within the "footprint" of the antibody. It is the simplest form or smallest structural area on a complex antigen molecule that can combine with e.g., an antibody or a receptor. Epitopes can be linear or conformational/structural. The term "linear epitope" is defined as an epitope composed of amino acid residues that are contiguous on the linear sequence of amino acids (primary structure). The term "conformational or structural epitope" is defined as an epitope composed of amino acid residues that are not all contiguous and thus represent separated parts of the linear sequence of amino acids that are brought into proximity to one another by folding of the molecule (secondary, tertiary and/or quaternary structures). A conformational epitope is dependent on the 3-dimensional structure. The term 'conformational' is therefore often used interchangeably with 'structural'.

By "immunogenic fragment," it is herein meant any polypeptidic or peptidic fragment that is capable of eliciting an immune response such as (i) the generation of antibodies binding said fragment and/or binding any form of the molecule comprising said fragment, including the membrane-bound receptor and mutants derived therefrom, (ii) the stimulation of a T-cell response involving T-cells reacting to the bi-molecular complex comprising any MHC molecule and a peptide derived from said fragment, (iii) the binding of transfected vehicles such as bacteriophages or bacteria expressing genes encoding mammalian immunoglobulins. Alternatively, an immunogenic fragment also refers to any construction capable of eliciting an immune response as defined above, such as a peptidic fragment conjugated to a carrier protein by covalent coupling, a chimeric recombinant polypeptide construct comprising said peptidic fragment in its amino acid sequence, and specifically includes cells transfected with a cDNA of which sequence comprises a portion encoding said fragment.

"Toxic" or "cytotoxic" peptides or small molecules encompass any compound that can slow down, halt, or reverse the proliferation of cells, decrease their activity in any detectable way, or directly or indirectly kill them. Preferably, toxic or cytotoxic compounds work by directly killing the cells, by provoking apoptosis or otherwise. As used herein, a toxic "peptide" can include any peptide, polypeptide, or derivative of such, including peptide- or polypeptide-derivatives with unnatural amino acids or modified linkages. A toxic "small molecule" can includes any toxic compound or element, preferably with a size of less than 10 kD, 5 kD, 1 kD, 750 D, 600 D, 500 D, 400 D, 300 D, or smaller.

A "human-suitable" antibody refers to any antibody, derivatized antibody, or antibody fragment that can be safely used in humans for, e.g. the therapeutic methods described herein. Human-suitable antibodies include all types of humanized, chimeric, or fully human antibodies, or any antibodies in which at least a portion of the antibodies is derived from humans or otherwise modified so as to avoid the immune response that is generally provoked when native non-human antibodies are used.

For the purposes of the present invention, a "humanized" or "human" antibody refers to an antibody in which the constant and variable framework region of one or more human immunoglobulins is fused with the binding region, e.g. the CDR, of an animal immunoglobulin. Such antibodies are designed to maintain the binding specificity of the non-human antibody from which the binding regions are derived, but to avoid an immune reaction against the non-human antibody. Such antibodies can be obtained from transgenic mice or other animals that have been "engineered" to produce specific human antibodies in response to antigenic challenge (see, e.g., Green et al. (1994) Nature Genet 7:13; Lonberg et al. (1994) Nature 368:856; Taylor et al. (1994) Int Immun 6:579, the entire teachings of which are herein incorporated by reference). A fully human antibody also can be constructed by genetic or chromosomal transfection methods, as well as phage display technology, all of which are known in the art (see, e.g., McCafferty et al. (1990) Nature 348:552-553). Human antibodies may also be generated by in vitro activated B cells (see, e.g., U.S. Pat. Nos. 5,567,610 and 5,229,275, which are incorporated in their entirety by reference).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The terms "Fc domain," "Fc portion," and "Fc region" refer to a C-terminal fragment of an antibody heavy chain, e.g., from about amino acid (aa) 230 to about aa 450 of human γ (gamma) heavy chain or its counterpart sequence in other types of antibody heavy chains (e.g., α, δ, ε and μ for human antibodies), or a naturally occurring allotype thereof. Unless otherwise specified, the commonly accepted Kabat amino acid numbering for immunoglobulins is used throughout this disclosure (see Kabat et al. (1991) Sequences of Protein of Immunological Interest, 5th ed., United States Public Health Service, National Institute of Health, Bethesda, Md.).

The terms "isolated", "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

Within the context of this invention, the term antibody that "binds" a common determinant designates an antibody that binds said determinant with specificity and/or affinity.

Producing Anti-TLR3 Antibodies

The antibodies of this invention specifically bind TLR3. Antibodies of the invention furthermore bind TLR3 under acidic conditions corresponding to that encountered in an acidified endosomic compartment. Antibodies of the invention are furthermore capable of inhibiting the TLR3 signaling pathway. The ability of the inhibitory antibodies to specifically inhibit TLR3 signaling pathway makes them useful for numerous applications, in particular for treating or preventing diseases wherein the inhibition of TLR3 signaling pathway is desirable, i.e. avoid further cytokine and chemokine secretion as well as cellular activation, as described herein.

In one embodiment, the invention provides an antibody that binds human TLR3, and competes for binding to human TLR3 with monoclonal antibody 31C3, 29H3, 23C8, 28F11 or 34A3. Antibody 31C3 is produced by the cell deposited as 31C3.1 with the Collection Nationale de Culture de Microorganismes (CNCM), Institut Pasteur, 25 rue de Docteur Roux, F-75724 Paris on 3 Jul. 2009, under the number CNCM I-4186. Antibody 29H3 is produced by the cell deposited as 29H3.7 with the Collection Nationale de Culture de Microorganismes (CNCM), Institut Pasteur, 25 rue de Docteur Roux, F-75724 Paris on 3 Jul. 2009, under the number CNCM I-4187.

"TLR3", "TLR3 polypeptide" and "TLR3 receptor", used interchangeably, are used herein to refer to Toll-Like Receptor 3, a member of the Toll-like receptor (TLRs) family. The amino acid sequence of human TLR3 is shown in SEQ ID NO: 1 (NCBI accession number NP_003256, the disclosure of which is incorporated herein by reference). The human TLR3 mRNA sequence is described in NCBI accession number NM_003265. Human TLR3 sequences are also described in PCT patent publication no. WO 98/50547, the disclosure of which is incorporated herein by reference.

In one aspect, the invention provides an antibody that competes with monoclonal antibody 31C3, 29H3, 23C8, 28F11 or 34A3 and recognizes, binds to, or has immunospecificity for substantially or essentially the same, or the same, epitope or "epitopic site" on a TLR3 molecule as monoclonal antibody 31C3, 29H3, 23C8, 28F11 or 34A3. In other embodiments, the monoclonal antibody consists of, or is a derivative or fragment of, antibody 31C3, 29H3, 23C8, 28F11 or 34A3.

It will be appreciated that, while preferred antibodies bind to the same epitope as antibody 31C3, 29H3, 23C8, 28F11 or 34A3, the present antibodies can recognize and be raised against any part of the TLR3 polypeptide. For example, any fragment of TLR3, preferably but not exclusively human TLR3, or any combination of TLR3 fragments, can be used as immunogens to raise antibodies, and the antibodies of the invention can recognize epitopes at any location within the TLR3 polypeptide, so long as they can do so on TLR3 expressing cells such as MdDC or MoDC as described herein. In an embodiment, the recognized epitopes are present on the cell surface, i.e. they are accessible to antibodies present outside of the cell. Most preferably, the epitope is the epitope specifically recognized by antibody 31C3, 29H3, 23C8, 28F11 or 34A3. Further, antibodies recognizing distinct epitopes within TLR3 can be used in combination, e.g. to bind to TLR3 polypeptides with maximum efficacy and breadth among different individuals.

The antibodies of this invention may be produced by a variety of techniques known in the art. Typically, they are produced by immunization of a non-human animal, preferably a mouse, with an immunogen comprising a TLR3 polypeptide, preferably a human TLR3 polypeptide. The TLR3 polypeptide may comprise the full length sequence of a human TLR3 polypeptide, or a fragment or derivative thereof, typically an immunogenic fragment, i.e., a portion of the polypeptide comprising an epitope exposed on the surface of cells expressing a TLR3 polypeptide, preferably the epitope recognized by the 31C3, 29H3, 23C8, 28F11 or 34A3 antibody. Such fragments typically contain at least about 7 consecutive amino acids of the mature polypeptide sequence, even more preferably at least about 10 consecutive amino acids thereof. Fragments typically are essentially derived from the extra-cellular domain of the receptor. In a preferred embodiment, the immunogen comprises a wild-type human TLR3 polypeptide in a lipid membrane, typically at the surface of a cell. In a specific embodiment, the immunogen comprises intact cells, particularly intact human cells, optionally treated or lysed. In another preferred embodiment, the polypeptide is a recombinant TLR3 polypeptide.

The step of immunizing a non-human mammal with an antigen may be carried out in any manner well known in the art for stimulating the production of antibodies in a mouse (see, for example, E. Harlow and D. Lane, Antibodies: A Laboratory Manual., Cold Spring Harbor Laboratory Press, Cold Spring Harbor, N.Y. (1988), the entire disclosure of which is herein incorporated by reference). The immunogen is suspended or dissolved in a buffer, optionally with an adjuvant, such as complete or incomplete Freund's adjuvant. Methods for determining the amount of immunogen, types of buffers and amounts of adjuvant are well known to those of skill in the art and are not limiting in any way on the present invention. These parameters may be different for different immunogens, but are easily elucidated.

Similarly, the location and frequency of immunization sufficient to stimulate the production of antibodies is also well known in the art. In a typical immunization protocol, the non-human animals are injected intraperitoneally with antigen on day 1 and again about a week later. This is followed by recall injections of the antigen around day 20, optionally with an adjuvant such as incomplete Freund's adjuvant. The recall injections are performed intravenously and may be repeated for several consecutive days. This is followed by a booster injection at day 40, either intravenously or intraperitoneally, typically without adjuvant. This protocol results in the production of antigen-specific antibody-producing B cells after about 40 days. Other protocols may also be used as long as they result in the production of B cells expressing an antibody directed to the antigen used in immunization.

For polyclonal antibody preparation, serum is obtained from an immunized non-human animal and the antibodies present therein isolated by well-known techniques. The serum may be affinity purified using any of the immunogens set forth above linked to a solid support so as to obtain antibodies that react with TLR3 polypeptides.

In an alternate embodiment, lymphocytes from a non-immunized non-human mammal are isolated, grown in vitro, and then exposed to the immunogen in cell culture. The lymphocytes are then harvested and the fusion step described below is carried out.

For preferred monoclonal antibodies, the next step is the isolation of splenocytes from the immunized non-human mammal and the subsequent fusion of those splenocytes with an immortalized cell in order to form an antibody-producing hybridoma. The isolation of splenocytes from a non-human mammal is well-known in the art and typically involves removing the spleen from an anesthetized non-human mammal, cutting it into small pieces and squeezing the splenocytes from the splenic capsule through a nylon mesh of a cell strainer into an appropriate buffer so as to produce a single cell suspension. The cells are washed, centrifuged and resuspended in a buffer that lyses any red blood cells. The solution is again centrifuged and remaining lymphocytes in the pellet are finally resuspended in fresh buffer.

Once isolated and present in single cell suspension, the lymphocytes can be fused to an immortal cell line. This is typically a mouse myeloma cell line, although many other immortal cell lines useful for creating hybridomas are known in the art. Preferred murine myeloma lines include, but are not limited to, those derived from MOPC-21 and MPC-11 mouse tumors available from the Salk Institute Cell Distribution Center, San Diego, U.S.A., X63 Ag8653 and SP-2 cells available from the American Type Culture Collection, Rockville, Md. U.S.A. The fusion is effected using polyethylene glycol or the like. The resulting hybridomas are then grown in selective media that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Hybridomas are typically grown on a feeder layer of macrophages. The macrophages are preferably from littermates of the non-human mammal used to isolate splenocytes and are typically primed with incomplete Freund's adjuvant or the like several days before plating the hybridomas. Fusion methods are described in Goding, "Monoclonal Antibodies: Principles and Practice," pp. 59-103 (Academic Press, 1986), the disclosure of which is herein incorporated by reference.

The cells are allowed to grow in the selection media for sufficient time for colony formation and antibody production. This is usually between about 7 and about 14 days.

The hybridoma colonies are then assayed for the production of antibodies that specifically bind to TLR3 polypeptide gene products, optionally the epitope specifically recognized by antibody 31C3, 29H3, 23C8, 28F11 or 34A3. The assay is typically a colorimetric ELISA-type assay, although any assay may be employed that can be adapted to the wells that the hybridomas are grown in. Other assays include radioimmunoassays or fluorescence activated cell sorting. The wells positive for the desired antibody production are examined to determine if one or more distinct colonies are present. If more than one colony is present, the cells may be re-cloned and grown to ensure that only a single cell has given rise to the colony producing the desired antibody. Typically, the antibodies will also be tested for the ability to bind to TLR3 polypeptides, e.g., TLR3-expressing cells, in paraffin-embedded tissue sections, as described below.

Hybridomas that are confirmed to produce a monoclonal antibody of this invention can be grown up in larger amounts in an appropriate medium, such as DMEM or RPMI-1640. Alternatively, the hybridoma cells can be grown in vivo as ascites tumors in an animal.

After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Biosciences, publication No. 18-1037-46, Edition AC, the disclosure of which is hereby incorporated by reference). The bound antibody is typically eluted from protein A/protein G columns by using low pH buffers (glycine or acetate buffers of pH 3.0 or less) with immediate neutralization of antibody-containing fractions. These fractions are pooled, dialyzed, and concentrated as needed.

Positive wells with a single apparent colony are typically re-cloned and re-assayed to insure only one monoclonal antibody is being detected and produced.

Antibodies may also be produced by selection of combinatorial libraries of immunoglobulins, as disclosed for instance in (Ward et al. Nature, 341 (1989) p. 544, the entire disclosure of which is herein incorporated by reference).

The identification of one or more antibodies that bind(s) to TLR3, particularly substantially or essentially the same epitope as monoclonal antibody 31C3, 29H3, 23C8, 28F11 or 34A3, can be readily determined using any one of a variety of immunological screening assays in which antibody competition can be assessed. Many such assays are routinely practiced and are well known in the art (see, e.g., U.S. Pat. No. 5,660,827, issued Aug. 26, 1997, which is specifically incorporated herein by reference). It will be understood that actually determining the epitope to which an antibody described herein binds is not in any way required to identify an antibody that binds to the same or substantially the same epitope as the monoclonal antibody described herein.

For example, where the test antibodies to be examined are obtained from different source animals, or are even of a different Ig isotype, a simple competition assay may be employed in which the control (31C3, 29H3, 23C8, 28F11 or 34A3, for example) and test antibodies are admixed (or pre-adsorbed) and applied to a sample containing TLR3 polypeptides. Protocols based upon western blotting and the use of BIACORE analysis are suitable for use in such competition studies.

In certain embodiments, one pre-mixes the control antibodies (31C3, 29H3, 23C8, 28F11 or 34A3, for example) with varying amounts of the test antibodies (e.g., about 1:10 or about 1:100) for a period of time prior to applying to the TLR3 antigen sample. In other embodiments, the control and varying amounts of test antibodies can simply be admixed during exposure to the TLR3 antigen sample. As long as one can distinguish bound from free antibodies (e.g., by using separation or washing techniques to eliminate unbound antibodies) and 31C3, 29H3, 23C8, 28F11 or 34A3 from the test antibodies (e.g., by using species-specific or isotype-specific secondary antibodies or by specifically labeling 31C3, 29H3, 23C8, 28F11 or 34A3 with a detectable label) one can determine if the test antibodies reduce the binding of 31C3, 29H3, 23C8, 28F11 or 34A3 to the antigens, indicating that the test antibody recognizes substantially the same epitope as 31C3, 29H3, 23C8, 28F11 or 34A3. The binding of the (labeled) control antibodies in the absence of a completely irrelevant antibody can serve as the control high value. The control low value can be obtained by incubating the labeled (31C3, 29H3, 23C8, 28F11 or 34A3) antibodies with unlabelled antibodies of exactly the same type (31C3, 29H3, 23C8, 28F11 or 34A3), where competition would occur and reduce binding of the labeled antibodies. In a test assay, a significant reduction in labeled antibody reactivity in the presence of a test antibody is indicative of a test antibody that recognizes substantially the same epitope, i.e., one that "cross-reacts" or competes with the labeled (31C3, 29H3, 23C8, 28F11 or 34A3) antibody. Any test antibody that reduces the binding of 31C3, 29H3, 23C8, 28F11 or 34A3 to TLR3 antigens by at least about 50%, such as at least about 60%, or more preferably at least about 80% or 90% (e.g., about 65-100%), at any ratio of 31C3, 29H3, 23C8, 28F11 or 34A3:test antibody between about 1:10 and about 1:100 is considered to be an antibody that binds to substantially the same epitope or determinant as 31C3, 29H3, 23C8, 28F11 or 34A3. Preferably, such test antibody will reduce the binding of 31C3, 29H3, 23C8, 28F11 or 34A3 to the TLR3 antigen by at least about 90% (e.g., about 95%).

Competition can also be assessed by, for example, a flow cytometry test. In such a test, cells bearing a given TLR3 polypeptide can be incubated first with 31C3, 29H3, 23C8, 28F11 or 34A3, for example, and then with the test antibody labeled with a fluorochrome or biotin. The antibody is said to compete with 31C3, 29H3, 23C8, 28F11 or 34A3 if the binding obtained upon preincubation with a saturating amount of 31C3, 29H3, 23C8, 28F11 or 34A3 is about 80%, preferably about 50%, about 40% or less (e.g., about 30%, 20% or 10%) of the binding (as measured by mean of fluorescence) obtained by the antibody without preincubation with 31C3, 29H3, 23C8, 28F11 or 34A3. Alternatively, an antibody is said to compete with 31C3, 29H3, 23C8, 28F11 or 34A3 if the binding obtained with a labeled 31C3, 29H3, 23C8, 28F11 or 34A3 antibody (by a fluorochrome or biotin) on cells preincubated with a saturating amount of test antibody is about 80%, preferably about 50%, about 40%, or less (e.g., about 30%, 20% or 10%) of the binding obtained without preincubation with the test antibody.

A simple competition assay in which a test antibody is pre-adsorbed and applied at saturating concentration to a surface onto which a TLR3 antigen is immobilized may also be employed. The surface in the simple competition assay is preferably a BIACORE chip (or other media suitable for surface plasmon resonance analysis). The control antibody (e.g., 31C3, 29H3, 23C8, 28F11 or 34A3) is then brought into contact with the surface at a TLR3-saturating concentration and the TLR3 and surface binding of the control antibody is measured. This binding of the control antibody is compared with the binding of the control antibody to the TLR3-containing surface in the absence of test antibody. In a test assay, a significant reduction in binding of the TLR3-containing surface by the control antibody in the presence of a test antibody indicates that the test antibody recognizes substantially the same epitope as the control antibody such that the test antibody "cross-reacts" with the control antibody. Any test antibody that reduces the binding of control (such as 31C3, 29H3, 23C8, 28F11 or 34A3) antibody to a TLR3 antigen by at least about 30% or more, preferably about 40%, can be considered to be an antibody that binds to substantially the same epitope or determinant as a control (e.g., 31C3, 29H3, 23C8, 28F11 or 34A3). Preferably, such a test antibody will reduce the binding of the control antibody (e.g., 31C3, 29H3, 23C8, 28F11 or 34A3) to the TLR3 antigen by at least about 50% (e.g., at least about 60%, at least about 70%, or more). It will be appreciated that the order of control and test antibodies can be reversed: that is, the control antibody can be first bound to the surface and the test antibody is brought into contact with the surface thereafter in a competition assay. Preferably, the antibody having higher affinity for the TLR3 antigen is bound to the surface first, as it will be expected that the decrease in binding seen for the second antibody (assuming the antibodies are cross-reacting) will be of greater magnitude. Further examples of such assays are provided in, e.g., Saunal (1995) J. Immunol. Methods 183: 33-41, the disclosure of which is incorporated herein by reference.

Determination of whether an antibody binds within an epitope region can be carried out in ways known to the person skilled in the art. As one example of such mapping/characterization methods, an epitope region for an anti-TLR3 antibody may be determined by epitope "foot-printing" using chemical modification of the exposed amines/carboxyls in the TLR3 protein. One specific example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry. See, e.g., Ehring H, Analytical Biochemistry, Vol. 267 (2) pp. 252-259 (1999) Engen, J. R. and Smith, D. L. (2001) Anal. Chem. 73, 256A-265A. Another example of a suitable epitope identification technique is nuclear magnetic resonance epitope mapping (NMR), where typically the position of the signals in two-dimensional NMR spectra of the free antigen and the antigen complexed with the antigen binding peptide, such as an antibody, are compared. The antigen typically is selectively isotopically labeled with 15N so that only signals corresponding to the antigen and no signals from the antigen binding peptide are seen in the NMR-spectrum. Antigen signals originating from amino acids involved in the interaction with the antigen binding peptide typically will shift position in the spectrum of the complex compared to the spectrum of the free antigen, and the amino acids involved in the binding can be identified that way. See, e.g., Ernst Schering Res Found Workshop. 2004; (44): 149-67; Huang et Journal of Molecular Biology, Vol. 281 (1) pp. 61-67 (1998); and Saito and Patterson, Methods. 1996 June; 9 (3): 516-24.

Epitope mapping/characterization also can be performed using mass spectrometry methods. See, e.g., Downward, J Mass Spectrom. 2000 April; 35 (4): 493-503 and Kiselar and Downward, Anal Chem. 1999 May 1; 71 (9): 1792-801. Protease digestion techniques also can be useful in the context of epitope mapping and identification. Antigenic determinant-relevant regions/sequences can be determined by protease digestion, e.g. by using trypsin in a ratio of about 1:50 to TLR3 or o/n digestion at and pH 7-8, followed by mass spectrometry (MS) analysis for peptide identification. The peptides protected from trypsin cleavage by the anti-TLR3 binder can subsequently be identified by comparison of samples subjected to trypsin digestion and samples incubated with antibody and then subjected to digestion by e.g. trypsin (thereby revealing a footprint for the binder). Other enzymes like chymotrypsin, pepsin, etc., also or alternatively can be used in similar epitope characterization methods. Moreover, enzymatic digestion can provide a quick method for analyzing whether a potential antigenic determinant sequence is within a region of the TLR3 polypeptide that is not surface exposed and, accordingly, most likely not relevant in terms of immunogenicity/antigenicity. See, e.g., Manca, Ann Ist Super Sanita. 1991; 27: 15-9 for a discussion of similar techniques.

Site-directed mutagenesis is another technique useful for elucidation of a binding epitope. For example, in "alanine-scanning", each residue within a protein segment is re-placed with an alanine residue, and the consequences for binding affinity measured. If the mutation leads to a significant resuction in binding affinity, it is most likely involved in binding. Monoclonal antibodies specific for structural epitopes (i.e., antibodies which do not bind the unfolded protein) can be used to verify that the alanine-replacement does not influence over-all fold of the protein. See, e.g., Clackson and Wells, Science 1995; 267:383-386; and Wells, Proc Natl Acad Sci USA 1996; 93:1-6.

Electron microscopy can also be used for epitope "foot-printing". For example, Wang et al., Nature 1992; 355:275-278 used coordinated application of cryoelectron microscopy, three-dimensional image reconstruction, and X-ray crystallography to determine the physical footprint of a Fab-fragment on the capsid surface of native cowpea mosaic virus.

Other forms of "label-free" assay for epitope evaluation include surface plasmon resonance (SPR, BIACORE) and reflectometric interference spectroscopy (RifS). See, e.g., Fagerstam et al., Journal Of Molecular Recognition 1990; 3:208-14; Nice et al., J. Chroma-togr. 1993; 646:159-168; Leipert et al., Angew. Chem. Int. Ed. 1998; 37:3308-3311; Kroger et al., Biosensors and Bioelectronics 2002; 17:937-944.

It should also be noted that an antibody binding the same or substantially the same epitope as an antibody of the invention can be identified in one or more of the exemplary competition assays described herein.

Once antibodies are identified that are capable of binding TLR3 and/or having other desired properties, they will also typically be assessed, using standard methods including those described herein, for their ability to bind to other polypeptides, including unrelated polypeptides and other TLR family members (e.g., human TLR1, 2, or 4-10). Ideally, the antibodies only bind with substantial affinity to TLR3, e.g., human TLR3, and do not bind at a significant level to unrelated polypeptides or to other TLR family members (e.g., TLR2 or TLR4; the amino acid sequence of human precursor TLR4 including a signal peptide at amino acid residues 1-23 is found in NCBI accession number NP_612564, the disclosure of which is incorporated herein by reference). However, it will be appreciated that, as long as the affinity for TLR3 is substantially greater (e.g., 5×, 10×, 50×, 100×, 500×, 1000×, 10,000×, or more) than it is for other TLR family members (or other, unrelated polypeptides), then the antibodies are suitable for use in the present methods.

The binding of the antibodies to TLR3-expressing cells can also be assessed in non-human primates, e.g. cynomolgus monkeys, or other mammals such as mice. The invention therefore provides an antibody, as well as fragments and derivatives thereof, wherein said antibody, fragment or derivative specifically bind TLR3, and which furthermore bind TLR3 from non-human primates, e.g., cynomolgus monkeys. Optionally, cellular uptake or localization, optionally localization in a subcellular compartment such as the endocytic pathway, is assessed in order to select an antibody that is readily taken up into the cell and/or into the cellular compartment where it TLR3 is expressed. Cellular uptake or localization will generally be measured in the cells in which the antibody is sought or believed to exert its activity, such as in DC. Cellular uptake or localization can be assessed by standard methods, such as by confocal staining using an antibody marked with a detectable moiety (e.g. a fluorescent moiety).

Upon immunization and production of antibodies in a vertebrate or cell, particular selection steps may be performed to isolate antibodies as claimed. In this regard, in a specific embodiment, the invention also relates to methods of producing such antibodies, comprising: (a) immunizing a non-human mammal with an immunogen comprising a TLR3 polypeptide; and (b) preparing antibodies from said immunized animal; and (c) selecting antibodies from step (b) that are capable of binding TLR3. The antibodies can be tested for binding to TLR3 under acidic conditions corresponding to those in cytosolic compartments (e.g. the endosomic compartments), such as at a pH of between about 5.5 to 6.5.

The antibodies' bivalent binding affinity for human TLR3 under acidic conditions can determined. Antibodies can be characterized for example by a mean $K_D$ of no more than about (i.e. better affinity than) 100, 60, 10, 5, or 1 nanomolar, preferably sub-nanomolar or optionally no more than about 300, 200, 100 or 10 picomolar. $K_D$ can be determined for example for example by immobilizing recombinantly produced human TLR3 proteins on a chip surface, followed by application of the antibody to be tested in solution, e.g. as shown in the present Examples. To select antibodies that retain binding similar binding under acidic and neutral conditions, one can seek to minimize the difference observed between binding at neutral pH (e.g. 7.2) and acidic pH (e.g. a pH in the range of 4.5-6-5), for example where binding affinity at acidic pH is not substantially lower, e.g. where the $K_D$ for binding to TLR3 decreases by no more than 0.2-, 0.3-, 0.5-, 1.0-, or 1.5-$\log_{10}$, than that observed at non-acid pH. In one embodiment, the method further comprises a step (d), selecting antibodies from (b) that are capable of competing for binding to TLR3 with antibody 31C3, 29H3, 23C8, 28F11 or 34A3.

In one aspect of any of the embodiments, the antibodies prepared according to the present methods are monoclonal antibodies. In another aspect, the non-human animal used to produce antibodies according to the methods of the invention is a mammal, such as a rodent, bovine, porcine, fowl, horse, rabbit, goat, or sheep. The antibodies of the present invention encompass 31C3, 29H3, 23C8, 28F11 or 34A3. However, it will be appreciated that other antibodies can be obtained using the methods described herein, and thus antibodies of the invention can be antibodies other than 31C3, 29H3, 23C8, 28F11 or 34A3. Additionally, antibodies of the invention can optionally be specified to be antibodies other than any of antibodies TLR3.7 (eBioScience Inc., San Diego), antibody C1068 of WO 06/060513, antibody C1130 of WO 2007/051164, any of the antibodies disclosed WO2010/051470, e.g., antibodies 1-19 and F17-F19, antibody 40C1285 (Abcam), or antibodies 619F7, 713E4, 716G10, IMG-5631, IMG-315 or IMG-5348 (all from Imgenex. Corp.) or derivatives of the foregoing, e.g. that comprise the antigen binding region in whole or in part.

According to an alternate embodiment, the DNA encoding an antibody that binds an epitope present on TLR3 polypeptides is isolated from the hybridoma of this invention and placed in an appropriate expression vector for transfection into an appropriate host. The host is then used for the recombinant production of the antibody, or variants thereof, such as a humanized version of that monoclonal antibody, active fragments of the antibody, chimeric antibodies comprising the antigen recognition portion of the antibody, or versions comprising a detectable moiety.

DNA encoding the monoclonal antibodies of the invention, e.g., antibody 31C3, 29H3, 23C8, 28F11 or 34A3, can be readily isolated and sequenced using conventional procedures (e.g., by using oligonucleotide probes that are capable of binding specifically to genes encoding the heavy and light chains of murine antibodies). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. As described elsewhere in the present specification, such DNA sequences can be modified for any of a large number of purposes, e.g., for humanizing antibodies, producing fragments or derivatives, or for modifying the sequence of the antibody, e.g., in the antigen binding site in order to optimize the binding specificity of the antibody.

Recombinant expression in bacteria of DNA encoding the antibody is well known in the art (see, for example, Skerra et al., Curr. Opinion in Immunol., 5, pp. 256 (1993); and Pluckthun, Immunol. 130, p. 151 (1992).

Assessing the Ability of Antibodies to Modulate TLR3 Signaling

In certain embodiments, the antibodies of this invention are able to modulate, e.g., inhibit signaling by, TLR3 polypeptides, and consequently to modulate the activity or behavior of TLR3-expressing cells. For example, antibodies may inhibit the activation of TLR3-expressing cells, e.g. they can inhibit the TLR3 signaling pathway, optionally without blocking the binding to TLR3 of natural or endogenous ligands such as dsRNA; optionally they may block the ability of TLR3 protein to form homodimers in the presence of a TLR3 ligand, thus blocking the initiation a signaling cascade. These antibodies are thus referred to as "neutralizing" or "inhibitory" or "blocking" antibodies. Such antibodies are useful, inter alia, for decreasing the activity of TLR3-expressing immune cells, e.g. for the treatment or prevention of conditions involving excess TLR3-expressing cell activity or number, or where decreased TLR3-expressing cell activity can ameliorate, prevent, eliminate, or in any way improve the condition or any symptom thereof.

A range of cellular assays can be used to assess the ability of the antibodies to modulate TLR3 signaling. Any of a large number of assays, including molecular, cell-based, and animal-based models can be used to assess the ability of anti-TLR3 antibodies to modulate TLR3-expressing cell activity. For example, cell-based assays can be used in which cells expressing TLR3 are exposed to dsRNA, viral dsRNA, polyIC, or poly AU, or another TLR3 ligand and the ability of the antibody to disrupt the binding of the ligand or the stimulation of the receptor (as determined, e.g., by examining any of the TLR3 cell activities addressed herein, such as interferon expression, NFkB activity, NK cell activation, etc.) is assessed. The TLR3 ligand used in the assays may be in any suitable form, including but not limited to as a purified ligand composition, in a mixture with non-TLR3 ligands, in a naturally occurring composition, in a cell or on the surface of a cell, or secreted by a cell (e.g. a cell that produces ligand is used in the assay), in solution or on a solid support.

The activity of TLR3-expressing cells can also be assessed in the absence of a ligand, by exposing the cells to the antibody itself and assessing its effect on any aspect of the cells' activity or behavior. In such assays, a baseline level of activity (e.g., cytokine production, proliferation, see below) of the TLR3-expressing cells is obtained in the absence of a ligand, and the ability of the antibody or compound to alter the baseline activity level is detected. In one such embodiment, a high-throughput screening approach is used to identify compounds capable of affecting the activation of the receptor.

Any suitable physiological change that reflects TLR3 activity can be used to evaluate test antibodies or antibody derivatives. For example, one can measure a variety of effects, such as changes in gene expression (e.g., NFkB-responding genes), protein secretion (e.g., interferon), cell growth, cell proliferation, pH, intracellular second messengers, e.g., $Ca^{2+}$, IP3, cGMP, or cAMP, or activity such as ability to activate NK cells. In one embodiment, the activity of the receptor is assessed by detecting production of cytokines, e.g. TLR3-responsive cytokines, proinflammatory cytokines.

TLR3 modulation can be assessed using any of a number of possible readout systems, most based upon a TLR/IL-1R signal transduction pathway, involving, e.g., the MyD88-independent/TRIF dependent signal transduction pathway, involving, e.g., IRF3, IRF7, IKKε and/or TBK1 (Akira and Takeda (2004) Nature Review Immunol. 4:499-511). These pathways activate kinases including KB kinase complex. TLR3 activation can be assessed by examining any aspect of TLR signaling. For example, activation of TLR signaling triggers alterations in protein-protein associations (e.g., TRIF with TBK and/or IKKε), in intracellular localization of proteins (such as movement of NK-kB into the nucleus), and in gene expression (e.g., in expression of NK-kB sensitive genes), and cytokine production (e.g., production and secretion of IFN-gamma, IL-6, IP10, MCP-1). Any such alteration can be detected and used to detect TLR3 activation. In one embodiment, TLR3 stimulation is detected by collecting supernatants after 18-20 hr of culture and measuring levels of IFN-gamma, IL-6, IP-10 and/or MCP-1 by sandwich ELISA. In another embodiment, TLR3 stimulation is detected by collecting supernatants after 18-20 hr of culture and measuring levels of IFN-gamma, IL-6, IP-10 and/or MCP-1 by sandwich ELISA.

In one embodiment, cells that naturally express TLR3 are used, such as DC (e.g. myeloid DC or monocyte derived DC. In another embodiment, cells are used that contain a reporter construct that causes the expression of a detectable gene product upon TLR3 stimulation and consequent activation of the signal transduction pathway. Reporter genes and reporter gene constructs particularly useful for the assays include, e.g., a reporter gene operatively linked to a promoter sensitive to NF-kB or to signaling mediated by, particularly TRIF, IRF3, IRF7, IKKε, TBK1. Examples of such promoters include, without limitation, those for IL-1alpha, IL-6, IL-8, IL-12 p40, IP-10, CD80, CD86, and TNF-alpha. The reporter gene operatively linked to the TLR-sensitive promoter can include, without limitation, an enzyme (e.g., luciferase, alkaline phosphatase, beta-galactosidase, chloramphenicol acetyltransferase (CAT), etc.), a bioluminescence marker (e.g., green-fluorescent protein (GFP, e.g., U.S. Pat. No. 5,491,084), blue fluorescent protein (BFP, e.g., U.S. Pat. No. 6,486,382), etc.), a surface-expressed molecule (e.g., CD25, CD80, CD86), and a secreted molecule (e.g., IL-1, IL-6, IL-8, IL-12 p40, TNF-alpha). See, e.g., Hcker H et al. (1999) EMBO J. 18:6973-82; Murphy T L et al. (1995) Mol Cell Biol 15:5258-67, the disclosures of which are herein incorporated by reference. Reporter plasmids suitable for use are commercially available (InvivoGen, San Diego, Calif.). In one embodiment, the assay includes determining, in a host cell made to express a human TLR3 polypeptide, whether a test composition induces luciferase expression (or other reporter) under the control of a promoter responsive to TLR3 signaling (e.g. ISRE, IFN-stimulated response element).

In assays relying on enzyme activity readout, substrate can be supplied as part of the assay, and detection can involve measurement of chemoluminescence, fluorescence, color development, incorporation of radioactive label, drug resistance, optical density, or other marker of enzyme activity. For assays relying on surface expression of a molecule, detection can be accomplished using flow cytometry (FACS) analysis or functional assays. Secreted molecules can be assayed using enzyme-linked immunosorbent assay (ELISA) or bioassays. Many of these and other suitable readout systems are well known in the art and are commercially available. Preferably, the reporter system, whichever used, is quantifiable.

In another embodiment, the effect of the antibodies on TLR3-expressing cells is assessed in non-human primates in vivo. For example, a pharmaceutical composition comprising an anti-TLR3 antibody of the present invention is administered to a non-human primate that is either healthy or affected by a condition, e.g. an autoimmune disease or inflammation and the effect of the administration on, e.g., the number or activity of TLR3-expressing cells in the primate, the presence and/or levels of cytokines, or on the progression of the condition is assessed. Any antibody or antibody derivative or fragment that effects a detectable change in any of these TLR3-related parameters is a candidate for use in the herein-described methods.

In any of the herein-described assays, an increase or decrease of 5%, 10%, 20%, preferably 30%, 40%, 50%, most preferably 60%, 70%, 80%, 90%, 95%, or greater in any detectable measure of TLR3-stimulated activity in the cells indicates that the test antibody is suitable for use in the present methods.

When assessing inhibitory anti-TLR3 antibodies, the antibodies can be advantageously selected to modify any parameter associated with inflammation or autoimmunity. For example, antibodies can be selected to reduce activation, particularly production of pro-inflammatory cytokines, in cells. The cells may be, for example, cells obtained from an individual suffering from an inflammatory or autoimmune disorder.

Antibody CDR Sequences

In one aspect of any of the embodiments of the invention, an antibody may comprise a heavy and/or light chain having CDR1, 2 and/or 3 sequences according to the respective formula selected from Formulas (I) to (XX). In any embodiment herein, a particular HCDR1-3 or LCDR-1-3 may be specified as having a sequence of Formulas (I) to (XX). In one preferred embodiment, the antibody comprises a light chain comprising the three LCDRs and a heavy chain comprising the three HCDRs. Optionally, provided is an antibody where any of the light and/or heavy chain variable regions are fused to an immunoglobulin constant region of the IgG type, optionally a human constant region, optionally an IgG1 or IgG4 isotype.

In one embodiment, LCDR1 is of Formula (I):

(SEQ ID NO: 61)
(I) R-A-S-E-N-I-Y-S-Xaa$_1$-L-A, wherein Xaa$_1$ may be a conservative or non conservative substitution or a deletion or insertion, preferably, wherein Xaa$_1$ may be Ser, Tyr or Asn.

In one embodiment, LCDR2 is of Formula (II):

(SEQ ID NO: 62)
(II) Xaa$_2$-A-K-T-L-A-E, wherein Xaa$_2$ may be a conservative or non conservative substitution or a deletion or insertion, preferably, wherein Xaa$_2$ may be Asn or Tyr.

In one embodiment, LCDR3 is of Formula (III):

(SEQ ID NO: 63)
(III) Q-H-H-Y-G-T-P-Xaa$_3$-T, wherein Xaa$_3$ may be a conservative or non conservative substitution or a deletion or insertion, preferably, wherein Xaa$_3$ may be Tyr, Phe, Pro.

In one embodiment, LCDR1 is of Formula (IV):

(SEQ ID NO: 64)
(IV)   Xaa$_4$-A-S-Xaa$_5$-Xaa$_6$-Xaa$_7$-Xaa$_8$-Xaa$_9$-Xaa$_{10}$-Xaa$_{11}$-Xaa$_{12}$, wherein Xaa$_4$ to Xaa$_{12}$ may be a conservative or non conservative substitution or a deletion or insertion, preferably, wherein Xaa$_4$ may be Arg, Ser or Lys, and/or Xaa$_5$ may be Glu, Ser or Gln, and/or Xaa$_6$ may be Asn or Ser, and/or Xaa$_7$ may be Ile or Val, and/or Xaa$_8$ may be a deletion, Tyr or Arg, and/or Xaa$_9$ may be Ser or Thr, and/or Xaa$_{10}$ may be Tyr, Asn or Ser, and/or Xaa$_{11}$ may be Leu, Met or Val, and/or Xaa$_{12}$ may be Ala or Phe.

In one embodiment, LCDR1 is of Formula (V):

(SEQ ID NO: 65)
(V) Xaa$_{13}$-Xaa$_{14}$-Xaa$_{15}$-Xaa$_{16}$-L-A-Xaa$_{17}$ wherein Xaa$_{13}$ to Xaa$_{17}$ may be a conservative or non conservative substitution or a deletion or insertion, preferably, wherein Xaa$_{13}$ may be Leu, Asn or Tyr, and/or Xaa$_{14}$ may be Ala or Thr, and/or Xaa$_{15}$ may be Lys or Ser, and/or Xaa$_{16}$ may be Asn or Thr, and/or Xaa$_{17}$ may be Glu or Ser.

In one embodiment, LCDR2 is of Formula (VI):

(SEQ ID NO: 66)
(VI)    Xaa$_{18}$-A-Xaa$_{19}$-Xaa$_{20}$-Xaa$_{21}$-Xaa$_{22}$-Xaa$_{23}$ wherein Xaa$_{19}$ to Xaa$_{23}$ may be a conservative or non conservative substitution or a deletion or insertion, preferably, wherein Xaa$_{18}$ may be Tyr, Asn or Leu, and/or Xaa$_{19}$ may be Ser or Lys, and/or Xaa$_{20}$ may be Asn or Thr, and/or Xaa$_{21}$ may be Leu or Arg, and/or Xaa$_{22}$ may be Ala or His, and/or Xaa$_{23}$ may be Thr or Glu.

In one embodiment, LCDR2 is of Formula (VII):

(SEQ ID NO: 67)
(VII) L-Xaa$_{24}$-S-N-Xaa$_{25}$-Xaa$_{26}$-Xaa$_{27}$ wherein Xaa$_{24}$ to Xaa$_{27}$ may be a conservative or non conservative substitution or a deletion or insertion, preferably, wherein Xaa$_{24}$ may be Thr or Ala, and/or Xaa$_{25}$ may be Leu or Arg, and/or Xaa$_{26}$ may be Ala or His, and/or Xaa$_{27}$ may be Ser or Thr.

In one embodiment, LCDR3 is of Formula (VIII):

(SEQ ID NO: 68)
(VIII)    Q-Xaa$_{28}$-Xaa$_{29}$-Xaa$_{30}$-G-Xaa$_{31}$-P-Xaa$_{32}$-T wherein Xaa$_{28}$ to Xaa$_{32}$ may be a conservative or non conservative substitution or a deletion or insertion, preferably, wherein Xaa$_{28}$ may be His or Gln, and/or Xaa$_{29}$ may be His or Trp, and/or Xaa$_{30}$ may be Tyr or Thr, and/or Xaa$_{31}$ may be Thr or Asn, and/or Xaa$_{32}$ may be Tyr, Phe or Pro.

In one embodiment, LCDR3 is of Formula (IX):

(SEQ ID NO: 69)
(IX)    Xaa$_{33}$-Xaa$_{34}$-H-Xaa$_{35}$-Xaa$_{36}$-Xaa$_{37}$-P-Xaa$_{38}$-T wherein Xaa$_{33}$ to Xaa$_{38}$ may be a conservative or non conservative substitution or a deletion or insertion, preferably, wherein Xaa$_{33}$ may be Gln or Leu, and/or Xaa$_{34}$ may be His or Gln, and/or Xaa$_{35}$ may be Trp or Tyr, and/or Xaa$_{36}$ may be Asn or Gly, and/or Xaa$_{37}$ may be Tyr or Thr, and/or Xaa$_{38}$ may be Tyr, Phe or Pro.

In one embodiment, LCDR3 is of Formula (X):

(SEQ ID NO: 70)
(X)    Xaa$_{39}$-Q-Xaa$_{40}$-Xaa$_{41}$-Xaa$_{42}$-Xaa$_{43}$-P-Xaa$_{44}$-T wherein Xaa$_{40}$ to Xaa$_{44}$ may be a conservative or non conservative substitution or a deletion or insertion, preferably, wherein Xaa$_{39}$ may be Gln or Leu, and/or Xaa$_{40}$ may be Trp or His, and/or Xaa$_{41}$ may be Thr or Trp, and/or Xaa$_{42}$ may be Gly or Asn, and/or Xaa$_{43}$ may be Asn or Tyr, and/or Xaa$_{44}$ may be Pro or Tyr.

In one embodiment, HCDR1 is of Formula (XI):

(SEQ ID NO: 71)
(XI) G-Y-S-F-T-G-Y-Xaa$_{45}$-Xaa$_{46}$-H wherein Xaa$_{45}$ to Xaa$_{46}$ may be a conservative or non conservative substitution or a deletion or insertion, preferably, wherein Xaa$_{45}$ may be Phe or Tyr, and/or Xaa$_{46}$ may be Met or Ile.

In one embodiment, HCDR1 is of Formula (XII):

(SEQ ID NO: 72)
(XII)    G-Y-S-F-T-Xaa$_{47}$-Y-Xaa$_{48}$-M-H wherein Xaa$_{47}$ to Xaa$_{48}$ may be a conservative or non conservative substitution or a deletion or insertion, preferably, wherein Xaa$_{47}$ may be Gly or Ala, and/or Xaa$_{48}$ may be Phe or Tyr.

In one embodiment, HCDR1 is of Formula (XIII):

(SEQ ID NO: 73)
(XIII)    G-Y-S-F-T-Xaa$_{49}$-Y-Y-Xaa$_{50}$-H wherein Xaa$_{49}$ to Xaa$_{50}$ may be a conservative or non conservative substitution or a deletion or insertion, preferably, wherein Xaa$_{49}$ may be Gly or Ala, and/or Xaa$_{50}$ may be Ile or Met.

In one embodiment, HCDR1 is of Formula (XIV):

(XIV) G-Y-Xaa$_{51}$-F-T-Xaa$_{52}$-Y-Xaa$_{53}$-Xaa$_{54}$-Xaa$_{55}$ (SEQ ID NO: 74)

wherein Xaa$_{51}$ to Xaa$_{55}$ may be a conservative or non conservative substitution or a deletion or insertion, preferably, wherein Xaa$_{51}$ may be Val or Ser, and/or Xaa$_{52}$ may be Thr, Gly or Ala, and/or Xaa$_{53}$ may be Ser, Tyr or Phe, and/or Xaa$_{54}$ may be Ile or Met, and/or Xaa$_{55}$ may be Tyr or His.

In one embodiment, HCDR1 is of Formula (XV):

(XV) G-Y-S-Xaa$_{56}$-T-Xaa$_{57}$-G-Y-Xaa$_{58}$-Xaa$_{59}$-H (SEQ ID NO: 75)

wherein Xaa$_{56}$ to Xaa$_{59}$ may be a conservative or non conservative substitution or a deletion or insertion, preferably, wherein Xaa$_{56}$ may be Ile or Phe, and/or Xaa$_{57}$ may be a deletion or Ser, and/or Xaa$_{58}$ may be Ser, Tyr or Phe, and/or Xaa$_{59}$ may be Trp, Ile or Met.

In one embodiment, HCDR1 is of Formula (XVI):

(XVI) G-Y-Xaa$_{60}$-Xaa$_{61}$-T-Xaa$_{62}$-Xaa$_{63}$-Y-S-Xaa$_{64}$-Xaa$_{65}$ (SEQ ID NO: 76)

wherein Xaa$_{60}$ to Xaa$_{65}$ may be a conservative or non conservative substitution or a deletion or insertion, preferably, wherein Xaa$_{60}$ may be Val or Ser and/or Xaa$_{61}$ may be Phe or Ile and/or Xaa$_{62}$ may be Thr or Ser and/or Xaa$_{63}$ may be deletion or Gly and/or Xaa$_{64}$ may be Ile or Trp and/or Xaa$_{65}$ may be Tyr or His.

In one embodiment, HCDR2 is of Formula (XVII):

(XVII) R-I-N-P-Y-Xaa$_{66}$-G-A-T-S-Xaa$_{67}$-N-Xaa$_{68}$-N-F-K-D (SEQ ID NO: 77)

wherein Xaa$_{66}$ to Xaa$_{68}$ may be a conservative or non conservative substitution or a deletion or insertion, preferably, wherein Xaa$_{66}$ may be Asn or Tyr and/or Xaa$_{67}$ may be deletion or Tyr and/or Xaa$_{68}$ may be Arg or Gln.

In one embodiment, HCDR2 is of Formula (XVIII):

(XVIII) R-I-N-P-Y-Xaa$_{66}$-G-A-T-S-Y-N-Q-N-F-K-D (SEQ ID NO: 78)

wherein Xaa$_{66}$ may be a conservative or non conservative substitution or a deletion or insertion, preferably, wherein Xaa$_{66}$ may be Asn or Tyr In one embodiment, HCDR2 is of Formula (XIX):

(XIX) R-I-N-P-Y-N-G-A-T-S-Y-N-Xaa$_{68}$-N-F-K-D (SEQ ID NO: 79)

wherein Xaa$_{68}$ may be a conservative or non conservative substitution or a deletion or insertion, preferably, wherein Xaa$_{68}$ may be Arg or Gln.

In one embodiment, HCDR2 is of Formula (XX):

(XX) Y-I-Xaa$_{69}$-Xaa$_{70}$-Y-Xaa$_{71}$-G-Xaa$_{72}$-T-Xaa$_{73}$-Y-N-Xaa$_{74}$-Xaa$_{75}$-Xaa$_{76}$-Xaa$_{77}$-Xaa$_{78}$ (SEQ ID NO: 80)

wherein Xaa$_{69}$ to Xaa$_{78}$ may be a conservative or non conservative substitution or a deletion or insertion, preferably, wherein Xaa$_{69}$ may be Asp or His and/or Xaa$_{70}$ may be a deletion or Pro and/or Xaa$_{71}$ may be Ser or Asn and/or Xaa$_{72}$ may be Ile or Asp and/or Xaa$_{73}$ may be Ser or Asn and/or Xaa$_{74}$ may be Gln or Pro and/or Xaa$_{75}$ may be Lys or Ser and/or Xaa$_{76}$ may be Phe or Leu and/or Xaa$_{77}$ may be Lys or Arg and/or Xaa$_{78}$ may be Gly or Ser.

In one embodiment, HCDR2 is of Formula (XXI):

(XXI) Xaa$_{79}$-I-Xaa$_{80}$-Xaa$_{81}$-Y-Xaa$_{82}$-G-Xaa$_{83}$-T-Xaa$_{84}$-Xaa$_{85}$-N-Xaa$_{86}$-Xaa$_{87}$-Xaa$_{88}$-Xaa$_{89}$-Xaa$_{90}$ (SEQ ID NO: 81)

wherein Xaa$_{79}$ to Xaa$_{90}$ may be a conservative or non conservative substitution or a deletion or insertion, preferably, wherein Xaa$_{79}$ may be Arg or Tyr and/or Xaa$_{80}$ may be Asn, Asp or His and/or Xaa$_{81}$ may be a deletion or Pro and/or Xaa$_{82}$ may be Tyr, Asn or Ser and/or Xaa$_{83}$ may be Ile, Asp or Ala and/or Xaa$_{84}$ may be Ser or Asn and/or Xaa$_{85}$ may be a deletion or Tyr and/or Xaa$_{86}$ may be Pro, Arg or Gln and/or Xaa$_{87}$ may be Ser, Lys or Asn and/or Xaa$_{88}$ may be Phe or Leu and/or Xaa$_{89}$ may be Lys or Arg and/or Xaa$_{90}$ may be Asp or Gly.

In one embodiment, HCDR3 is of Formula (XXII):

(XXII) Xaa$_{91}$-Xaa$_{92}$-G-Xaa$_{93}$-Xaa$_{94}$-Y-Xaa$_{95}$-F-D-Y (SEQ ID NO: 82)

wherein Xaa$_{91}$ to Xaa$_{95}$ may be a conservative or non conservative substitution or a deletion or insertion, preferably, wherein Xaa$_{91}$ may be Asp or Ser, and/or Xaa$_{92}$ may be Asp or Gly, and/or Xaa$_{93}$ may be Gly or Asn, and/or Xaa$_{94}$ may be Asn or Thr, and/or Xaa$_{95}$ may be Pro or a deletion.

In one embodiment, HCDR3 is of Formula (XXIII):

(XXIII) Xaa$_{96}$-Xaa$_{97}$-Xaa$_{98}$-Xaa$_{99}$-Xaa$_{100}$-Y-Xaa$_{101}$-Xaa$_{102}$-D-Y (SEQ ID NO: 83)

wherein Xaa$_{96}$ to Xaa$_{102}$ may be a conservative or non conservative substitution or a deletion or insertion, preferably, wherein Xaa$_{96}$ may be S or D, and/or Xaa$_{97}$ may be G, T D, and/or Xaa$_{98}$ may be G, K or a deletion, and/or Xaa$_{99}$ may be G, L, N or a deletion, and/or Xaa$_{100}$ may be Y, T, G, N, and/or Xaa$_{101}$ may be P, G or a deletion, and/or Xaa$_{102}$ may be M, F or L.

In one embodiment, HCDR3 is of Formula (XXIV):

(XXIV) Xaa$_{103}$-Xaa$_{104}$-Xaa$_{105}$-Xaa$_{106}$-Xaa$_{107}$-Xaa$_{108}$-Xaa$_{109}$-F-D-Y (SEQ ID NO: 84)

wherein Xaa$_{103}$ to Xaa$_{109}$ may be a conservative or non conservative substitution or a deletion or insertion, preferably, wherein Xaa$_{103}$ may be Asp, Ser, Glu, and/or Xaa$_{104}$ may be Asp or Gly, and/or Xaa$_{105}$ may be Gly or Asn, and/or Xaa$_{106}$ may be Asn, Tyr or Gly, and/or Xaa$_{107}$ may be Asn, Thr or Tyr, and/or Xaa$_{108}$ may be Tyr or Gly, and/or Xaa$_{109}$ may be Tyr, Pro or a deletion In one embodiment, HCDR3 is of Formula (XXV):

Xaa$_{110}$-G-Xaa$_{111}$-Xaa$_{112}$-Y-Xaa$_{113}$-Xaa$_{114}$-Xaa$_{115}$-D-Y (XXV) (SEQ ID NO: 85)

wherein Xaa$_{110}$ to Xaa$_{115}$ may be a conservative or non conservative substitution or a deletion or insertion, preferably, wherein Xaa$_{110}$ may be Glu or Asp, and/or Xaa$_{111}$ may be Asn or a deletion, and/or Xaa$_{112}$ may be Tyr or a deletion, and/or Xaa$_{113}$ may be Tyr, or Gly, and/or Xaa$_{114}$ may be Tyr or Gly, and/or Xaa$_{115}$ may be Met or Phe.

In one embodiment, an antibody of the invention may comprise a light chain comprising:
a a light chain CDR1 (LCDR1) amino acid sequence selected from SEQ ID NOS: 61, 64 and 65; and/or
b a light chain CDR2 (LCDR2) amino acid sequence selected from SEQ ID NOS: 62, 66 and 67; and/or
c a light chain CDR3 (LCDR3) amino acid sequence selected from SEQ ID NOS: 63, 68, 69 and 70.

In one embodiment, an antibody of the invention may comprise a heavy chain comprising:
a a heavy chain CDR1 (HCDR1) amino acid sequence selected from SEQ ID NOS: 71 to 76; and/or
b a heavy chain CDR2 (HCDR2) amino acid sequence selected from SEQ ID NOS: 77 to 81; and/or
c a heavy chain CDR3 (HCDR3) amino acid sequence selected from SEQ ID NOS: 82 to 85.

Antibody 29H3

Cells producing antibody 29H3 have been deposited at the CNCM under accession number I-4187; the antibody 29H3 has also been sequenced. The amino acid sequence of the heavy chain variable region is listed as SEQ ID NO:10, the amino acid sequence of the light chain variable region is listed as SEQ ID NO:11. The nucleic acid sequence encoding the heavy and light chain variable regions are listed in SEQ ID NOS 53 and 54, respectively. In one embodiment, the invention provides an antibody that binds essentially the same epitope or determinant as monoclonal antibodies 29H3; optionally the antibody comprises an antigen binding region of antibody 29H3. In any of the embodiments herein, antibody 29H3 can be characterized by its amino acid sequence and/or nucleic acid sequence encoding it. In one preferred embodiment, the monoclonal antibody comprises the Fab or F(ab')$_2$ portion of 29H3. Also provided is a monoclonal antibody that comprises the heavy chain variable region of 29H3. According to one embodiment, the monoclonal antibody comprises the three CDRs of the heavy chain variable region of 29H3. Also provided is a monoclonal antibody that further comprises the variable light chain variable region of 29H3 or one, two or three of the CDRs of the light chain variable region of 29H3. Optionally any one or more of said light or heavy chain CDRs may contain one, two, three, four or five amino acid modifications (e.g. substitutions, insertions or deletions). Optionally, provided is an antibody where any of the light and/or heavy chain variable regions comprising part or all of an antigen binding region of antibody 29H3 are fused to an immunoglobulin constant region of the IgG type, optionally a human constant region, optionally an IgG1 or IgG4 isotype. In another preferred embodiment the antibody is 29H3.

In another aspect, the invention provides a purified polypeptide which encodes an antibody, wherein the antibody comprises: a VHCDR1 region comprising an amino acid sequence as set forth in SEQ ID NO:12, wherein one or more of these amino acids may be substituted by a different amino acid; a VHCDR2 region comprising an amino acid sequence as set forth in SEQ ID NO:13, wherein one or more of these amino acids may be substituted by a different amino acid; a VHCDR3 region comprising an amino acid sequence as set forth in SEQ ID NO:14, wherein one or more of these amino acids may be substituted by a different amino acid; a VLCDR1 region comprising an amino acid sequence as set forth in SEQ ID NO:15, wherein one or more of these amino acids may be substituted by a different amino acid; a VLCDR2 region comprising an amino acid sequence as set forth in SEQ ID NO:16, wherein one or more of these amino acids may be substituted by a different amino acid; and/or a VLCDR3 region comprising an amino acid sequence as set forth in SEQ ID NO:17, wherein one or more of these amino acids may be substituted by a different amino acid.

In still another aspect, the invention provides an antibody, which comprises a heavy chain and/or a light chain each having at least three CDRs, wherein one, two or three of at least three CDRs has the sequence of SEQ ID NO:12 to 14 and 15 to 17 for the respective the heavy and light chains, and which antibody specifically binds to TLR3 in acidic conditions.

In another aspect, the invention provides an antibody that binds human TLR3, comprising:
a the heavy chain variable region of SEQ ID NO:10, wherein one, two, three or more of these amino acids may be substituted by a different amino acid; or
b the light chain variable region of SEQ ID NO:11, wherein one, two, three or more of these amino acids may be substituted by a different amino acid; or
c the heavy chain variable region of SEQ ID NO:10, wherein one, two, three or more of these amino acids may be substituted by a different amino acid; and the light chain variable region of SEQ ID NO:11, wherein one or more of these amino acids may be substituted by a different amino acid; or
d the heavy chain CDR 1, 2 and 3 (HCDR1, HCDR2, HCDR3) amino acid sequences as shown in SEQ ID NO:12, 13 and 14, wherein one, two, three or more of these amino acids may be substituted by a different amino acid; or
e the light chain CDR 1, 2 and 3 (LCDR1, LCDR2, LCDR3) e amino acid sequences as shown in SEQ ID NO:15, 16 and 17, respectively, wherein one, two, three or more of these amino acids may be substituted by a different amino acid; or
f the heavy chain CDR 1, 2 and 3 (HCDR1, HCDR2, HCDR3) amino acid sequences as shown in SEQ ID NO: 12, 13 and 14, wherein one, two, three or more of these amino acids may be substituted by a different amino acid; and the light chain CDR 1, 2 and 3 (LCDR1, LCDR2, LCDR3) amino acid sequences as shown in SEQ ID NO: 15, 16 and 17, wherein one, two, three or more of these amino acids may be substituted by a different amino acid; or
g the heavy chain variable region which is at least 60%, 70%, 80%, 85%, 90% or 95% identical to the variable region having an amino acid sequence of SEQ ID NO:10, wherein one, two, three or more of these amino acids may be substituted by a different amino acid; or
h the light chain variable region which is at least 60%, 70%, 80%, 85%, 90% or 95% identical to the variable region having an amino acid sequence of SEQ ID NO:11, wherein one, two, three or more of these amino acids may be substituted by a different amino acid.

In another aspect of any of the embodiments herein, any of the CDRs 1, 2 and 3 of the heavy and light chains may be characterized as having an amino acid sequence that shares at least 50%, 60%, 70%, 80%, 85%, 90% or 95% sequence identity with the particular CDR or set of CDRs listed in the corresponding SEQ ID NO.

In another aspect, the invention provides an antibody that competes for TLR3 binding with a monoclonal antibody of (a) to (h), above.

Antibody 31C3

Cells producing antibody 31C3 have been deposited at the CNCM under accession number I-4186, also the antibody 31C3 has also been sequenced. The amino acid sequence of the heavy chain variable region is listed as SEQ ID NO: 2, the amino acid sequence of the light chain variable region is listed as SEQ ID NO: 3. The nucleic acid sequence encoding the heavy and light chain variable regions are listed in SEQ ID NOS 51 and 52, respectively. In a specific embodiment, the invention provides an antibody that binds essentially the same epitope or determinant as monoclonal antibodies 31C3; optionally the antibody comprises an antigen binding region of antibody 31C3. In any of the embodiments herein, antibody 31C3 can be characterized by its amino acid sequence and/or nucleic acid sequence encoding it. In one preferred embodiment, the monoclonal antibody comprises the Fab or F(ab')₂ portion of 31C3. Also provided is a monoclonal antibody that comprises the heavy chain variable region of 31C3. According to one embodiment, the monoclonal antibody comprises the three CDRs of the heavy chain variable region of 31C3 Also provided is a monoclonal antibody that further comprises the variable light chain variable region of 31C3 or one, two or three of the CDRs of the light chain variable region of 31C3. Optionally any one or more of said light or heavy chain CDRs may contain one, two, three, four or five amino acid modifications (e.g. substitutions, insertions or deletions). Optionally, provided is an antibody where any of the light and/or heavy chain variable regions comprising part or all of an antigen binding region of antibody 31C3 are fused to an immunoglobulin constant region of the IgG type, optionally a human constant region, optionally a human IgG1 or IgG4 isotype. In another preferred embodiment the antibody is 31C3.

In another aspect, the invention provides a purified polypeptide which encodes a antibody, wherein the antibody comprises: a VHCDR1 region comprising an amino acid sequence as set forth in SEQ ID NO:4, wherein one or more of these amino acids may be substituted by a different amino acid; a VHCDR2 region comprising an amino acid sequence as set forth in SEQ ID NO:5, wherein one or more of these amino acids may be substituted by a different amino acid; a VHCDR3 region comprising an amino acid sequence as set forth in SEQ ID NO:6, wherein one or more of these amino acids may be substituted by a different amino acid; a VLCDR1 region comprising an amino acid sequence as set forth in SEQ ID NO:7, wherein one or more of these amino acids may be substituted by a different amino acid; a VLCDR2 region comprising an amino acid sequence as set forth in SEQ ID NO:8, wherein one or more of these amino acids may be substituted by a different amino acid; a VLCDR3 region comprising an amino acid sequence as set forth in SEQ ID NO:9, wherein one or more of these amino acids may be substituted by a different amino acid.

In still another aspect, the invention provides an antibody, which comprises a heavy chain and/or a light chain each having at least three CDRs, wherein one, two or three of the at least three CDRs has the sequence of SEQ ID NO:4 to 6 and 7 to 9 for the respective the heavy and light chains, and which antibody specifically binds to TLR3 in acidic conditions.

In another aspect, the invention provides an antibody that binds human TLR3, comprising:
a the heavy chain variable region of SEQ ID NO:2, wherein one, two, three or more of these amino acids may be substituted by a different amino acid; or
b the light chain variable region of SEQ ID NO: 3, wherein one, two, three or more of these amino acids may be substituted by a different amino acid; or
c the heavy chain variable region of SEQ ID NO: 2, wherein one or more of these amino acids may be substituted by a different amino acid; and the light chain variable region of SEQ ID NO: 3, wherein one, two, three or more of these amino acids may be substituted by a different amino acid; or
d the heavy chain CDR 1 and 2 (HCDR1, HCDR2) amino acid sequences as shown in SEQ ID NO:4 and 5, wherein one, two, three or more of these amino acids may be substituted by a different amino acid, optionally wherein the heavy chain comprises CDR 1, 2 and 3 (HCDR1, HCDR2, HCDR3) amino acid sequences as shown in SEQ ID NO:4, 5 and 6, wherein one, two, three or more of these amino acids may be substituted by a different amino acid; or
e the light chain CDR 1, 2 and 3 (LCDR1, LCDR2, LCDR3) amino acid sequences as shown in SEQ ID NO: 7, 8 and 9, wherein one, two, three or more of these amino acids may be substituted by a different amino acid; or
f the heavy chain CDR 1, 2 and 3 (HCDR1, HCDR2, HCDR3) amino acid sequences as shown in SEQ ID NO: 4, 5 and 6, wherein one or more of these amino acids may be substituted by a different amino acid; and the light chain CDRs 1, 2 and 3 (LCDR1, LCDR2, LCDR3) amino acid sequences as shown in SEQ ID NO: 7, 8 and 9, wherein one, two, three or more of these amino acids may be substituted by a different amino acid; or
g the heavy chain variable region which is at least 60%, 70%, 80%, 85%, 90% or 95% identical to the variable region having an amino acid sequence of SEQ ID NO: 2, wherein one, two, three or more of these amino acids may be substituted by a different amino acid; or
h the light chain variable region which is at least 60%, 70%, 80%, 85%, 90% or 95% identical to the variable region having an amino acid sequence of SEQ ID NO: 3, wherein one, two, three or more of these amino acids may be substituted by a different amino acid.

In another aspect of any of the embodiments herein, any of the CDRs 1, 2 and 3 of the heavy and light chains may be characterized as having an amino acid sequence that shares at least 50%, 60%, 70%, 80%, 85%, 90% or 95% sequence identity with the particular CDR or set of CDRs listed in the corresponding SEQ ID NO.

In another aspect, the invention provides an antibody that competes for TLR3 binding with a monoclonal antibody of (a) to (h), above.

Antibody 23C8

The antibody 23C8 has been sequenced. The amino acid sequence of the heavy chain variable region is listed as SEQ ID NO:26, the amino acid sequence of the light chain variable region is listed as SEQ ID NO:27. The nucleic acid sequence encoding the heavy and light chain variable regions are listed in SEQ ID NOS 57 and 58, respectively. In a specific embodiment, the invention provides an antibody that binds essentially the same epitope or determinant as monoclonal antibodies 23C8; optionally the antibody comprises an antigen binding region of antibody 23C8. In any of the embodiments herein, antibody 23C8 can be characterized by its amino acid sequence and/or nucleic acid sequence encoding it. In one preferred embodiment, the monoclonal antibody comprises the Fab or F(ab')2 portion of 23C8. Also provided is a monoclonal antibody that comprises the heavy chain variable region of 23C8. According to one embodiment, the monoclonal antibody comprises the three CDRs of the heavy chain variable region of 23C8. Also provided is a monoclonal antibody that further comprises the variable light chain variable region of 23C8 or one, two or three of the CDRs of the light chain variable region of 23C8. Optionally any one or more of said light or heavy chain CDRs may contain one, two, three, four or five amino acid modifications (e.g. substitutions, insertions or deletions). Optionally, provided is an antibody where any of the light and/or heavy chain variable regions comprising part or all of an antigen binding region of antibody 23C8 are fused to an immunoglobulin constant region of the IgG type, optionally a human constant region, optionally a human IgG1 or IgG4 isotype. In another preferred embodiment the antibody is 23C8.

In another aspect, the invention provides a purified polypeptide which encodes an antibody, wherein the antibody comprises: a VHCDR1 region comprising an amino acid sequence as set forth in SEQ ID NO:28, wherein one or more of these amino acids may be substituted by a different amino acid; a VHCDR2 region comprising an amino acid sequence as set forth in SEQ ID NO:29, wherein one or more of these amino acids may be substituted by a different amino acid; a VHCDR3 region comprising an amino acid sequence as set forth in SEQ ID NO:30, wherein one or more of these amino acids may be substituted by a different amino acid; a VLCDR1 region comprising an amino acid sequence as set forth in SEQ ID NO:31, wherein one or more of these amino acids may be substituted by a different amino acid; a VLCDR2 region comprising an amino acid sequence as set forth in SEQ ID NO:32, wherein one or more of these amino acids may be substituted by a different amino acid; a VLCDR3 region comprising an amino acid sequence as set forth in SEQ ID NO:33, wherein one or more of these amino acids may be substituted by a different amino acid.

In still another aspect, the invention provides an antibody, which comprises a heavy chain and/or a light chain each having at least three CDRs, wherein one, two or three of at least three CDRs has the sequence of SEQ ID NO:28 to 30 and 31 to 33 for the respective the heavy and light chains, and which antibody specifically binds to TLR3 in acidic conditions.

In another aspect, the invention provides an antibody that binds human TLR3, comprising:
  a the heavy chain variable region of SEQ ID NO: 26, wherein one, two, three or more of these amino acids may be substituted by a different amino acid; or
  b the light chain variable region of SEQ ID NO: 27, wherein one, two, three or more of these amino acids may be substituted by a different amino acid; or
  c the heavy chain variable region of SEQ ID NO: 26, wherein one, two, three or more of these amino acids may be substituted by a different amino acid; and the light chain variable region of SEQ ID NO: 27, wherein one, two, three or more of these amino acids may be substituted by a different amino acid; or
  d the heavy chain CDR 1 and 2 (HCDR1, HCDR2) amino acid sequences as shown in SEQ ID NO: 28 and 29, wherein one, two, three or more of these amino acids may be substituted by a different amino acid; optionally wherein the heavy chain comprises the CDR 1, 2 and 3 (HCDR1, HCDR2, HCDR3) amino acid sequences as shown in SEQ ID NO: 28, 29 and 30, wherein one, two, three or more of these amino acids may be substituted by a different amino acid; or
  e the light chain CDR 1, 2 and 3 (LCDR1, LCDR2, LCDR3) amino acid sequences as shown in SEQ ID NO: 31, 32 and 33, wherein one, two, three or more of these amino acids may be substituted by a different amino acid; or
  f the heavy chain CDR 1, 2 and 3 (HCDR1, HCDR2, HCDR3) amino acid sequences as shown in SEQ ID NO: 28, 29 and 30, wherein one, two, three or more of these amino acids may be substituted by a different amino acid; and the light chain CDR 1, 2 and 3 (LCDR1, LCDR2, LCDR3) amino acid sequences as shown in SEQ ID NO: 31, 32 and 33, wherein one, two, three or more of these amino acids may be substituted by a different amino acid; or
  g the heavy chain variable region which is at least 60%, 70%, 80%, 85%, 90% or 95% identical to the variable region having an amino acid sequence of SEQ ID NO: 26, wherein one, two, three or more of these amino acids may be substituted by a different amino acid; or
  h the light chain variable region which is at least 60%, 70%, 80%, 85%, 90% or 95% identical to the variable region having an amino acid sequence of SEQ ID NO: 27, wherein one, two, three or more of these amino acids may be substituted by a different amino acid.

In another aspect of any of the embodiments herein, any of the CDRs 1, 2 and 3 of the heavy and light chains may be characterized as having an amino acid sequence that shares at least 50% 60%, 70%, 80%, 85%, 90% or 95% sequence identity with the particular CDR or set of CDRs listed in the corresponding SEQ ID NO.

In another aspect, the invention provides an antibody that competes for TLR3 binding with a monoclonal antibody of (a) to (h), above.

Antibody 28F11

The antibody 28F11 has been sequenced. The amino acid sequence of the heavy chain variable region is listed as SEQ ID NO:18, the amino acid sequence of the light chain variable region is listed as SEQ ID NO:19. The nucleic acid sequence encoding the heavy and light chain variable regions are listed in SEQ ID NOS 55 and 56, respectively. In a specific embodiment, the invention provides an antibody that binds essentially the same epitope or determinant as monoclonal antibodies 28F11; optionally the antibody comprises an antigen binding region of antibody 28F11. In any of the embodiments herein, antibody 28F11 can be characterized by its amino acid sequence and/or nucleic acid sequence encoding it. In one preferred embodiment, the monoclonal antibody comprises the Fab or F(ab')2 portion of 28F11. Also provided is a monoclonal antibody that comprises the heavy chain variable region of 28F11. According to one embodiment, the monoclonal antibody comprises the three CDRs of the heavy chain variable region of 28F11. Also provided is a monoclonal antibody that further comprises the variable light chain variable region of 28F11 or one, two or three of the CDRs of the light chain variable region of 28F11. Optionally any one or more of said light or heavy chain CDRs may contain one, two, three, four or five amino acid modifications (e.g. substitutions, insertions or deletions). Optionally, provided is an antibody where any of the light and/or heavy chain variable regions comprising part or all of an antigen binding region of antibody 28F11 are fused to an immunoglobulin constant region of the IgG type, optionally a human constant region, optionally a human IgG1 or IgG4 isotype. In another preferred embodiment the antibody is 28F11.

In another aspect, the invention provides a purified polypeptide which encodes a antibody, wherein the antibody comprises: a VHCDR1 region comprising an amino acid sequence as set forth in SEQ ID NO:20, wherein one or more of these amino acids may be substituted by a different amino acid; a VHCDR2 region comprising an amino acid sequence as set forth in SEQ ID NO:21, wherein one or more of these amino acids may be substituted by a different amino acid; a VHCDR3 region comprising an amino acid sequence as set forth in SEQ ID NO:22, wherein one or more of these amino acids may be substituted by a different amino acid; a VLCDR1 region comprising an amino acid sequence as set forth in SEQ ID NO:23, wherein one or more of these amino acids may be substituted by a different amino acid; a VLCDR2 region comprising an amino acid sequence as set forth in SEQ ID NO:24, wherein one or more of these amino acids may be substituted by a different amino acid; a VLCDR3 region comprising an amino acid sequence as set forth in SEQ ID NO:25, wherein one or more of these amino acids may be substituted by a different amino acid.

In still another aspect, the invention provides an antibody, which comprises a heavy chain and/or a light chain each having at least three CDRs, wherein one, two or three of at least three CDRs has the sequence of SEQ ID NO: 20 to 22 and 23 to 25 for the respective heavy and light chains, and which antibody specifically binds to TLR3 in acidic conditions.

In another aspect, the invention provides an antibody that binds human TLR3, comprising:

a the heavy chain variable region of SEQ ID NO: 18, wherein one, two, three or more of these amino acids may be substituted by a different amino acid; or b the light chain variable region of SEQ ID NO: 19, wherein one, two, three or more of these amino acids may be substituted by a different amino acid; or c the heavy chain variable region of SEQ ID NO: 18, wherein one, two, three or more of these amino acids may be substituted by a different amino acid; and the light chain variable region of SEQ ID NO: 19, wherein one, two, three or more of these amino acids may be substituted by a different amino acid; or d the heavy chain CDR 1 and 2 (HCDR1, HCDR2) amino acid sequences as shown in SEQ ID NO: 20 and 21, wherein one, two, three or more of these amino acids may be substituted by a different amino acid; optionally wherein heavy chain comprises CDR 1, 2 and 3 (HCDR1, HCDR2, HCDR3) amino acid sequences as shown in SEQ ID NO: 20, 21 and 22, wherein one, two, three or more of these amino acids may be substituted by a different amino acid; or e the light chain CDR 1, 2 and 3 (LCDR1, LCDR2, LCDR3) amino acid sequences as shown in SEQ ID NO: 23, 24 and 25, wherein one, two, three or more of these amino acids may be substituted by a different amino acid; or f the heavy chain CDR 1, 2 and 3 (HCDR1, HCDR2, HCDR3) amino acid sequences as shown in SEQ ID NO: 20, 21 and 22, wherein one, two, three or more of these amino acids may be substituted by a different amino acid; and the light chain CDR 1, 2 and 3 (LCDR1, LCDR2, LCDR3) amino acid sequences as shown in SEQ ID NO: 23, 24 and 25, wherein one, two, three or more of these amino acids may be substituted by a different amino acid; or g the heavy chain variable region which is at least 60%, 70%, 80%, 85%, 90% or 95% identical to the variable region having an amino acid sequence of SEQ ID NO: 18, wherein one, two, three or more of these amino acids may be substituted by a different amino acid; or h the light chain variable region which is at least 60%, 70%, 80%, 85%, 90% or 95% identical to the variable region having an amino acid sequence of SEQ ID NO: 19, wherein one, two, three or more of these amino acids may be substituted by a different amino acid.

In another aspect of any of the embodiments herein, any of the CDRs 1, 2 and 3 of the heavy and light chains may be characterized as having an amino acid sequence that shares at least 50%, 60%, 70%, 80%, 85%, 90% or 95% sequence identity with the particular CDR or set of CDRs listed in the corresponding SEQ ID NO.

In another aspect, the invention provides an antibody that competes for TLR3 binding with a monoclonal antibody of (a) to (h), above.

Antibody 34A3

The antibody 34A3 has been sequenced. The amino acid sequence of the heavy chain variable region is listed as SEQ ID NO:34, the amino acid sequence of the light chain variable region is listed as SEQ ID NO:35. The nucleic acid sequence encoding the heavy and light chain variable regions are listed in SEQ ID NOS 59 and 60, respectively. In a specific embodiment, the invention provides an antibody that binds essentially the same epitope or determinant as monoclonal antibodies 34A3; optionally the antibody comprises an antigen binding region of antibody 34A3. In any of the embodiments herein, antibody 34A3 can be characterized by its amino acid sequence and/or nucleic acid sequence encoding it. In one preferred embodiment, the monoclonal antibody comprises the Fab or F(ab')2 portion of 34A3. Also provided is a monoclonal antibody that comprises the heavy chain variable region of 34A3. According to one embodiment, the monoclonal antibody comprises the three CDRs of the heavy chain variable region of 34A3. Also provided is a monoclonal antibody that further comprises the variable light chain variable region of 34A3 or one, two or three of the CDRs of the light chain variable region of 34A3. Optionally any one or more of said light or heavy chain CDRs may contain one, two, three, four or five amino acid modifications (e.g. substitutions, insertions or deletions). Optionally, provided is an antibody where any of the light and/or heavy chain variable regions comprising part or all of an antigen binding region of antibody 34A3 are fused to an immunoglobulin constant region of the IgG type, optionally a human constant region, optionally a human IgG1 or IgG4 isotype. In another preferred embodiment the antibody is 34A3.

In another aspect, the invention provides a purified polypeptide which encodes a antibody, wherein the antibody comprises: a VHCDR1 region comprising an amino acid sequence as set forth in SEQ ID NO:36, wherein one or more of these amino acids may be substituted by a different amino acid; a VHCDR2 region comprising an amino acid sequence as set forth in SEQ ID NO:37, wherein one or more of these amino acids may be substituted by a different amino acid; a VHCDR3 region comprising an amino acid sequence as set forth in SEQ ID NO:38, wherein one or more of these amino acids may be substituted by a different amino acid; a VLCDR1 region comprising an amino acid sequence as set forth in SEQ ID NO:39, wherein one or more of these amino acids may be substituted by a different amino acid; a VLCDR2 region comprising an amino acid sequence as set forth in SEQ ID NO:40, wherein one or more of these amino acids may be substituted by a different amino acid; a VLCDR3 region comprising an amino acid sequence as set forth in SEQ ID NO:41, wherein one or more of these amino acids may be substituted by a different amino acid.

In still another aspect, the invention provides an antibody, which comprises a heavy chain and/or a light chain each having at least three CDRs, wherein one, two or three of at least three CDRs has the sequence of SEQ ID NO:36 to 38 and 29 to 41 for the respective heavy and light chains, and which antibody specifically binds to TLR3 in acidic conditions.

In another aspect, the invention provides an antibody that binds human TLR3, comprising:

a the heavy chain variable region of SEQ ID NO: 34, wherein one, two, three or more of these amino acids may be substituted by a different amino acid; or
b the light chain variable region of SEQ ID NO: 35, wherein one, two, three or more of these amino acids may be substituted by a different amino acid; or
c the heavy chain variable region of SEQ ID NO: 34, wherein one, two, three or more of these amino acids may be substituted by a different amino acid; and the light chain variable region of SEQ ID NO: 35, wherein one, two, three or more of these amino acids may be substituted by a different amino acid; or
d the heavy chain CDRs 1, 2 and 3 (HCDR1, HCDR2, HCDR3) amino acid sequences as shown in SEQ ID NO: 36, 37 and 38, wherein one, two, three or more of these amino acids may be substituted by a different amino acid; or
e the light chain CDRs 1, 2 and 3 (LCDR1, LCDR2, LCDR3) amino acid sequences as shown in SEQ ID NO: 39, 40 and 41, wherein one or more of these amino acids may be substituted by a different amino acid; or
f the heavy chain CDRs 1, 2 and 3 (HCDR1, HCDR2, HCDR3) amino acid sequences as shown in SEQ ID NO: 36, 37 and 38, wherein one, two, three or more of these amino acids may be substituted by a different amino acid; and the light chain CDRs 1, 2 and 3 (LCDR1, LCDR2, LCDR3) amino acid sequences as shown in SEQ ID NO: 39, 40 and 41, wherein one, two, three or more of these amino acids may be substituted by a different amino acid; or
g the heavy chain variable region which is at least 60%, 70%, 80%, 85%, 90% or 95% identical to the variable region having an amino acid sequence of SEQ ID NO: 34, wherein one, two, three or more of these amino acids may be substituted by a different amino acid; or
h the light chain variable region which is at least 60%, 70%, 80%, 85%, 90% or 95% identical to the variable region having an amino acid sequence of SEQ ID NO: 35, wherein one, two, three or more of these amino acids may be substituted by a different amino acid.

In another aspect of any of the embodiments herein, any of the CDRs 1, 2 and 3 of the heavy and light chains may be characterized as having an amino acid sequence that shares at least 50%, 60%, 70%, 80%, 85%, 90% or 95% sequence identity with the particular CDR or set of CDRs listed in the corresponding SEQ ID NO.

In another aspect, the invention provides an antibody that competes for TLR3 binding with a monoclonal antibody of (a) to (h), above.

In any of the antibodies of the invention, e.g, 31C3, 29H3, 23C8, 28F11 or 34A3, the specified variable region and CDR sequences may comprise conservative sequence modifications. Conservative sequence modifications refers to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are typically those in which an amino acid residue is replaced with an amino acid residue having a side chain with similar physicochemical properties. Specified variable region and CDR sequences may comprise one, two, three, four or more amino acid insertions, deletions or substitutions. Where substitutions are made, preferred substitutions will be conservative modifications. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g. threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the properties set forth herein) using the assays described herein.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

The sequences of the CDRs of the antibodies according to the invention, according to AbM (Oxford Molecular's AbM antibody modelling software definition), Kabat and Chothia definitions systems, have been summarized in Table A below. The amino acids sequences described herein are numbered according to Abm, Kabat and Chothia numbering systems. While any suitable numbering system may be used to designated CDR regions, in the absence of any other indication, the numbering used herein is Abm. Such numbering has been established using the following indications: CDR-L1: Start: approx residue 24, residue before: always a Cys, residue after: always a Trp (typically Trp-Tyr-Gln, but also, Trp-Leu-Gln, Trp-Phe-Gln, Trp-Tyr-Leu), length: 10 to 17 residues; CDR-L2: Start: always 16 residues after the end of L1, Residues before: generally Ile-Tyr (but also, Val-Tyr, Ile-Lys, Ile-Phe), Length: always 7 residues; CDR-L3, Start: always 33 residues after end of L2, Residue before: always Cys, Residues after: always Phe-Gly-Xaa-Gly, Length: 7 to 11 residues; CDR-H1, Start: approx residue 26 (always 4 after a Cys) (Chothia/AbM definition, the Kabat definition starts 5 residues later), Residues before: always Cys-Xaa-Xaa-Xaa, Residues after: always a Trp (typically Trp-Val, but also, Trp-Ile, Trp-Ala), Length: 10 to 12 residues (AbM definition, Chothia definition excludes the last 4 residues); CDR-H2, Start: always 15 residues after the end of Kabat/AbM definition of CDR-H1, Residues before: typically Leu-Glu-Trp-Ile-Gly (but a number of variations, Residues after Lys/Arg-Leu/Ile/Val/Phe/Thr/Ala-Thr/Ser/Ile/Ala), Length: Kabat definition 16 to 19 residues; AbM (and Chothia) definition ends 7 residues earlier; CDR-H3, Start: always 33 residues after end of CDR-H2 (always 2 after a Cys), Residues before: always Cys-Xaa-Xaa (typically Cys-Ala-Arg), Residues after: always Trp-Gly-Xaa-Gly, Length: 3 to 25 residues.

The sequences of the variable chains of the antibodies according to the invention are listed in Table B below, signal peptide sequence is represented in italics, and the CDRs are provided in bold. The term x/x indicates that any of the two indicated amino acids can be present at the particular amino acid residue, for instance, the term F/S means that at the given position, the amino acid can be either phenylalanine or serine. In any embodiment herein, a VL or VH sequence can be specified or numbered so as to contain or lack the signal peptide or any part thereof.

In an embodiment, the antibodies of the invention are of the human or mouse IgG1 isotype. In another embodiment, the antibodies of the invention are of the human IgG4 isotype In an embodiment, the antibodies of the invention are antibody fragments that retain their binding and/or functional properties.

TABLE A

| mAb | CDR definition | SEQ ID | HCDR1 Sequence | SEQ ID | HCDR2 Sequence | SEQ ID | HCDR3 Sequence |
|---|---|---|---|---|---|---|---|
| 23C8 | Abm | 28 | GYSFTGYFMH | 29 | RINPYNGATS | 30 | DDGGNYPFDY |
|  | Chotia |  | GYSFTG |  | RINPYNGATS |  | DDGGNYPFDY |
|  | Kabat |  | GYFMH |  | RINPYNGATSYNQNFKD |  | DDGGNYPFDY |
| 29H3 | Abm | 12 | GYSITSGYSWH | 13 | YIHYSGITN | 14 | DGYYGMDY |
|  | Chotia |  | GYSITSG |  | YIHYSGITN |  | DGYYGMDY |
|  | Kabat |  | SGYSWH |  | YIHYSGITNYNPSLRS |  | DGYYGMDY |
| 28F11 | Abm | 20 | GYSFTGYYIH | 21 | RINPYYGAT | 22 | STKLGYLDY |
|  | Chotia |  | GYSFTG |  | RINPYYGAT |  | STKLGYLDY |
|  | Kabat |  | GYYIH |  | RINPYYGATSNQNFKD |  | STKLGYLDY |
| 31C3 | Abm | 4 | GYSFTAYYMH | 5 | RINPYNGATS | 6 | SGGNTYFDY |
|  | Chotia |  | GYSFTA |  | RINPYNGATS |  | SGGNTYFDY |
|  | Kabat |  | AYYMH |  | RINPYNGATSYNRNFKD |  | SGGNTYFDY |
| 34A3 | Abm | 36 | GYVFTTYSIY | 37 | YIDPYNGDTS | 38 | EGNYYGYFDY |
|  | Chotia |  | GYVFTT |  | YIDPYNGDTS |  | EGNYYGYFDY |
|  | Kabat |  | TYSIY |  | YIDPYNGDTSYNQKFKG |  | EGNYYGYFDY |

TABLE B

| Antibody portion | SEQ ID NO | |
|---|---|---|
| 23C8 VL | 27 | *MSVPTQVLGL LLLWLTGARC* DIQMTQSPAS LSASVGETVT ITCRASENIY SYLAWYQQKQ GKSPQLLVYY AKTLAEGVPS RFSGSGTGTQ FSLKINSLQP EDFGSYYCQH HYGTPYTFGG GTKLEIK |
| 23C8 VH | 26 | *MGWSWIFLFL LSGTAGVLSE* VQLQQSGPEL VKPGASVKIS CKASGYSFTG YFMHWVKQSH VKSLEWIGRI NPYNGATSYN QNFKDKASLT VDKSSSTSYM ELHSLTSEDS AVYYCVRDDG GNYPFDYWGQ GTTLTVS |

TABLE B-continued

| Antibody portion | SEQ ID NO | |
|---|---|---|
| 28F11 VL | 19 | MSVPTQVLGL LLLWLTGARC DIQMTQSPAS LSASVGETVT ITCRASENIY SNLAWYQQKQ GKSPQLLIYN AKTLAEGVPS RFSGSGSGTQ YFLKINSLQP EDFGSYYCQH HYGTPFTFGG GTKLEIK |
| 28F11 VH | 18 | MGWSWIFLFL LSGTAGVLSE VQLQQSGPEL VKPGASVKIS CKASGYSFTG YYIHWVKQSH VKSLEWIGRI NPYYGATSNQ NFKDKANLTV DKSSSTAYME LHSLTSDDSA VYYCARSTKL GYLDYWGQGT TLTVS |
| 29H3 VL | 11 | MDFQTQVFVF VLLWLSGVDG DIVMTQSQKF MSTSVGDRVS ITCKASQNVR TSVAWYQQKP GQSPKALIYL ASNRHTGVPD RFTGSGSGTD FTLTVSNIQS EDLADYFCLQ HWNYPYTFGG GTKLEIK |
| 29H3 VH | 10 | MRVLILLCLF TAFPGILSDV QLQESGPDLV KPSQSLSLTC TVTGYSITSG YSWHWIRQFL GNKLEWMGYI HYSGITNYNP SLRSRISFTR DTSKNQFFLQ LNSVTTEDTA TYYCARDGYY GMDYWGQGTS VTVS |
| 31C3 VL | 3 | MSVPTQVLGL LLLWLTGARC DIQMTQSPAS LSASVGETVT ITCRASENIY SSLAWYQQKQ GKSPQLLVYN AKTLAEGVPS RFSGSGSGTQ F/SSLKINSLQP EDFGTYYCQH HYGTPPTFGG GTKLEIK |
| 31C3 VH | 2 | MGWSWIFLFL LSGTAGVLSE VQLQQSGPEL VKPGASVKIS CKPSGYSFTA YYMHWVKQSH VKSLEWIGRI NPYNGATSYN RNFKDKASLT VDKSSSTAYM ELHSLTSEDS AVYYCARSGG NTYFDYWGQG TTLTVS |
| 34A3 VL | 35 | MDFQVQIFSF LLMSASVIMS RGQIVLTQSP ALMSASPGEK VTMTCSASSSV SYMFWYQQKP RSSPKPWIYL TSNLASGVPA RFSGSGSGTS YSLTISSMEA EDAATYYCQQ WTGNPPTFGG GTKLEIK |
| 34A3 VH | 34 | MEWRWIFLFL LSGTTGVHSE IQLQQSGPEL VKPGASVKVS CKASGYVFTT YSIYWVKQSH GKSLEWIGYI DPYNGDTSYN QKFKGKATLT VDKSSSTAYM HLNSLTSEDS TVYYCAREGN YYGYFDYWGQ GTTLTVS |

The sequencing of light and heavy chains of the anti-TLR3 antibodies according to the invention led to the identification of the genes rearrangement involved in the generation of such antibodies, as summarized in Table C below. (The gene sequences indicated are can be retrieved at www.ncbi.nlm.nih.gov/igblast/showGermline.cgi). FIGS. 18A and 18B represent the phylogenetic trees (generated by Phylip's Drawtree) of the light and heavy chains, indicating a high degree of homology between antibodies 28F11, 31C3 and 23C8.

TABLE C

| | Light Chain | | Heavy Chain | |
|---|---|---|---|---|
| | V gene | J gene | V gene | J gene |
| 29H3 | VK 19-14 | JK2 | VH3 VH36-60.a1.85 | JH4 |
| | SEQ ID NO: 42 | SEQ ID NO: 45 | SEQ ID NO: 46 | SEQ ID NO: 50 |
| 34A3 | VK aq4 (VK) | JK2 | VH1 VH J558.1 | JH2 |
| | SEQ ID NO: 43 | SEQ ID NO: 45 | SEQ ID NO: 47 | SEQ ID NO: 49 |
| 23C8 | VK 12-41 or 12-44 | JK2 | VH1 VH J558.2 | JH2 |
| | SEQ ID NO: 44 | SEQ ID NO: 45 | SEQ ID NO: 48 | SEQ ID NO: 49 |
| 31C3 | VK 12-41 or 12-44 | JK2 | VH1 VH J558.2 | JH2 |
| | SEQ ID NO: 44 | SEQ ID NO: 45 | SEQ ID NO: 48 | SEQ ID NO: 49 |
| 28F11 | VK 12-41 or 12-44 | JK2 | VH1 VH J558.2 | JH2 |
| | SEQ ID NO: 44 | SEQ ID NO: 45 | SEQ ID NO: 48 | SEQ ID NO: 49 |

Table D below provides the percentage sequence identity between the different CDRs for each antibody, in amino acids.

TABLE D

|  | 31C3 | 29H3 | 23C8 | 28F11 | 34A3 |
|---|---|---|---|---|---|
| CDR VL | | | | | |
| 31C3 | 100.00 | 33.33 | 88.89 | 92.59 | 37.04 |
| 29H3 |  | 100.00 | 33.33 | 29.63 | 29.63 |
| 23C8 |  |  | 100.00 | 88.89 | 33.33 |
| 28F11 |  |  |  | 100.00 | 33.33 |
| 34A3 |  |  |  |  | 100.00 |
| CDR1 VL | | | | | |
| 31C3 | 100.00 | 45.45 | 90.91 | 90.91 | 27.27 |
| 29H3 |  | 100.00 | 45.45 | 27.27 | 27.27 |
| 23C8 |  |  | 100.00 | 90.91 | 27.27 |
| 28F11 |  |  |  | 100.00 | 36.36 |
| 34A3 |  |  |  |  | 100.00 |
| CDR2 VL | | | | | |
| 31C3 | 100.00 | 14.29 | 85.71 | 100.00 | 28.57 |
| 29H3 |  | 100.00 | 14.29 | 14.29 | 42.86 |
| 23C8 |  |  | 100.00 | 85.71 | 28.57 |
| 28F11 |  |  |  | 100.00 | 28.57 |
| 34A3 |  |  |  |  | 100.00 |
| CDR3 VL | | | | | |
| 31C3 | 100.00 | 33.33 | 88.89 | 85.71 | 33.33 |
| 29H3 |  | 100.00 | 44.44 | 27.27 | 22.22 |
| 23C8 |  |  | 100.00 | 88.89 | 44.44 |
| 28F11 |  |  |  | 100.00 | 44.44 |
| 34A3 |  |  |  |  | 100.00 |
| CDR VH | | | | | |
| 31C3 | 100.00 | 39.47 | 78.38 | 70.27 | 50.00 |
| 29H3 |  | 100.00 | 44.74 | 39.47 | 39.47 |
| 23C8 |  |  | 100.00 | 70.27 | 52.63 |
| 28F11 |  |  |  | 100.00 | 47.37 |
| 34A3 |  |  |  |  | 100.00 |
| CDR1 VH | | | | | |
| 31C3 | 100.00 | 54.55 | 80.00 | 80.00 | 45.45 |
| 29H3 |  | 100.00 | 63.64 | 63.64 | 45.45 |
| 23C8 |  |  | 100.00 | 80.00 | 45.45 |
| 28F11 |  |  |  | 100.00 | 54.55 |
| 34A3 |  |  |  |  | 100.00 |
| CDR2 VH | | | | | |
| 31C3 | 100.00 | 35.29 | 94.12 | 82.35 | 64.71 |
| 29H3 |  | 100.00 | 35.29 | 29.41 | 35.29 |
| 23C8 |  |  | 100.00 | 88.24 | 70.59 |
| 28F11 |  |  |  | 100.00 | 58.82 |
| 34A3 |  |  |  |  | 100.00 |
| CDR3 VH | | | | | |
| 31C3 | 100.00 | 40.00 | 50.00 | 44.44 | 40.00 |
| 29H3 |  | 100.00 | 40.00 | 30.00 | 40.00 |
| 23C8 |  |  | 100.00 | 30.00 | 30.00 |
| 28F11 |  |  |  | 100.00 | 20.00 |
| 34A3 |  |  |  |  | 100.00 |

Table E provides the identity percentage has been calculated between the different VL and VH (italics) nucleotide sequences for each antibody using LALIGN software.

TABLE E

| VL | VH | | | | |
|---|---|---|---|---|---|
|  | 23C8 | 28F11 | 29H3 | 31C3 | 34A3 |
| 23C8 | 100 | 93.5 | 60.6 | 94.9 | 87.3 |
| 28F11 | 97.6 | 100 | 60.4 | 94.4 | 87.8 |
| 29H3 | 65.8 | 65.2 | 100 | 61.0 | 60.6 |
| 31C3 | 96.1 | 95.5 | 63.9 | 100 | 89.1 |
| 34A3 | 64.6 | 65.3 | 67.2 | 64.0 | 100 |

Table F provides the identity percentage has been calculated between the different VL and VH (italics) amino acid sequences using LALIGN software.

TABLE F

| VL | VH | | | | |
|---|---|---|---|---|---|
|  | 23C8 | 28F11 | 29H3 | 31C3 | 34A3 |
| 23C8 | 100 | 89.8 | 48.9 | 92.7 | 79.1 |
| 28F11 | 94.5 | 100 | 47.0 | 91.2 | 79.6 |
| 29H3 | 54.3 | 54.3 | 100 | 47.8 | 48.1 |
| 31C3 | 96.1 | 95.3 | 55.1 | 100 | 79.6 |
| 34A3 | 52.7 | 53.5 | 55.4 | 54.3 | 100 |

Fragments and Derivatives of the Present Monoclonal Antibodies

Fragments and derivatives of antibodies of this invention (which are encompassed by the term "antibody" or "antibodies" as used in this application, unless otherwise stated or clearly contradicted by context), preferably a 31C3, 29H3, 23C8, 28F11 or 34A3-like antibody, can be produced by techniques that are known in the art. "Fragments" comprise a portion of the intact antibody, generally the antigen binding site or variable region. Examples of antibody fragments include Fab, Fab', Fab'-SH, F (ab') 2, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific antibodies formed from antibody fragments.

Fragments of the present antibodies can be obtained using standard methods. For instance, Fab or F (ab') 2 fragments may be produced by protease digestion of the isolated antibodies, according to conventional techniques. It will be appreciated that immunoreactive fragments can be modified using known methods, for example to slow clearance in vivo and obtain a more desirable pharmacokinetic profile the fragment may be modified with polyethylene glycol (PEG). Methods for coupling and site-specifically conjugating PEG to a Fab' fragment are described in, for example, Leong et al, 16 (3): 106-119 (2001) and Delgado et al, Br. J. Cancer 73 (2): 175-182 (1996), the disclosures of which are incorporated herein by reference.

Alternatively, the DNA of a hybridoma producing an antibody of the invention, preferably a 31C3, 29H3, 23C8, 28F11 or 34A3-like antibody, may be modified so as to encode a fragment of the invention. The modified DNA is then inserted into an expression vector and used to transform or transfect an appropriate cell, which then expresses the desired fragment.

In certain embodiments, the DNA of a hybridoma producing an antibody of this invention, preferably a 31C3, 29H3, 23C8, 28F11 or 34A3-like antibody, can be modified prior to insertion into an expression vector, for example, by substituting the coding sequence for human heavy- and light-chain constant domains in place of the homologous non-human sequences (e.g., Morrison et al., PNAS pp. 6851 (1984)), or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody of the invention.

Thus, according to another embodiment, the antibody of this invention, preferably a 31C3, 29H3, 23C8, 28F11 or 34A3-like antibody, is humanized. "Humanized" forms of antibodies according to this invention are specific chimeric immunoglobulins, immunoglobulin chains or fragments thereof (such as Fv, Fab, Fab', F (ab') 2, or other antigen-binding subsequences of antibodies) which contain minimal sequence derived from the murine immunoglobulin. For the most part, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody.

In some instances, Fv framework residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. The humanized antibody optimally also will comprise at least a portion of an immunoglobulin constant region (Fc), typically that of a human immunoglobulin. For further details see Jones et al., Nature, 321, pp. 522 (1986); Reichmann et al, Nature, 332, pp. 323 (1988); Presta, Curr. Op. Struct. Biol., 2, pp. 593 (1992); Verhoeyen et Science, 239, pp. 1534; and U.S. Pat. No. 4,816,567, the entire disclosures of which are herein incorporated by reference.) Methods for humanizing the antibodies of this invention are well known in the art.

The choice of human variable domains, both light and heavy, to be used in making the humanized antibodies is very important to reduce antigenicity. According to the so-called "best-fit" method, the sequence of the variable domain of an antibody of this invention is screened against the entire library of known human variable-domain sequences. The human sequence which is closest to that of the mouse is then accepted as the human framework (FR) for the humanized antibody (Sims et al., J. Immunol. 151, pp. 2296 (1993); Chothia and Lesk, J. Mol. 196, pp. 901). Another method uses a particular framework from the consensus sequence of all human antibodies of a particular subgroup of light or heavy chains. The same framework can be used for several different humanized antibodies (Carter et al., PNAS 89, pp. 4285 (1992); Presta et J. Immunol., 51, p. 1993)).

It is further important that antibodies be humanized with retention of high affinity for TLR3 receptors and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen (s), is achieved. In general, the CDR residues are directly and most substantially involved in influencing antigen binding.

Another method of making "humanized" monoclonal antibodies is to use a XenoMouse (Abgenix, Fremont, Calif.) as the mouse used for immunization. A XenoMouse is a murine host according to this invention that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference.

Human antibodies may also be produced according to various other techniques, such as by using, for immunization, other transgenic animals that have been engineered to express a human antibody repertoire (Jakobovitz et Nature 362 (1993) 255), or by selection of antibody repertoires using phage display methods. Such techniques are known to the skilled person and can be implemented starting from monoclonal antibodies as disclosed in the present application.

The antibodies of the present invention, preferably a 31C3, 29H3, 23C8, 28F11 or 34A3-like antibody, may also be derivatized to "chimeric" antibodies (immunoglobulins) in which a portion of the heavy/light chain(s) is identical with or homologous to corresponding sequences in the original antibody, while the remainder of the chain (s) is identical with or homologous to corresponding sequences in antibodies derived from another species or belonging to another antibody class or subclass, as well as fragments of such antibodies, so long as they exhibit the desired biological activity and binding specificity (Cabilly et al., supra; Morrison et al., Proc. Natl. Acad. Sci. U.S.A., pp. 6851 (1984)).

While the present antibodies have the ability to bind TLR3 and optionally further inhibit TLR3 signaling, they can also be used for other purposes such as conjugation to a toxin is useful for targeted killing cells expressing TLR3 polypeptides, e.g. certain tumor cells such as melanomas or those of the breast, lung, esophagus, stomach, larynx, kidney, or cervix, or potentially virally infected cells or cells involved in inflammation. In such embodiments, typically a sample is obtained (e.g. a biopsy for tumors) will be performed initially to assess whether the cells (e.g. tumor cells, infected cells, cells involved in inflammation, etc.) express TLR3, e.g., using the detection methods described herein. If TLR3 is indeed detected on the surface of the tumor cells, then, cytotoxic antibodies can be administered. The cytotoxic antibody is then internalized by the cell and the toxin is released inside of the cell, selectively killing that cell. Such antibodies will therefore be used in methods of treating of cancers and tumors, include but not limited to biliary tract cancer; brain cancer; breast cancer; cervical cancer; choriocarcinoma;

colon cancer; endometrial cancer; esophageal cancer; gastric (stomach) cancer; intraepithelial neoplasms; leukemias; lymphomas; liver cancer; lung cancer (e.g., small cell and non-small cell); melanoma; neuroblastomas; oral cancer; ovarian cancer; pancreatic cancer; prostate cancer; rectal cancer; renal (kidney) cancer; sarcomas; skin cancer; testicular cancer; thyroid cancer; as well as other carcinomas and sarcomas. Cancers can be primary or metastatic.

One effective approach for enhancing the anti-tumor-potency of antibodies involves linking cytotoxic drugs or toxins to mAbs that are capable of being internalized by a target cell. These agents are termed antibody-drug conjugates (ADCs) and immunotoxins, respectively. Upon administration to a patient, ADCs and immunotoxins bind to target cells via their antibody portions and become internalized, allowing the drugs or toxins to exert their effect. See, for example, U.S. Patent Appl. Publ. Nos. US2005/0180972 A1, US2005/0123536 A1. See also, for example, Hamblett et al., Clin Canc Res, 10:7063-7070, Oct. 15, 1999, Law et al., Clin Canc Res, 10:7842-7851, Dec. 1, 2004, Francisco et al., Neoplasia, 102 (4):1458-1465, Aug. 15, 2003, Russell et al., Clin Canc Res, 11:843-852, Jan. 15, 2005, Doronina et al., Nat Biotech, 21(7):778-784, July 2003, all of which are hereby incorporated by reference herein in their entirety.

Cytotoxic antibodies can be prepared using described techniques (Carter et al, Cancer Journal, Volume 14, Number 3, May/June 2008, or Ravi et al, Accounts of Chemical Research 98-107 January 2008 Vol. 41, No. 1).

Preferred toxic or cytotoxic peptides or small molecules include any compound that can slow down, halt, or reverse the proliferation of cells, decrease their activity in any detectable way, or directly or indirectly kill them. Preferably, toxic or cytotoxic compounds work by directly killing the cells, by provoking ADCC or otherwise. As used herein, a toxic peptide can include any peptide, polypeptide, or derivative of such, including peptide- or polypeptide-derivatives with unnatural amino acids or modified linkages. A toxic small molecule can include any toxic compound or element, preferably with a size of less than 10 kD, 5 kD, 1 kD, 750 D, 600 D, 500 D, 400 D, 300 D, or smaller.

Conjugation to a detectable moiety is useful, inter alia, when an antibody of the invention is used for diagnostic purposes. Such purposes include, but are not limited to, assaying biological samples, e.g., a blood sample or tissue biopsy, for the presence of TLR3-expressing cells, and detecting the presence, level, or activity of TLR3-expressing cells in an individual. Such assay and detection methods can be used in the diagnostic/therapeutic methods of the invention, e.g., involving detecting TLR3 expression in cells of a patient and if the patient's cells are determined to express TLR3, subsequently administering a TLR3 modulating antibody of the invention.

In certain embodiments, the present antibodies are used to purify TLR3-expressing cells from a biological sample. Biological samples can be obtained from a patient, e.g. for diagnostic or ex vivo therapeutic purposes, or from individuals or non-human primates to obtain a source of such cells for research purposes.

In one such embodiment, labeled antibodies of the invention can be used in FACS sorting to purify or isolate TLR3-expressing cells from a biological sample. Alternatively, in some embodiments conjugation of an antibody of this invention to a solid support can be useful as a tool for affinity purification of cells bearing a TLR3 receptor on their cell surface from a biological sample, such as a blood sample or cells from a tissue biopsy from an individual. This method of purification is another alternate embodiment of the present invention, as is the resulting purified population of cells.

Regardless of the method used to isolate or purify the TLR3-expressing cells, the ability to do so is useful for numerous purposes, e.g. to diagnose a TLR3-associated disorder by assessing the number or activity of TLR3-expressing cells, e.g., prior to administration of anti-TLR3 antibodies as described herein. Further, purified TLR3-expressing cells are useful in a research context, e.g., to better characterize the cells and their various properties and behaviors, as well as to identify compounds or methods that can be used to modulate their behavior, activity, survival, or proliferation.

Compositions and Uses in Therapy, Diagnostics and Prognostics

As demonstrated herein, the antibodies of the invention are particularly effective at modulating the activity of TLR3-expressing cells comprising the polypeptides and, consequently, the activity or behavior of the cells expressing the polypeptides, e.g., TLR3-expressing immune cells, DC, myeloid DC, etc. In certain embodiments, the antibodies inhibit TLR3, e.g., by blocking TLR3 signaling, optionally without blocking the interaction of an antigen or ligand such as dsRNA to the receptor, thereby inhibiting the proliferation or activation of the cells. The composition further comprises a pharmaceutically acceptable carrier. Such compositions are also referred to as "antibody compositions" of the invention. In one embodiment, antibody compositions of this invention comprise an antibody disclosed in the antibody embodiments above. The antibody 31C3, 29H3, 23C8, 28F11 or 34A3 is included within the scope of antibodies that may be present in the antibody compositions of this invention.

The invention further provides a method of modulating TLR3-expressing cell activity in a patient in need thereof, comprising the step of administering to said patient a composition according to the invention. In one embodiment, the TLR3-expressing cell activity is inhibited, wherein the patient has a disease or disorder wherein such inhibition may promote, enhance, and/or induce a therapeutic effect (or promotes, enhances, and/or induces such an effect in at least a substantial proportion of patients with the disease or disorder and substantially similar characteristics as the patient, as may determined by, e.g., clinical trials).

In other embodiments, the method may comprise the additional step of administering to said patient an appropriate additional therapeutic agent useful in treatment or prevention of the disease from which the patient suffers or is susceptible to; examples of such agents include an immunomodulatory agent, a hormonal agent, an anti-inflammation drug, a steroid, an immune system suppressor, a corticosteroid, an antibiotic, an anti-viral or an adjunct compound. Such additional agents can be administered to a patient as a single dosage form together with said antibody, or as a separate dosage form. The dosage of the antibody (or antibody and the dosage of the additional therapeutic agent collectively) are sufficient to detectably induce, promote, and/or enhance a therapeutic response in the patient. Where administered separately, the antibody, fragment, or derivative and the additional therapeutic agent are desirably administered under conditions (e.g., with respect to timing, number of doses, etc.) that result in a detectable combined therapeutic benefit to the patient.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. The antibodies of this invention may be employed in a method of modulating, e.g inhibiting, the activity of TLR3-expressing cells in a patient. This method comprises the step of contacting said composition with said patient. Such method will be useful for both prophylaxis and therapeutic purposes.

For use in administration to a patient, the composition will be formulated for administration to the patient. The compositions of the present invention may be administered orally, parenterally, by inhalation spray, topically, rectally, nasally, buccally, vaginally or via an implanted reservoir. The used herein includes subcutaneous, intravenous, intramuscular, intra-articular, intra-synovial, intrasternal, intrathecal, intrahepatic, intralesional and intracranial injection or infusion techniques.

Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include, e.g., lactose. When aqueous suspensions are required for oral use, the active ingredient is combined with emulsifying and suspending agents. If desired, certain sweetening, flavoring or coloring agents may also be added.

Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Topical application for the lower intestinal tract can be effected in a rectal suppository formulation (see above) or in a suitable enema formulation. Patches may also be used.

The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Several monoclonal antibodies have been shown to be efficient in clinical situations, such as Rituxan Herceptin (Trastuzumab) or Xolair (Omalizumab), and similar administration regimens (i.e., formulations and/or doses and/or administration protocols) may be used with the antibodies of this invention. Schedules and dosages for administration of the antibody in the pharmaceutical compositions of the present invention can be determined in accordance with known methods for these products, for example using the manufacturers' instructions. For example, an antibody present in a pharmaceutical composition of this invention can be supplied at a concentration of 10 mg/mL in either 100 mg (10 mL) or 500 mg (50 mL) single-use vials. The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. An exemplary suitable dosage range for an antibody in a pharmaceutical composition of this invention may between about 1 mg/m$^2$ and 500 mg/m$^2$. However, it will be appreciated that these schedules are exemplary and that an optimal schedule and regimen can be adapted taking into account the affinity and tolerability of the particular antibody in the pharmaceutical composition that must be determined in clinical trials.

According to another embodiment, the antibody compositions of this invention may further comprise another therapeutic agent, including agents normally utilized for the particular therapeutic purpose for which the antibody is being administered. The additional therapeutic agent will normally be present in the composition in amounts typically used for that agent in a monotherapy for the particular disease or condition being treated. Such therapeutic agents include, but are not limited to anti-inflammation agents, steroids, immune system suppressors, antibiotics, antivirals and other antibodies and fragments thereof.

In another embodiment, two or more antibodies of this invention having different cross-reactivities, e.g. antibodies that specifically bind to distinct epitopes within the TLR3 polypeptide, are combined in a single composition so as to target as many distinct TLR3 gene products as possible, e.g. to account for diversity in the polypeptides within an individual or in different patients, and to do so as efficaciously as possible. In addition, an antibody composition of this invention may comprise multiple antibodies that recognize a single TLR3 epitope. Such combinations would again provide wider utility in a therapeutic setting.

The invention also provides a method of modulating TLR3-expressing cell activity in a patient in need thereof, comprising the step of administering a composition according to this invention to said patient. The method is more specifically directed at decreasing TLR3 cell activity in patients having a disease in which decreased TLR3 cell activity is beneficial (e.g., autoimmune diseases, inflammatory diseases, infectious disease, viral infection), or which is caused or characterized by excessive TLR3 cell activity.

Diseases and conditions in which the present methods can be used include all diseases where modulating TLR3 can be beneficial, including for example diseases mediated or exacerbated partially or totally by TLR3 signaling or by cytokines produced upon said TLR3 signaling. In particular, where antibodies that inhibit TLR3 signaling are used, such disorders include any disorders mediated or exacerbated partially or totally by TLR3 signaling or by cytokines produced upon said TLR3 signaling, including inter alia immune disorders such as inflammatory diseases and autoimmune diseases. More specifically, the methods of the present invention are utilized for the treatment of a variety of immune disorders and other diseases including, but not limited to autoimmunity, inflammation, allergy, asthma, infections (e.g. chronic infection, viral infection) and sepsis. Examples of diseases which can be treated with the antibodies that inhibit TLR3 signaling include, but are not limited to arthritis, systemic lupus erythematosus, sepsis, asthma, osteoporosis, autoimmunity to central nervous system antigens, autoimmune diabetes, inflammatory bowel disease, autoimmune carditis, autoimmune hepatitis.

Other immune disorders treatable using the antibodies that inhibit TLR3 signaling according to the invention include, inter alia, autoimmune disorders and inflammatory disorders, including, but not limited to, Crohn's disease, Celiac disease, ulcerative colitis, irritable bowel syndrome, acute disseminated encephalomyelitis (ADEM), Addison's disease, antiphospholipid antibody syndrome (APS), aplastic anemia, autoimmune hepatitis, Diabetes mellitus, Goodpasture's syndrome, Graves' disease, Guillain-Barre syndrome (GBS), Hashimoto's disease, lupus erythematosus, demyelinating conditions, Multiple sclerosis, Myasthenia gravis, opsoclonus myoclonus syndrome (OMS), optic neuritis, Ord's thyroiditis, pemphigus, cirrhosis, psoriasis, rheumatoid arthritis, Reiter's syndrome, Takayasu's arteritis, temporal arteritis, warm autoimmune hemolytic anemia, Wegener's granulomatosis, appendicitis, arteritis, arthritis, blepharitis, bronchiolitis, bronchitis, bursitis, cervicitis, cholangitis, cholecystitis, chorioamnionitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, gingivitis, hepatitis, hidradenitis suppurativa, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, and vulvitis.

The present antibodies can be included in kits. The kits may optionally further contain any number of antibodies and/or other compounds, e.g., 1, 2, 3, 4, or any other number of therapeutic antibodies and/or compounds. It will be appreciated that this description of the contents of the kits is not limiting in any way. For example, the kit may contain other types of therapeutic compounds. Preferably, the kits also include instructions for using the antibodies, e.g., detailing the herein-described methods.

Further aspects and advantages of this invention will be disclosed in the following experimental section, which should be regarded as illustrative and not limiting the scope of this application.

EXAMPLES

Materials and Methods

Interferon-alpha (IntronA™) was purchased from Schering Plough Corp. Tumor Cell lines: A375 malignant melanoma tumor cell lines (CRL-1619) are purchased from ATCC. Antibodies (antigen, supplier, reference): Anti-TLR3 antibody pAb, R&D Systems, ref. AF1487. Instrumentation: FACSCalibur™ flow cytometer (BD Biosciences).
Inhibition with Lentivirus shRNA A lentivirus construction was made and produced by Vectalys (Toulouse, France), encoding short hairpin RNA (shRNA) targeting control human TLR3. Tumor cells were infected with lentivirus preparation and further selected with puromycin to get stable shTLR3 A375 tumor cells.
Surface Plasmon Resonance (SPR)

(a) General Biacore T100 methods. SPR measurements were performed on a Biacore T100 apparatus (Biacore GE Healthcare) at 25° C. In all Biacore experiments HBS-EP+ buffer (Biacore GE Healthcare) or 10 mM sodium acetate pH 5.6, 150 mM NaCl, 0.05% P20 served as running buffer and sensorgrams were analyzed with Biaevaluation 4.1 and Biacore T100 Evaluation software. Recombinant human TLR3 was purchased from R&D Systems.

(b) Protein immobilization. Recombinant TLR3 protein was immobilized covalently to carboxyl groups in the dextran layer of a Biacore Series 5 Sensor Chip CM5 (chip). The chip surface was activated with EDC/NHS (0.2M N-ethyl-N'-(3-dimethylaminopropyl) carbodiimidehydrochloride, 0.05M N-hydroxysuccinimide (Biacore GE Healthcare)). Proteins were diluted to 10 µg/ml in coupling buffer (10 mM sodium acetate, pH 5.6) and injected until the appropriate immobilization level was reached (i.e. approximately 2000 RU for binding experiments and 600 RU for affinity experiments). Deactivation of the remaining activated groups was performed using 100 mM ethanolamine pH 8 (Biacore GE Healthcare).

(c) Antibody binding analysis was run using HBS-EP+ (neutral pH). Antibodies at a concentration of 10 µg/ml were injected for 2 min at a constant flow rate of 10 µl/min over the immobilized proteins and allowed to dissociate for 3 min before regeneration by a ten second injection of 10 mM NaOH, 500 mM NaCl regeneration buffer. Blank correction was performed on line by co-injecting the soluble antibodies onto the reference dextran flow cell.

(d) Competition assay in acidic buffer (pH 5.6). Flow rate was set to 10 µl/min, the first antibody at a concentration of 50 µg/ml (or polyAU at 100 µg/ml) was injected for 2 min, 3 times successively in order to saturate the rhTLR3 surface. The second antibody was then injected for 2 min also at 50 µg/ml and allowed to dissociate for 3 min before regeneration by a 15 second injection of 10 mM NaOH, 500 mM NaCl regeneration buffer. Blank correction was also performed on line and the curve using the saturating antibody (or neucleic acid) followed by an injection of buffer subtracted to remove the signal due to the dissociation of the first complex. The resulting signal was compared to that obtained by the injection of the second antibody directly onto the rhTLR3 surface.
Luciferase Reporter Assay.

A reporter gene assay using as promoter ISRE (IFN-stimulated response element) and as reporter gene and protein luciferase was set up. A 293T cell line (ATCC, #CRL-1573) was stably transfected with pISRE-luc plasmid (#219089—Stratagene), further selected as inducing optimal response to IFN-alpha stimulation and referred to as control 293T-ISRE. This cell line was further stably transfected with different plasmids pUNO-hTLR3 plasmid (#puno-htlr3—InVivogen) and referred to as 293T-TLR3-ISRE. On day 0, cells are seeded at $4\times10^5$ cells/mL in complete culture medium in 96-well culture plate (100 μl/well). Cells are first incubated at 37° C. for 20 hours, then 50 μL of medium are discarded and cells are activated with 100 μL/well final of increasing amounts of polyAU together with various concentrations of anti-TLR3 antibodies. Cells incubated with fresh medium will be used as background luciferase activity. Cells are incubated at 37° C. for 6 hours. 100 μL of freshly thawed Steady Glo (Promega) are added to each well, plates were incubated 10 min at RT in the dark and the light emitted in each well is quantified as Count Per Second (CPS) on a gamma-counter (TopCount) apparatus.

Example 1

Generation of TLR3-Specific Monoclonal Antibodies

Immunization #1
Primary Screen.

To obtain anti-TLR3 antibodies, Balb/c mice were immunized with a recombinant human His-tagged TLR3 extracellular domain recombinant protein (R&D systems, #1487-TR-050). Mice received one primo-immunisation with an emulsion of 50 μg TLR3 protein and Complete Freund Adjuvant, intraperitoneally, a 2nd immunization with an emulsion of 50 μg TLR3 protein and Incomplete Freund Adjuvant, intraperitoneally, and three boosts with 10 μg TLR3 protein, intravenously. Immune spleen cells were fused with X63.Ag8.653 immortalized B cells, and cultured in the presence of irradiated spleen cells. 40 culture plates were obtained and evaluated in a first screen for TLR3 binding using an ELISA developed for detection of binding to TLR3. Briefly, His-tagged recombinant TLR3 protein (R&D systems, #1487-TR-050) was coated on Ni-NTA 96-wells plates (Qiagen). Supernatant (SN) from hybridoma culture plates and incubated in TLR3-plates, and the presence of TLR3 binding Ig was revealed with goat anti-mouse F(ab) IgG-HRP. Positive supernatants were selected and tested for lack of binding to TLR4. Briefly, His-tagged rec TLR4 protein (R&D systems, #3146-TR-050) were coated on Ni-NTA 96-wells plates (Qiagen). SN from hybridoma culture plates were incubated in TLR4-plates, and the presence of TLR4 binding Ig was revealed with goat anti-mouse F(ab) IgG-HRP. TLR4 was chosen as a $2^{nd}$ screen in order to discriminate among wells selected in the $1^{st}$ screen, where anti-His specific antibody from TLR3 specific antibody were used. Secondly, given the homology between TLR3 and other members of TLR family, the initial assessment in demonstrated that at least one commercially available monoclonal antibody (mAb) indicated on its packaging as specific for TLR3 protein nevertheless recognized paraffin-embedded 293T cells stably transfected with TLR4.

Secondary Screen; Selection of Hybridomas of Interest.

168 supernatants were retained and tested in a further screen in a Biacore assay using rec TLR3 chips, followed by various assays formats based on binding to human TLR3-expressing 293T cells. A 293T cell line (ATCC, #CRL-1573), stably transfected with pISRE-luc plasmid (#219089—Stratagene), was further selected as inducing optimal response to IFN-alpha stimulation and referred to as control 293T cells. This cell line was further stably transfected with pUNO-hTLR3 plasmid (#puno-htlr3—InVivogen), or pUNO-hTLR4 plasmid (#puno-tlr4—InVivogen) and referred to respectively as 293T-TLR3 and 293T-TLR4. Supernatants were screened in a FACS based screen for binding to 293T-TLR3 cells with no binding to 293T control cells, and in parallel in an IHC screen for binding to 293T-TLR3 cells as a frozen cell pellet, with no binding to 293T-TLR4 cells. Wells selected in the IHC screen for binding to 293T-TLR3 cells as a frozen cell pellet were also further tested in an IHC screen for binding to 293T-TLR3 cells as a paraffin embedded cell pellet. Briefly, for FACS screening, the presence of reacting antibodies in supernanants were revealed by Goat anti-mouse polyconal antibody (pAb) labeled with biotin, streptavidin labeled with PE. For IHC screening, presence of reacting antibodies (Abs) in supernanants were revealed by donkey anti-mouse pAb labeled with biotin (#715-065-150, Jackson Immunoresearch Laboratories), streptavidin labeled with peroxydase (#E2886, SIGMA) and revealed with DAB (#SK-4105, Vector Laboratories).

Cloning of Hybridomas of Potential Interest.

42 potentially interesting hybridomas selected from the initial screening were cloned by limiting dilution techniques in 96-wells plates, and 304 subclones were tested in a series of screens as follows. The 304 subclones were first evaluated in a screen for TLR3 binding using the same ELISA developed for detection of binding to TLR3, and positive supernatants were selected and tested for lack of binding to TLR4 in ELISA assay, yielding 228 clones which were selective for TLR3. All supernatants yielding a ratio above 10 for DO obtained in TLR3 ELISA to DO obtained in TLR4 ELISA were selected as specific for TLR3. Among them were supernatants from well C3 of plate 31 (31C3), well H3 of plate 29 (29H3), well E7 of plate 23 (23E7), well C8 of plate 23 (23C8) and well F11 of plate 28 (28F11). 31C3, 29H3, 23C8 and 28F11 are of IgG1 isotype.

Among the 304 clones, 63 clones, selected as issuing from preclones tested positive in frozen IHC, were also tested in a frozen IHC screen for binding to 293T-TLR3 cells as a frozen cell pellet, with no binding to 293T-TLR4 cells, yielding 31 positive clones in frozen IHC.

Among 71 clones positive in FACS staining and the 31 clones positives in frozen IHC, 41 clones were selected for cryopreservation from the 304 initial clones.

Immunization #2
Primary Screen.

A further series of immunization were carried out in order to generate different antibodies. Using an experimental setup similar to that of the first immunization series, Balb/c mice were immunized, immune spleen cells were fused and cultured in the presence of irradiated spleen cells. Culture plates were obtained and evaluated in a first screen for TLR3 binding using an ELISA developed for detection of binding to TLR3. 263 clones out of 2840 were selected for the secondary screen.

Secondary Screen; Selection of Hybridomas of Interest.

263 supernatants were retained and tested in a further screen in an inhibition test on 293T-TLR3 cells. Clones having an inhibitory effect superior to 95% were selected. Among them were supernatants from well A3 of plate 34 (34A3).

Example 2

TLR3 Modulation

Myeloid DC (MdDC) were obtained from PBMC by isolating PBMC from normal healthy human donors. Monocytes were purified from PBMC using positive selection with human CD14 microbeads (Miltenyi Biotech) following general instructions. Monocytes were further derived into DC (MdDC) by 5-6 days incubation in human GM-CSF (Leucomax, SP) and human IL-4 (R&D Systems) at respectively 200 ng/ml and 20 ng/ml.

The resulting MdDC were then seeded at $10^6$ cells/ml, in duplicate, in flat bottom 96-well plates. Cells were activated for 20 hours in a final volume of 200 µl, together with the anti-TLR3 antibodies at the indicated concentrations. Increasing amounts of polyAU (30, 100, 300 and 900 µg/ml) were added to the wells to obtain a dose effect read-out.

Supernatants were collected after 20 h of stimulation, frozen at −20° C., and further assayed for IL-6 and IP-10 using Enzyme-linked immunosorbent assay. Cells were then harvested, stained for activation markers CD86 (with a.huCD86 mouse, IgG1, FITC, BD Biosciences, ref 555657), with detection using FACSCanto™ flow cytometer (BD Biosciences).

Figure 1A:
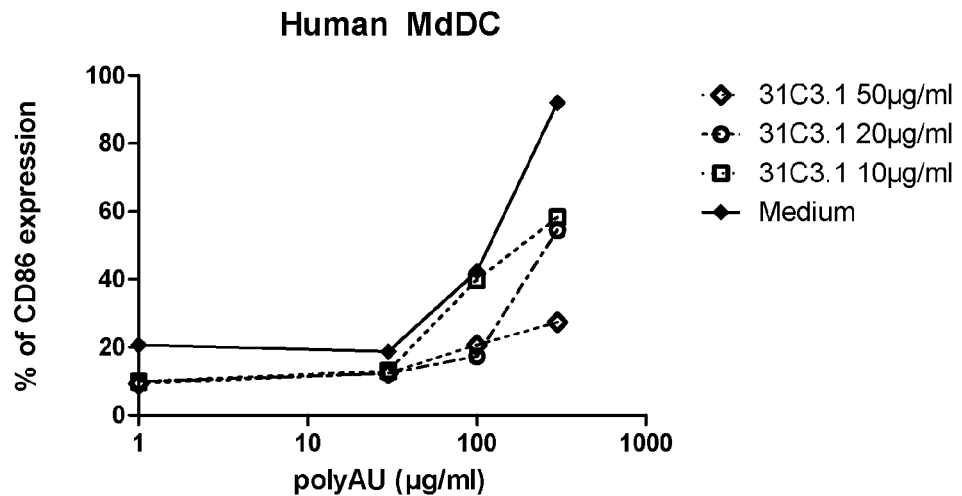
FIG. 1A: level of CD86 expression.
Figure 1B:
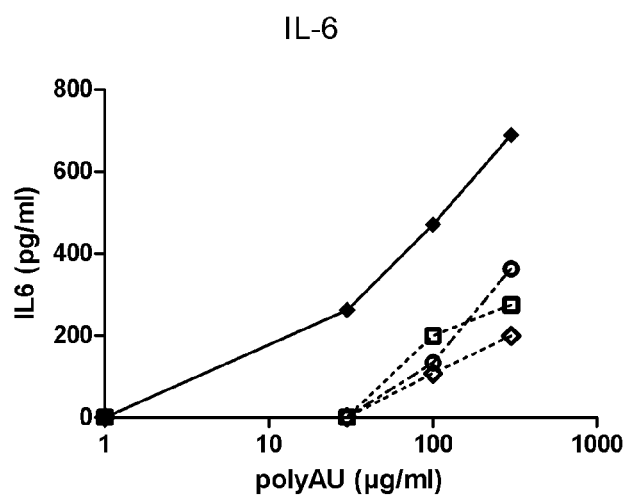
FIG. 1B: IL-6 secretion.
Figure 1C:
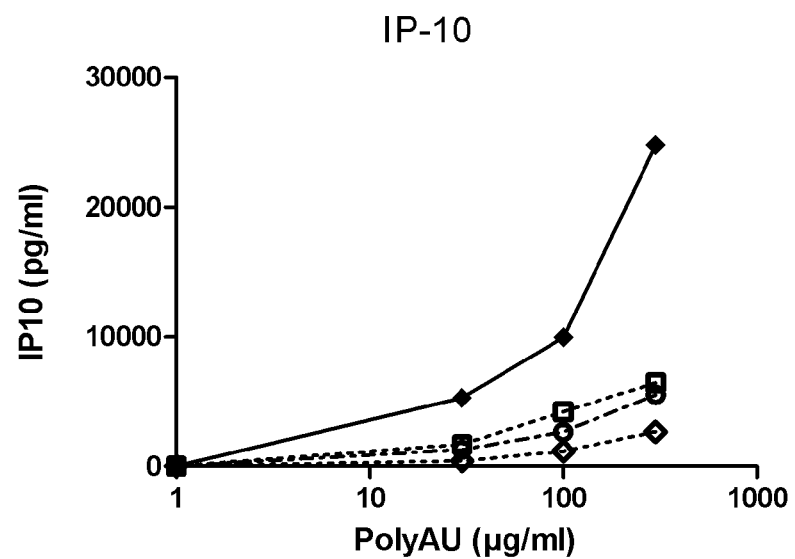
FIG. 1C: IP-10 secretion. All figures show that compared to control, the antibody 31C3 inhibits TLR3 ligand-induced response.
Figure 2A:
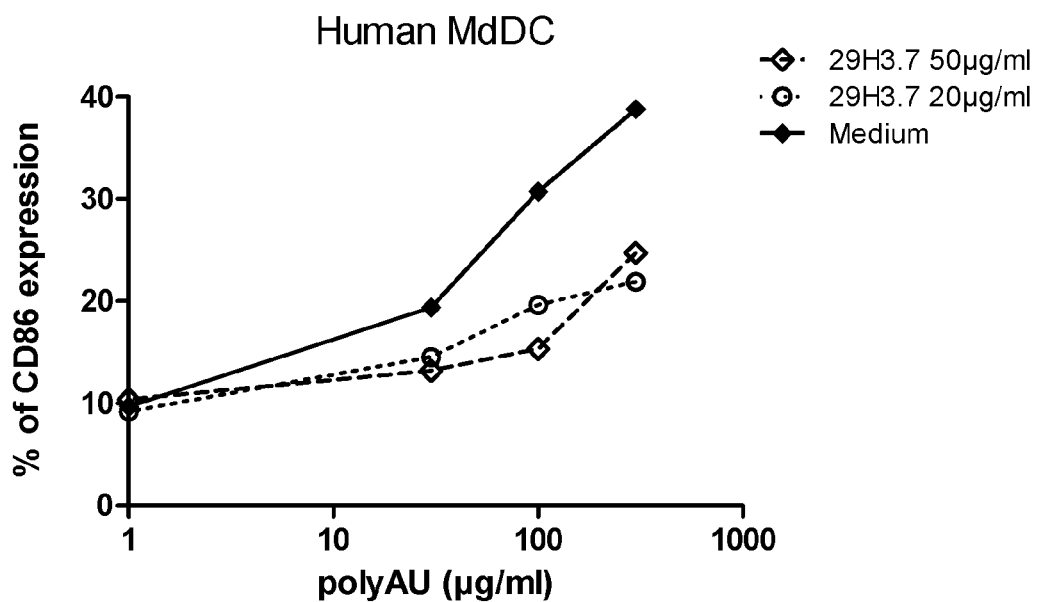
FIG. 2A: level of CD86 expression.
Figure 2B:
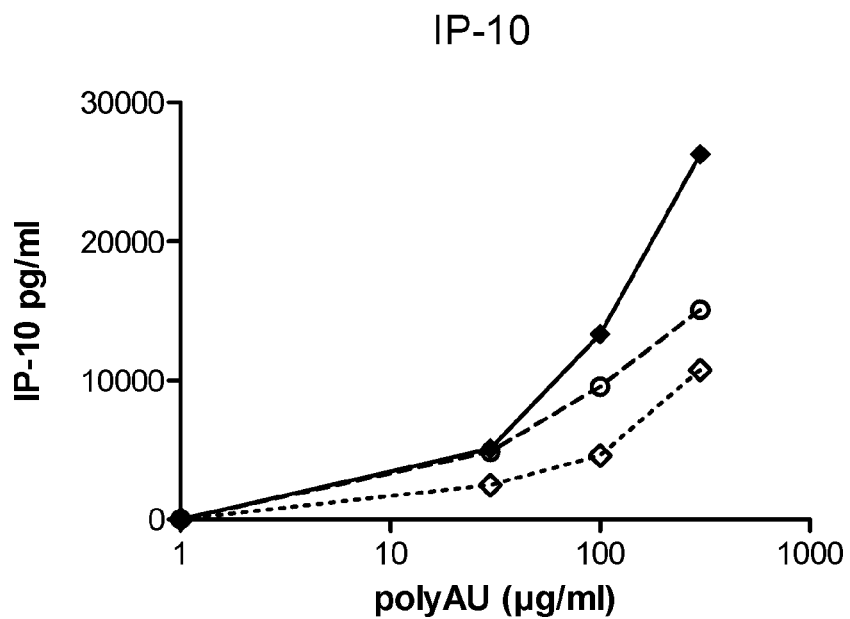
FIG. 2B: IP-10 secretion. All figures show that compared to control, the antibody 29H3 inhibits the TLR3 ligand-induced response.

FIGS. 1 and 2 illustrate the inhibitory properties of antibodies 31C3 and 29H3 (both are of IgG1 isotype) in terms of CD86 cellular activation and IL-6, IP-10 secretion. The anti-TLR3 antibodies 31C3.1 and 29H3.7 antagonize, in vitro, TLR3-mediated myeloid DC activation, moreover, these antibodies effectively downregulated TLR3-mediated CD83/CD86 expression and abrogated TLR3-mediated cytokine/chemokine secretion, in particular IP-10 and IL-6.

Figure 3A:
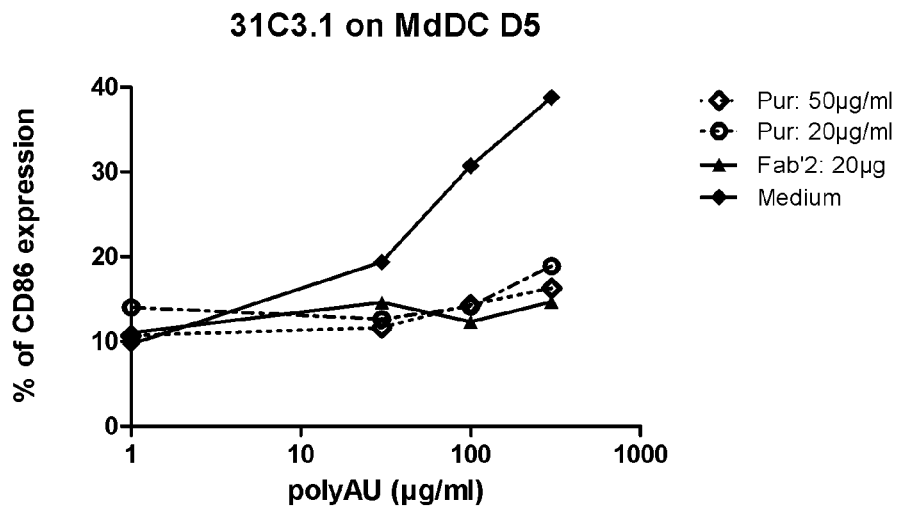
FIG. 3A: level of CD86 expression.
Figure 3B:
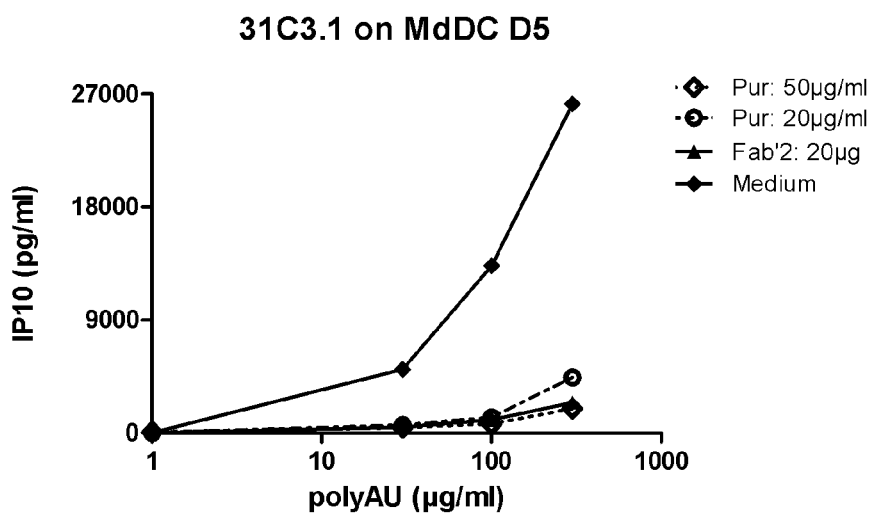
FIG. 3B: IP-10 secretion. The figures show that F(ab)'2 fragments of antibody 31C3 inhibit TLR3 ligand-induced response as well as purified whole 31C3 antibodies.
Figure 4A:
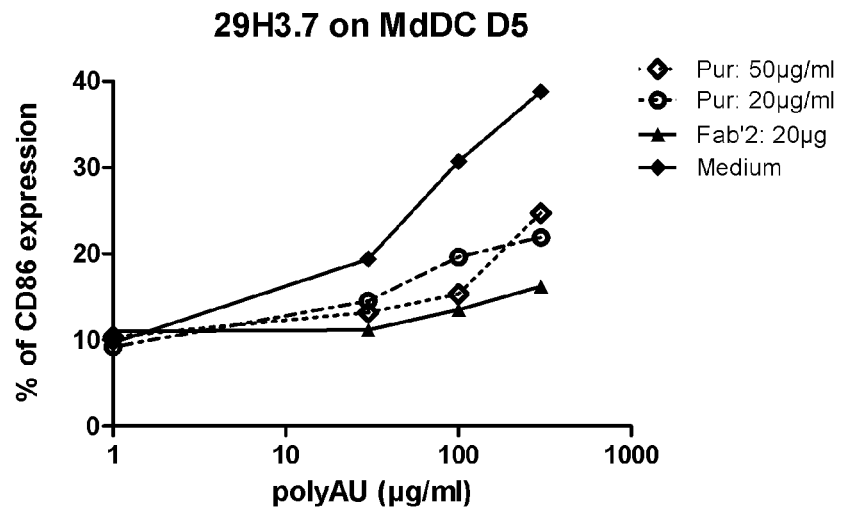
FIG. 4A: level of CD86 expression.
Figure 4B:
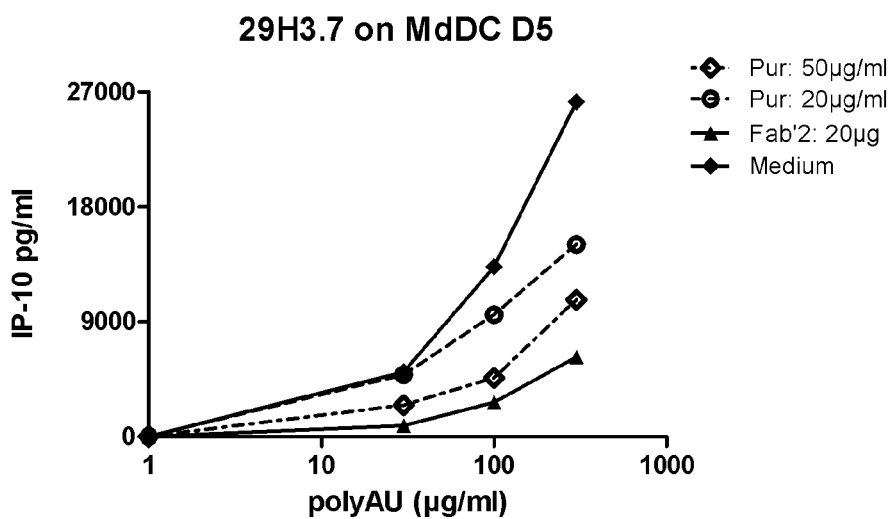
FIG. 4B: IP-10 secretion. The figures show that F(ab)'2 fragments of antibody 29H3 inhibit TLR3 ligand-induced response as well as purified whole 29H3 antibodies.

F(ab)'2 fragments were generated from antibodies 31C3.1 and 29H3.7 by papain cleavage and purification by ion-exchange chromatography on MonoQ 5/50 GL, analyzed by SDS-PAGE, and tested for inhibition in terms of CD86 cellular activation and cytokine secretion. F(ab)'2 fragments of both antibodies 31C3.1 and 29H3.7 effectively downregulated TLR3-mediated CD83/CD86 expression and abrogated TLR3-mediated cytokine/chemokine secretion, to a similar extent as full length antibodies. FIG. 3 shows the results for antibody 31C3, where F(ab)'2 fragments of antibody 31C3 and whole 31C3 IgG abrogate TLR3-mediated CD86 expression and IP-10 secretion to a similar extend; FIG. 4 shows the same for F(ab)' 2 fragments of antibody 29H3.

Figure 14A:
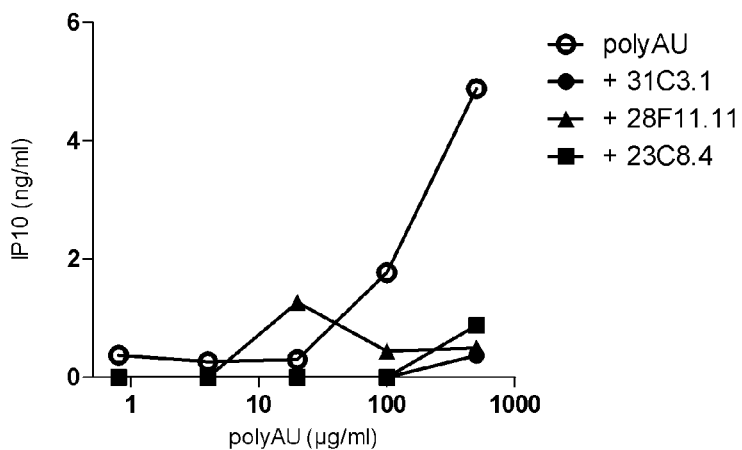
FIG. 14A: IP-10 secretion.
Figure 14B:
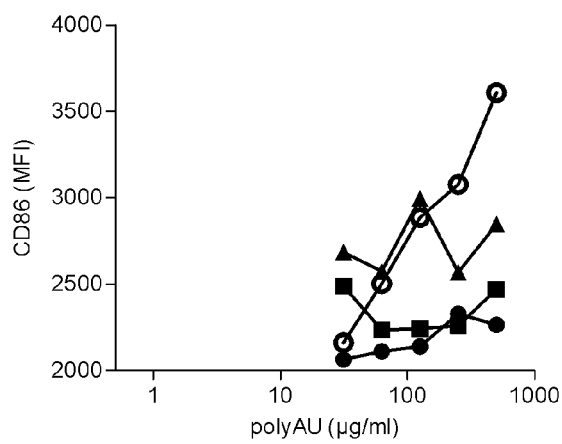
FIG. 14B: level of CD86 expression. All figures show that compared to control, the antibody 31C3

In a similar experiment, the ability of 28F11 and 23C8 antibodies to inhibit TLR3 signaling were assessed, compared to antibody 31C3. The antibodies were tested at a concentration of 50 µg/ml in the presence of an increasing dose of polyAU. The results are represented in FIGS. 14A and 14B, underlining the inhibitory properties of the antibodies according to the invention.

Figure 19B:
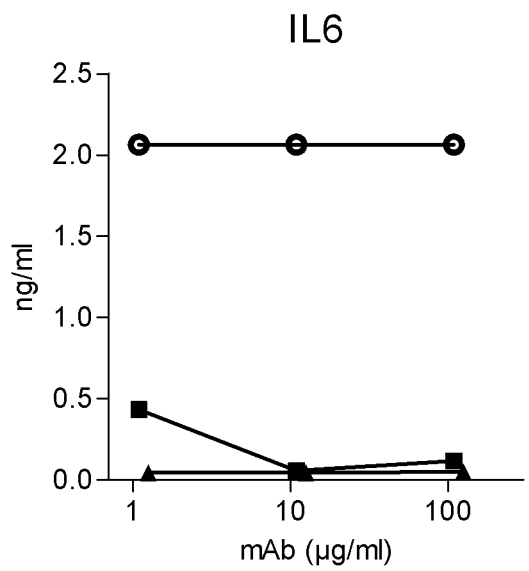

Antibody 34A3 has also been tested in a similar setting. This time, the cells (MdDC) are stimulated with a fixed dose of polyAU (300 µg/ml) and increasing doses of the antibody is added to the medium. FIGS. 19A and 19B illustrate the results for antibody 34A3, in comparison with 31C3 in terms of IL-6 and IP-10 secretion.

Example 3

Bivalent Affinity

Figure 5:
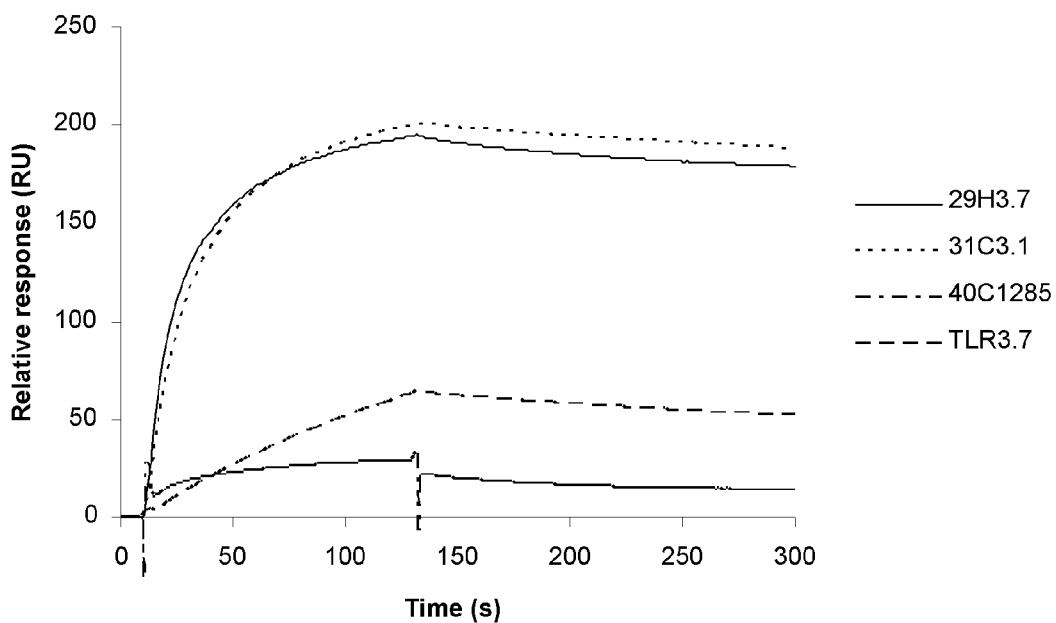
FIG. 5 shows a comparison of binding affinity that the antibodies according to the present invention have a stronger binding for the TLR3 chip than commercially available antibodies.

Binding properties of the antibodies 29H3.7, 23E7.3, 31C3.1 and commercially available antibodies TLR3.7 (eBiosciences) and 40C1285 (Abcam) were compared using the methods described for SPR, item c). FIG. 5 shows that the binding affinity for TLR3 is significantly better in the case of 29H3.7 and 31C3.1 than in the case of commercially available antibodies.

Binding to TLR3 was determined at neutral (pH 7.2) and acid (pH 5.6) conditions, and K(D) values were calculated. The results (mean of 2 or 3 experiments) are shown in Table 1. At neutral pH, 23E7, 29H3.7 and 31C3.1 all showed strong and similar bivalent affinity ($K_D$) for recombinant human TLR3 better than 100 picomolar (around 50 picomolar). Antibody TLR3.7 (eBiosciences) in comparison showed a significantly lower binding affinity. At acid pH, however, 23E7 lost considerable binding affinity and its $K_D$ was at about 4 nanomolar. The affinity of 31C3, 23C8, 28F11 and 34A3 were measured in the same conditions in a separate assay, the results are represented in Table 1 and in FIG. 15. These results indicate that the antibodies according to the invention have a high affinity, especially at acidic pH.

TABLE 1

| Antibody | Mean $K_D$ (M) at pH 7.2 | Mean $K_D$ (M) at pH 5.6 |
| --- | --- | --- |
| 23E7.3 | $3.51 * 10^{-11}$ | $4.32 * 10^{-9}$ |
| 29H3.7 | $4.74 * 10^{-11}$ | $1.10 * 10^{-11}$ |
| 31C3.1 | $5.05 * 10^{-11}$ | $6.14 * 10^{-11}$ |
| TLR3.7 | $4.5 * 10^{-8}$ | $9 * 10^{-9}$ |
| 23C8 | $1.38 * 10^{-10}$ | $1.03 * 10^{-11}$ |
| 28F11 | $6.50 * 10^{-10}$ | $3.35 * 10^{-10}$ |
| 34A3 | $3.01 * 10^{-12}$ | $5.17 * 10^{-11}$ |

Example 4

Epitope Mapping

Figure 6:
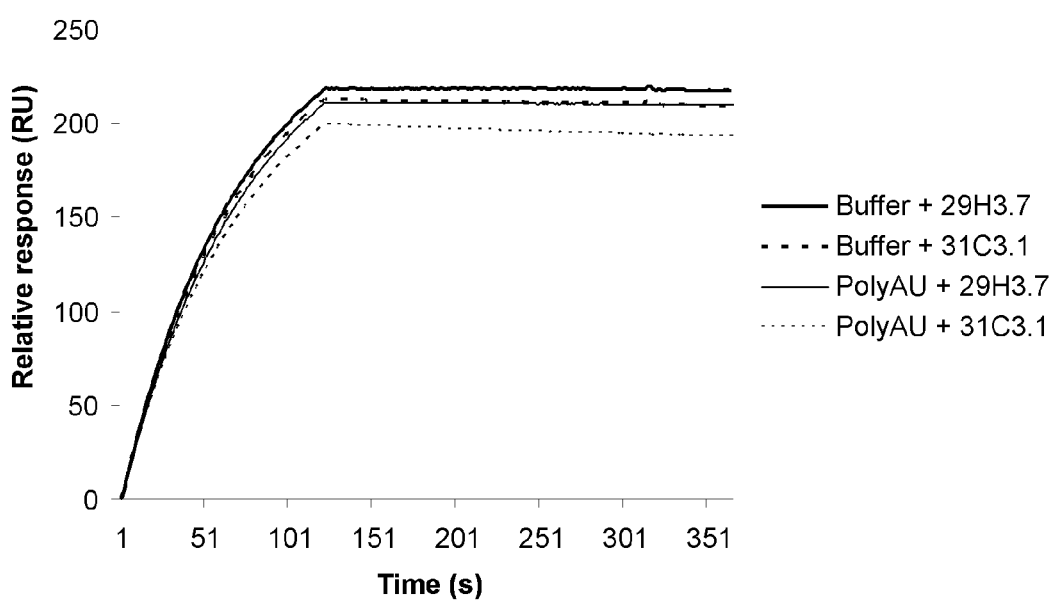
FIG. 6 shows the binding of the antibodies according to the invention on a TLR3 chip in the presence or in the absence of polyAU, a ligand for TLR3 receptors. The figure shows that the binding of the antibodies of the invention do not block dsRNA binding to the TLR3 dsRNA fixation site.
Figure 7:
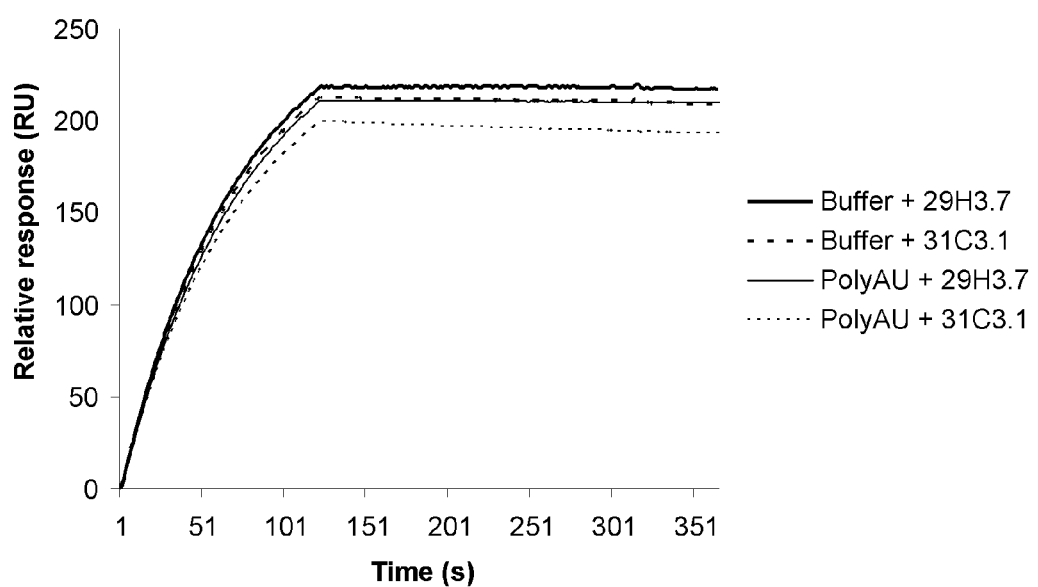
FIG. 7 shows that the presence of 29H3 on the TLR3 chip blocks the binding of 31C3 and vice versa. These results tend to show that both antibodies compete for an overlapping or highly similar epitope.

Epitope mapping at acid pH. Competition assays were conducted according to the methods described for SPR, item d) at pH 5.6. FIG. 6 illustrates that antibodies 29H3.7 and 31C3.1 were able to bind TLR3 without competing with polyAU, similarly, FIGS. 16A and 16B illustrate that antibodies 28F11, 34A3 and 23C8 were able to bind TLR3 without competing with polyAU. 29H3.7, 31C3.1, 28F11, 34A3 and 23C8 are thus able to inhibit dsRNA signaling without competing for the epitope of dsRNA on TLR3. FIG. 7 illustrates the competition between antibodies 29H3.7 and 31C3.1. As the binding to TLR3 by one antibody impairs the binding to TLR3 of the other (about 90% inhibition by one antibody of the other), one can conclude that these two antibodies compete for a similar epitope on TLR3. Similarly, FIGS. 15A and 15B illustrate the competition between antibody 31C3 with antibodies TLR307, 23C3, 28F11 and 29H3. FIG. 15A illustrates binding in the absence of any competing antibody whereas FIG. 15B illustrates the binding level after saturation of the hTLR3 chip with 31C3. The loss in binding level reflects the hindrance caused by the 31C3 antibody, and underlines competition for binding between the tested antibodies. TLR3.7 binding level being not affected by 31C3 competition underlines that the antibodies compete for different epitopes, whereas the decrease in binding level for all of the other antibodies underline that they all compete with 31C3 for a similar epitope.

Epitope mapping at neutral pH. Competition assays were conducted according to the methods described for SPR, at pH 7.2. Antibodies 29H3.7 and 31C3.1 competed with one another for binding to TLR3 since binding by one antibody impaired the binding to TLR3 of the other. Epitope mapping was explored also with commercial antibody TLR3.7 and antibody 23E7.3. Neither of these antibodies competed for binding to TLR3 with either of antibodies 29H3.7 and 31C3. However, antibody TLR3.7 did compete for binding to TLR3 with antibody 23E7.3, indicating that they have overlapping binding sites.

The 34A3 antibody binding affinity was measured either alone on a rhTLR3 chip or in conditions where the rhTLR3 chip was saturated with the 31C3 antibody prior to 34A3 addition. The results are shown in FIG. 17, and provide evidence that the two antibodies compete for binding to hTLR3, thus sharing a common epitopic determinant in view of their overlapping binding sites.

FIG. 8 shows molecular surface maps of the extracellular domains of the human TLR3 protein, generated by computer modeling using SwissPdb Viewer 4.0 (Guex and Peitsch (2007) Electrophoresis 18: 2714-2723) based on data publicly available as data file 1ZIW from the Resource for Studying Biological Macromolecules database from the Protein Data Bank (PDB) project of the European Bioinformatics Institute (Hinxton U.K.). The C-terminal is on the left and the N-terminal on the right in this view, showing the face of TLR3 which is substantially glycosylation free, the other face being extensively masked by carbohydrates (see e.g. Choe et al. (2005) Science 309:581-585). The surface map on the right hand side in FIG. 8 shows the electrostatic potential of the human TLR3 polypeptide at neutral pH, mapped to the molecular surface. The main areas of positive electrostatic potential are indicated with arrows, forming a general region of positive and neutral potential on the glycosylation free face of the C-terminal side. The glycosylation-free face is believed to be accessible for interaction with ligands accessory molecules or TLR3 monomers or other oligomer assemblies, and the region of positive electrostatic potential on the C-terminal side (in the darkest shading, the main positive areas indicated by arrows) is thought to correspond to the dsRNA binding region. These regions are also shown in FIG. 5 of Choe et al. (2005). The map on the left hand side indicates amino acid residues determined by mutation studies to be involved in dsRNA binding, where residues dsRNA binding was inhibited (>80%) by mutation of residues H539, N541, N466, R489, N517 or N540, and where dsRNA binding was inhibited (>80%) by mutation of residues K117, K137 and K139. The model proposed in Choe et al. (2005) is that TLR3 forms a homodimer where the dimerization interface is proximal to the C-terminal region on the glycosylation-free face and that dsRNA binds to only the glycosylation-free face of TLR3, such that two TLR3 monomers could sandwich dsRNA in a complex of two TLR3 monomers and one dsRNA strand. A model involving an oligomeric complex of TLR3 formed by multiple dimers of TLR3 binding to longer dsRNA strands has also been proposed (see e.g. Bell et al. (2006) PNAS USA 103(23): 8792-8797). Ranjith-Kumar et al. (2007) J. Biol. Chem. 282(10): 7668-7677 propose that TLR3 can exist in an oligomerized stage in the absence of ligand, and that dsRNA binding can cause rearrangement in the dimer leading to lateral sliding of the monomers toward each other and adjust to accommodate the dsRNA, and where the resulting conformation change can stimulate the interaction of the TIR domain to induce signaling. One explanation could therefore be that the anti-TLR3 antibodies 31C3, 29H3, 23C8, 28F11 and 34A3 bind TLR3, e.g. on glycosylation-free face, and possibly in an epitope having a negative charge at neutral pH which is therefore not in the region of dsRNA binding to TLR3. The antibodies therefore would not prevent interaction of dsRNA with TLR3, but could inhibit signaling, e.g. by preventing a TLR3 dimer or oligomer that has bound dsRNA from rearranging or adopting the configuration required to bring about interaction of the TIR domains, or by interfering with the proper formation of TLR3 dimers and/or a consequential TLR3-dsRNA ternary complex.

Example 5

Reporter Assay

Figure 9:
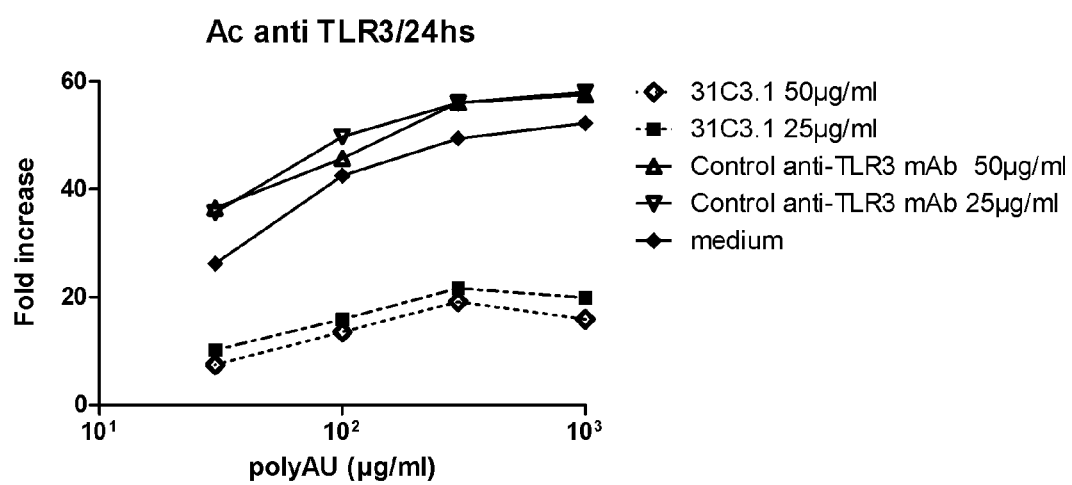
FIG. 9 shows results of an assay for inhibition of TLR3 signaling in a luciferase based reporter gene activity (293T-TLR3-ISRE), where fold increase in luciferase is indicated as a function of polyAU dose. Briefly, dsRNA TLR3 agonists were used to induce TLR3 signaling in the reporter assay in the presence of anti-TLR3 antibody 31C3, and TLR3 signaling was assessed. Antibody 31C3 strongly inhibited TLR3 signaling in a dose dependent fashion, compared to a control anti-TLR3 antibody having no TLR3 inhibiting activity.

Antibodies were tested for inhibition of TLR3 signaling in a luciferase based reporter gene activity (293T-TLR3-ISRE). Engagement of TLR3 receptor using TLR3-agonists such as poly (I:C) has been reported to activate the type-IFN pathway including the promoter ISRE (Wietek et al. J. Biol. Chem., 278(51), p50923, 2003). Briefly, dsRNA TLR3 agonists were used to induce TLR3 signaling in the reporter assay in the presence of anti-TLR3 antibody 31C3, and TLR3 signaling was assessed. The results, shown in FIG. 9, show that anti-TL3 antibody 31C3 strongly inhibited TLR3 signaling in a dose dependent fashion, compared to a control anti-TLR3 antibody previously determined to have no effect on TLR3 signaling.

Figure 10A:
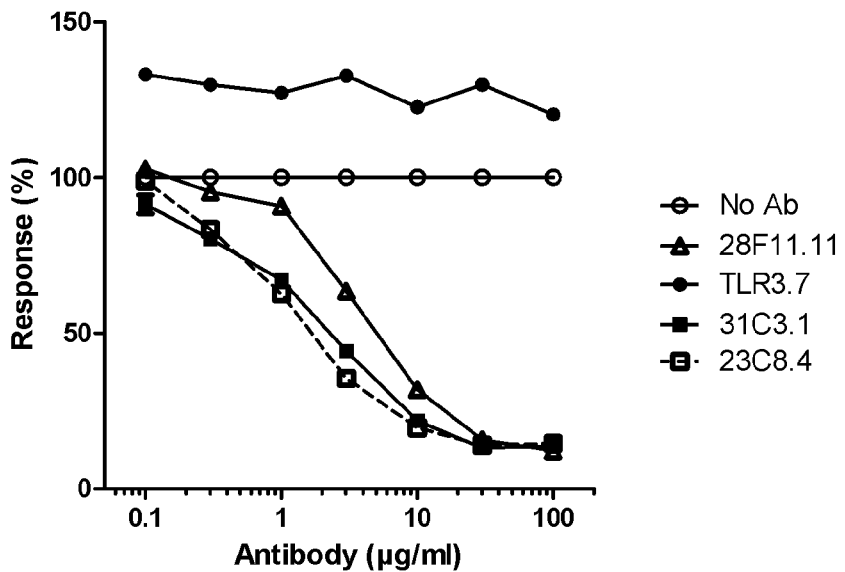
FIG. 10A shows the dose dependant inhibition of TLR3 signalling using a 293T-TLR3 luciferase assay, with the commercial TLR3.7 antibody (black dots), 28F11 (open triangles), 23C8 (open squares) and 31C3 (black squares) antibodies according to the invention, compared to a control (no Ab: open dots).

In a further set of experiments, 293-huTLR3 cells were incubated with different concentrations of the anti-TLR3 mAbs for 24 hours (see FIG. 10A; mAb concentration is represented in axis in µg/ml on a logarithmic scale) followed by the addition to the medium of the TLR3 agonist polyAU at a concentration of 300 µg/ml. Luciferase expression was measured after 24 h based. The results are represented in FIG. 10A, and the IC50 are represented in the Table 2 below indicating that the antibodies according to the invention have excellent inhibition properties.

TABLE 2

| | IC50 (µg/ml) |
|---|---|
| 31C3 | 2.25 |
| 23C8 | 1.83 |
| 28F11 | 5.56 |

Figure 10B:
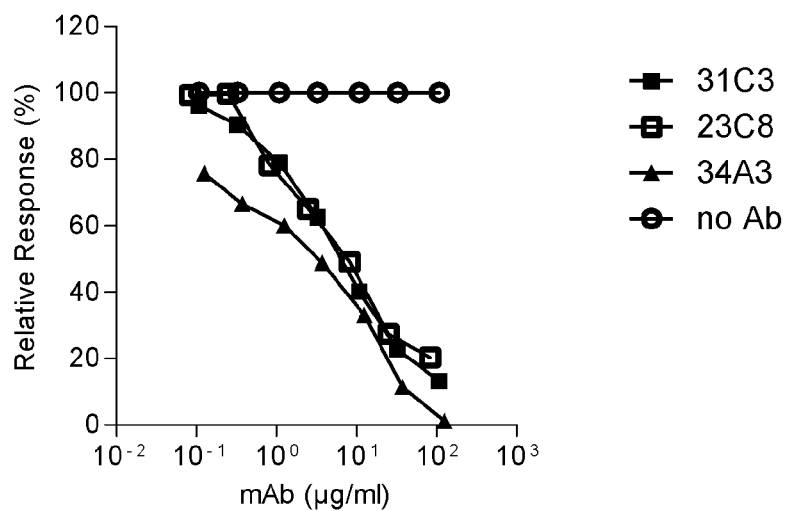
FIG. 10B shows the same results in an assay comparing 31C3 (black squares), 23C8 and 34A3 (black triangles) antibodies.

In another set of experiments, the same inhibition test was carried out with 100 µg/ml of polyAU and test antibodies 31C3, 23E8 and 34A3. IC50 values were calculated and all of the antibodies had an IC50 below 5 µg/ml. Furthermore, 34A3 exhibited an enhanced inhibition effect at low concentrations (FIG. 10B). FIGS. 10A and 10B show the inhibition properties of increasing doses of the antibodies according to the invention, the inhibition of the TLR3 signaling is dose dependant. This assay confirms the excellent inhibition properties of the antibodies according to the invention.

In a further test, the inhibition properties of the antibodies according to the invention were assessed in an inflammatory situation, here in the presence of IFNα. Briefly, three different conditions were tested. In condition 1 (FIG. 11A), IP-10 secretion was assessed without any pretreatment; in condition 2 (FIG. 11B), IP-10 secretion was assessed after a 24 hours pre-treatment with IFNα (1000 UI/ml); in condition 3 (FIG. 11C), IP-10 secretion was assessed after a 24 hours pretreatment with polyAU (300 μg/ml), then a dose range of dsRNA (polyIC for FIGS. 11A and 11B, polyAU for FIG. 11C) and the anti-TLR3 antibody, either 31C3 or 23C8, at a concentration of 50 μg/ml, were added, IP-10 secretion was quantified (in μg/ml) after 24 hours, using ELISA.

Figure 11:
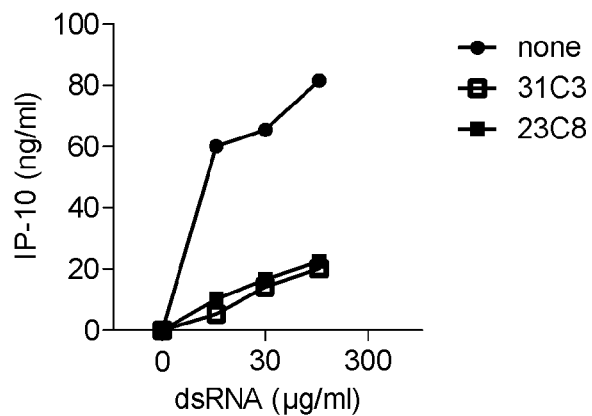
FIG. 11 shows the effect of the 31C3 (open squares) or 23C8 (black full squares) antiTLR3 antibodies in different conditions compared to no antibody (black dots). IP-10 secretion is indicated in ng/ml in ordinates, the dose of dsRNA added is indicated in µg/ml in axis.
Figure 11:
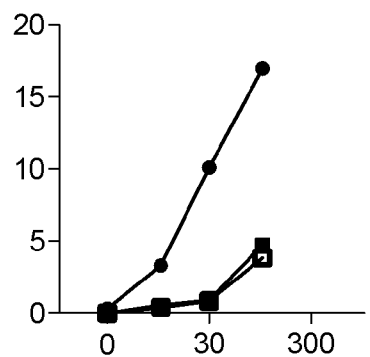
Figure 11:
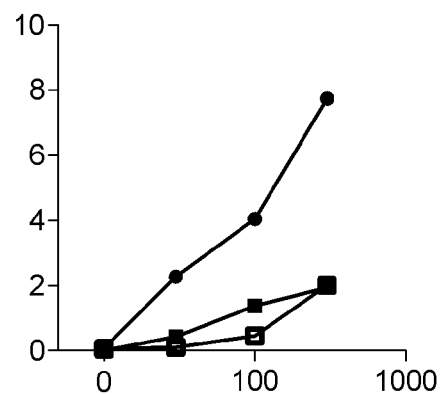

The results, represented in FIG. 11, highlight that the antibodies according to the invention remain good inhibitors of TLR3 even in the presence of stimulatory molecules, either dsRNA or inflammatory cytokines. Such conditions mimic pre-established inflammatory diseases.

Example 6

FACS Staining

Figure 13:
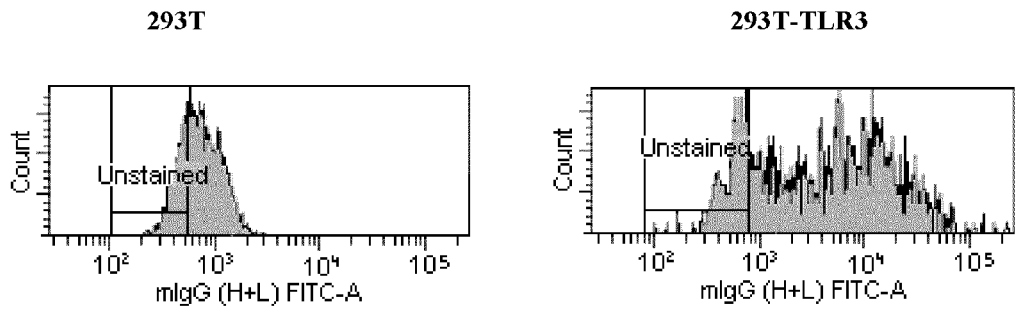
FIG. 13 shows specific recognition of human TLR3 by 31C3 mAb in TLR3 expressing cells, in vitro. Histogram profile for intracellular FACS staining with 31C1 mAb are shown for HEK 293T control cells and 293T cells transfected with human TLR3. Unstained represents the Fluorescence Intensity range obtained with control isotype IgG1

Briefly, 293T or 293T-ISRE/TLR3 cell lines are collected, the medium was washed, and cells were fixed and permeabilized using a IntraPrep™ permeabilization reagent from Beckman Coulter, following the manufacturer instruction. Permeabilized cells were then incubated at RT for 20 min with 25 μg/mL of 31C3 antibody, further revealed by a goat anti-mouse antibody labeled with FITC. The graphs are represented in FIG. 13. FIG. 13A represents the negative control on HEK293T cell line. FIG. 13B represents the staining obtained on HEK293T-TLR3 cells. Cells incubated with control isotype antibody, instead of 31C3 anti-TLR3 antibody were unstained.

The staining obtained using antibody 31C3 in permeabilized cells indicates that the antibodies specifically recognizes and binds intracellular human TLR3 in cells.

Example 7

Kinetic Studies

Figure 12A:
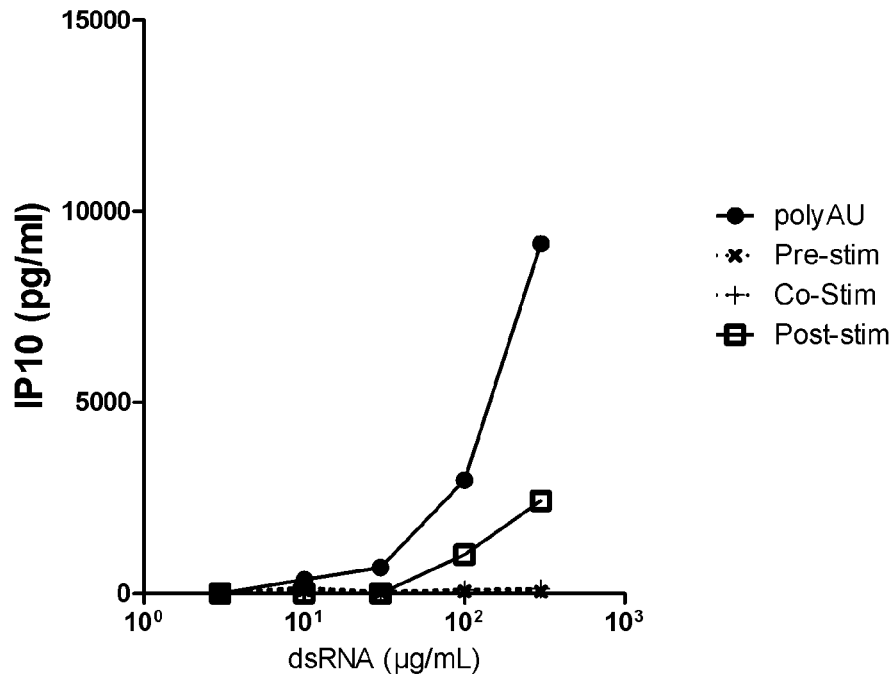
FIG. 12A represents the IP-10 secretion in ng/ml (depending on the polyAU doses) for the 31C3 antibody.
Figure 12B:
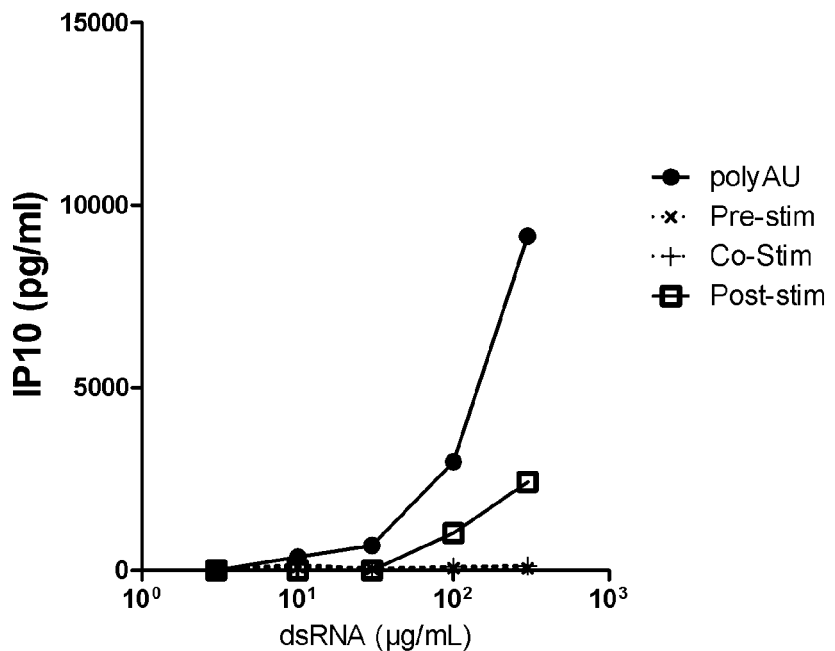
FIG. 12B represents the results for the 23C8 antibody. The TLR3 mAb is added in the medium either 1 h 30 before (black crosses), together with (black plus "+"), or 1 h 30 after (open squares) the dsRNA, the dsRNA alone (black dots) is provided as a positive control).

Another set of assays were performed to determine the kinetics of inhibition of the antibodies according to the invention. Briefly, MdDC were incubated with an anti TLR3 antibody (31C3 or 23C8, at a concentration of 50 μg/ml) and a dose range of polyAU in various time settings. The medium was then incubated for 24 hours and IP-10 secretion was measured by ELISA. FIG. 12A represents the IP-10 secretion in ng/ml (depending on the polyAU doses) for the 31C3 antibody; FIG. 12B represents the results for the 23C8 antibody.

Pre-stim: The anti-TLR3 antibody was incubated 1 h 30 prior to dsRNA addition.

Co-stim: The anti-TLR3 antibody and the dsRNA were added simultaneously.

Post-stim: The dsRNA was incubated 1 h 30 prior to anti-TLR3 antibody addition

These results underline that the antibodies according to the invention are efficient for TLR3 inhibition irrespective of the binding state of the dsRNA to the TLR3 protein. The antibodies do not compete with the binding site of dsRNA but still are able to inhibit TLR3 signaling, even when dsRNA is already bound to the TLR3 protein.

Example 8

TLR3 Internalization Assays

Figure 20A:
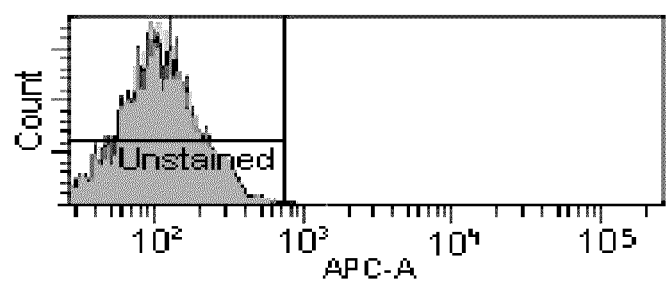
Figure 20B:
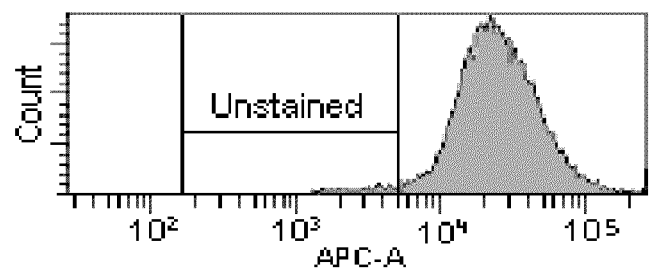
Figure 20C:
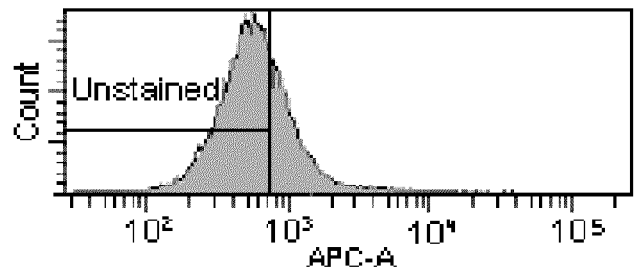
Figure 20D:
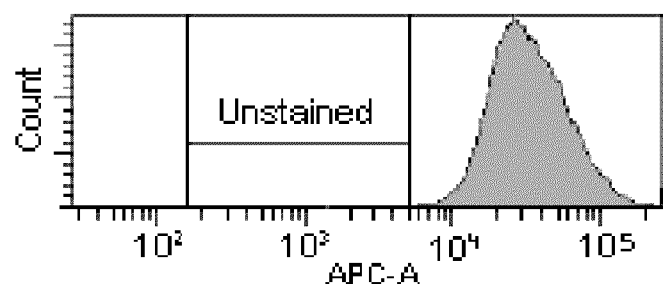
Figure 20E:
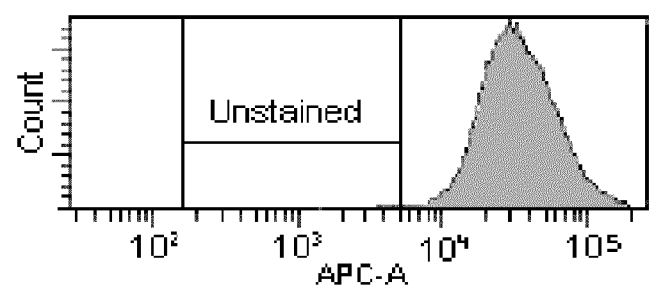

Briefly, either no antibody or 50 μg/mL of the anti-TLR3 antibody 31C3 was incubated with live 293T-ISRE/TLR3 cell lines, for 2 h or 24 h at 37° C. Cells were then washed, fixed and permeabilized using IntraPrep permeabilization reagent from Beckman Coulter. Presence of TLR3-bound anti-TLR3 31C3 Ab is revealed with a goat anti-mouse Ab, labelled with APC. Alternatively, permeabilized cells were incubated with either control isotype or with a TLR3 specific mAb efficient in FACS, noncompeting with 31C3 Ab for TLR3 binding, both labelled with biotin, and further revealed through cell incubation with fluorescent streptavidin derivative. The graphs are represented in FIG. 20. FIG. 20 A represents the negative control, representing fluorescence intensity of the 293T-ISRE/TLR3 cells in the absence of an antibody linking TLR3 proteins. FIGS. 20 C and D represent the fluorescence induced by the binding to TLR3 protein of internalized 31C3 antibody, after 24 h or 2 h incubation, respectively. FIG. 20 B indicates the steady state level of TLR3 expression in 293T-ISRE/TLR3 cell lines, without pre-incubation with 31C3 antibody. FIGS. 20D and 20E, showing a similar fluorescence than FIG. 20B confirm that the binding of TLR3 by antibody 31C3 does not down-modulate the expression of TLR3 on 293T-ISRE/TLR3 cell lines.

Those results show that the antibodies according to the invention are rapidly and efficiently internalized, moreover without any hTLR3 down-modulation. These results underline the efficiency of the binding of the antibodies according to the invention. Furthermore, this rapid internalization provides evidence that the antibodies are promising candidates for therapy. Such antibodies are also promising candidates for coupling with a toxic agent, thereby allowing a specific targeting of TLR3 expressing cells.

All headings and sub-headings are used herein for convenience only and should not be construed as limiting the invention in any way. Any combination of the above-described elements in all possible variations thereof is encompassed by the invention unless otherwise indicated herein or otherwise clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as reference to an element or elements is intended to provide support for a similar aspect or embodiment of the invention that "consists of," "consists essentially of" or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

All publications and patent applications cited in this specification are herein incorporated by reference in their entireties as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

---

What is claimed is:

1. A monoclonal antibody that specifically binds a human Toll-like receptor 3 (TLR3) polypeptide, wherein said antibody inhibits signaling by said human TLR3 polypeptide without blocking binding of a double-stranded ribonucleic acid (dsRNA) TLR3 ligand to said human TLR3 polypeptide.

2. The antibody of claim 1, wherein said antibody is conjugated or covalently bound to a toxic moiety.

3. The antibody of claim 1, wherein said antibody is capable of being internalized by a TLR3-expressing cell.

4. The antibody of claim 3, wherein said TLR3-expressing cell is a cancer cell.

5. The antibody of claim 1, wherein said antibody is conjugated or covalently bound to a detectable moiety.

6. A hybridoma or recombinant host cell producing the antibody of claim 1.

7. A pharmaceutical composition comprising an antibody of claim 1 and a pharmaceutically acceptable carrier.

8. The monoclonal antibody of claim 1, wherein the monoclonal antibody is an antibody having the heavy chain CDR 1, 2 and 3 (HCDR1, HCDR2, HCDR3) amino acid sequences as shown in SEQ ID NO: 4, 5 and 6, respectively.

9. The monoclonal antibody of claim 8, wherein the monoclonal antibody further comprises the light chain CDR 1, 2 and 3 (LCDR1, LCDR2, LCDR3) amino acid sequences as shown in SEQ ID NO: 8 and 9, respectively.

10. A monoclonal antibody that specifically binds a human Toll-like receptor 3 (TLR3) polypeptide, wherein said antibody specifically binds to said human TLR3 polypeptide under acidic conditions with a sub-nanomolar $K_D$ for its bivalent binding affinity.

11. The antibody of claim 10, wherein said antibody modulates TLR3 signaling without blocking binding of a dsRNA TLR3 ligand to said human TLR3 polypeptide.

12. The antibody of claim 11, wherein said antibody inhibits TLR3 signaling.

13. The antibody of claim 10, wherein said antibody inhibits TLR3 signaling.

14. The antibody of claim 10, wherein said acidic conditions comprise a pH between 4.5 and 6.5.

15. The antibody of claim 14, wherein said antibody specifically binds to said human TLR3 polypeptide under neutral conditions with a sub-nanomolar $K_D$ for bivalent binding affinity.

16. The antibody of claim 15, wherein said neutral conditions comprise a pH between 6.6 and 7.4.

17. The antibody of claim 10, wherein said antibody is conjugated or covalently bound to a toxic moiety.

18. The antibody of claim 10, wherein said antibody is capable of being internalized by a TLR3-expressing cell.

19. The antibody of claim 18, wherein said TLR3-expressing cell is a cancer cell.

20. The antibody of claim 10, wherein said antibody is conjugated or covalently bound to a detectable moiety.

21. A hybridoma or recombinant host cell producing the antibody of claim 10.

22. A pharmaceutical composition comprising an antibody of claim 10 and a pharmaceutically acceptable carrier.

23. The monoclonal antibody of claim 10, wherein the monoclonal antibody is an antibody having the heavy chain CDR 1, 2 and 3 (HCDR1, HCDR2, HCDR3) amino acid sequences as shown in SEQ ID NO: 4, 5 and 6, respectively.

24. The monoclonal antibody of claim 23, wherein the monoclonal antibody further comprises the light chain CDR 1, 2 and 3 (LCDR1, LCDR2, LCDR3) amino acid sequences as shown in SEQ ID NO: 7, 8 and 9, respectively.

25. An isolated antibody that specifically binds a human Toll-like receptor 3 (TLR3) polypeptide, wherein said antibody has respectively a VH and VL region of SEQ ID NO: 2 and 3 (31C3), and wherein said isolated antibody is a non-naturally occurring antibody.

26. The antibody of claim 25, wherein said antibody is an antibody having the heavy chain CDR 1, 2 and 3 (HCDR1, HCDR2, HCDR3) amino acid sequences as shown in SEQ ID NO: 4, 5 and 6, respectively.

27. The antibody of claim 26, wherein the antibody further comprises the light chain CDR 1, 2 and 3 (LCDR1, LCDR2, LCDR3) amino acid sequences as shown in SEQ ID NO: 7, 8 and 9, respectively.

28. The antibody of claim 25, wherein said antibody is a mouse antibody.

29. The antibody of claim 25, wherein said antibody is a chimeric, human or humanized antibody.

30. The antibody of claim 29, wherein said antibody is of an IgG isotype.

31. The antibody of claim 30, wherein the isotype of said antibody is an IgG4.

32. The antibody of claim 29, wherein said antibody is an antibody fragment selected from Fab, Fab', Fab'-SH, F (ab')2, Fv, diabodies, single-chain antibody fragment, or a multispecific antibody comprising multiple different antibody fragments.

33. The antibody of claim 25, wherein said antibody is conjugated or covalently bound to a toxic moiety.

34. The antibody of claim 25, wherein said antibody is capable of being internalized by a TLR3-expressing cell.

35. The antibody of claim 34, wherein said TLR3-expressing cell is a cancer cell.

36. A hybridoma or recombinant host cell producing the antibody of claim 25.

37. A pharmaceutical composition comprising an antibody of claim 25 and a pharmaceutically acceptable carrier.

38. The isolated antibody of claim 25, wherein said isolated antibody specifically binds under acid conditions to a human Toll-like receptor 3 (TLR3) polypeptide.

39. The isolated antibody of claim 25, wherein said isolated antibody specifically binds under neutral conditions a human Toll-like receptor 3 (TLR3).

40. An isolated antibody that specifically binds a human Toll-like receptor 3 (TLR3) polypeptide, wherein said antibody is selected from the group consisting of:
  (a) an antibody having respectively a VH and VL region of SEQ ID NO: 34 and 35 (34A3),
  (b) an antibody having respectively a VH and VL region of SEQ ID NO: 10 and 11 (29H3),
  (c) an antibody having respectively a VH and VL region of SEQ ID NO: 18 and 19 (28F11), and
  (d) an antibody having respectively a VH and VL region of SEQ ID NO: 26 and 27 (23C8)
  wherein said isolated antibody is a non-naturally occurring antibody.

41. The antibody of claim 40, wherein the antibody is an antibody having (i) the heavy chain CDR 1, 2 and 3 (HCDR1, HCDR2, HCDR3) amino acid sequences as shown in SEQ ID NO: 12, 13 and 14, and (ii) the light chain CDR 1, 2 and 3 (LCDR1, LCDR2, LCDR3) amino acid sequences as shown in SEQ ID NO: 15, 16 and 17, respectively.

42. The antibody of claim 40, wherein the antibody is an antibody having (i) the heavy chain CDR 1, 2 and 3 (HCDR1, HCDR2, HCDR3) amino acid sequences as shown in SEQ ID NO: 20, 21 and 22, and (ii) the light chain CDR 1, 2 and 3 (LCDR1, LCDR2, LCDR3) amino acid sequences as shown in SEQ ID NO: 23, 24 and 25, respectively.

43. The antibody of claim 40, wherein the antibody is an antibody having (i) the heavy chain CDR 1, 2 and 3 (HCDR1, HCDR2, HCDR3) amino acid sequences as shown in SEQ ID NO: 28, 29 and 30, and (ii) the light chain CDR 1, 2 and 3 (LCDR1, LCDR2, LCDR3) amino acid sequences as shown in SEQ ID NO: 31, 32 and 33, respectively.

44. The antibody of claim 40, wherein the antibody is an antibody having (i) the heavy chain CDR 1, 2 and 3 (HCDR1, HCDR2, HCDR3) amino acid sequences as shown in SEQ ID NO: 36, 37 and 38, and (ii) the light chain CDR 1, 2 and 3 (LCDR1, LCDR2, LCDR3) amino acid sequences as shown in SEQ ID NO: 39, 40 and 41, respectively; and wherein one, two, three or more of the amino acids in any of said sequences may be substituted by a different amino acid.

45. The antibody of claim 40, wherein said antibody specifically binds said human TLR3 polypeptide under acid conditions.

46. The antibody of claim 40 wherein said antibody specifically binds said human TLR3 polypeptide under neutral conditions.

47. The antibody of claim 40 wherein said antibody is a monoclonal antibody.

48. A pharmaceutical composition comprising the antibody of claim 40 and a pharmaceutically acceptable carrier.

49. A method of producing an antibody that specifically binds a Toll-like receptor 3 (TLR3) polypeptide in a mammalian subject, said method comprising the steps of: a) immunizing a non-human mammal with an immunogen comprising a human TLR3 polypeptide; and b) selecting an antibody from said immunized animal that binds to said human TLR3 polypeptide with high affinity under acidic and neutral conditions and that modulates TLR3 signaling.

50. A method of producing an antibody that specifically binds a Toll-like receptor 3 (TLR3) polypeptide in a mammalian subject, said method comprising the steps of: a) immunizing a non-human mammal with an immunogen comprising a human TLR3 polypeptide; and b) selecting an antibody from said immunized animal that inhibits TLR3 signaling without blocking binding of a TLR3 ligand to said human TLR3 polypeptide.

51. An isolated antibody that specifically binds human Toll-like receptor 3 (TLR3) polypeptide, wherein said isolated antibody is selected from the group consisting of monoclonal antibodies 31C3, 29H3, 23C8, 28F11, and 34A3 wherein the isolated antibody is a non-naturally occurring antibody.

52. An isolated antibody which is specific for an epitope in the human Toll-like receptor 3 (TLR3) polypeptide that does not undergo substantial change in electrostatic potential or undergoes less change than a region of positive electrostatic potential when neutral conditions are acidified such that the binding affinity of said antibody remains substantially unchanged, wherein the isolated antibody is a non-naturally occurring antibody.

53. A pharmaceutical composition comprising the antibody of claim 52 and a pharmaceutically acceptable carrier.

54. An isolated antibody which specifically binds to the same human Toll-like receptor 3 (TLR3) epitope as any one or any combination of monoclonal antibodies 31C3, 29H3, 23C8, 28F11 or 34A3 wherein the isolated antibody is a non-naturally occurring antibody.

55. A pharmaceutical composition comprising the antibody of claim 54 and a pharmaceutically acceptable carrier.

* * * * *